(12) United States Patent
Straub et al.

(10) Patent No.: US 8,530,505 B2
(45) Date of Patent: Sep. 10, 2013

(54) SUBSTITUTED OXAZOLIDINONES AND THEIR USE IN THE FIELD OF BLOOD COAGULATION

(75) Inventors: Alexander Straub, Wuppertal (DE); Thomas Lampe, Wuppertal (DE); Jens Pohlmann, Wuppertal (DE); Susanne Röhrig, Essen (DE); Elisabeth Perzborn, Wuppertal (DE); Karl-Heinz Schlemmer, Wuppertal (DE); Joseph Pernerstorfer, Wuppertal (DE)

(73) Assignee: Bayer Intellectual Property GmbH, Monheim am Rhein (DE)

( * ) Notice: Subject to any disclaimer, the term of this patent is extended or adjusted under 35 U.S.C. 154(b) by 0 days.

(21) Appl. No.: 13/360,107

(22) Filed: Jan. 27, 2012

(65) Prior Publication Data

US 2013/0005701 A1   Jan. 3, 2013

Related U.S. Application Data

(63) Continuation of application No. 12/494,879, filed on Jun. 30, 2009, now Pat. No. 8,129,378, which is a continuation of application No. 11/932,082, filed on Oct. 31, 2007, now Pat. No. 7,576,111, which is a continuation of application No. 11/460,529, filed on Jul. 27, 2006, now Pat. No. 7,592,339, which is a continuation of application No. 10/181,051, filed as application No. PCT/EP00/12492 on Dec. 11, 2000, now Pat. No. 7,157,456.

(51) Int. Cl.
*A61K 31/42*  (2006.01)
*C07D 409/14*  (2006.01)

(52) U.S. Cl.
USPC .......................................... 514/376; 548/231

(58) Field of Classification Search
USPC .......................................... 514/376; 548/231
See application file for complete search history.

(56) References Cited

U.S. PATENT DOCUMENTS

| | | |
|---|---|---|
| 2,811,555 A | 10/1957 | Larive et al. |
| 3,279,880 A | 10/1966 | Straley et al. |
| 4,128,654 A | 12/1978 | Fugitt et al. |
| 4,250,318 A | 2/1981 | Dostert et al. |
| 4,327,725 A | 5/1982 | Cortese et al. |
| 4,500,519 A | 2/1985 | Lormeau et al. |
| 4,705,779 A | 11/1987 | Madi-Szabo et al. |
| 4,765,989 A | 8/1988 | Wong et al. |
| 5,002,937 A | 3/1991 | Bosies et al. |
| 5,254,577 A | 10/1993 | Carlson et al. |
| 5,349,045 A | 9/1994 | Jiang |
| 5,532,255 A | 7/1996 | Raddatz et al. |
| 5,561,148 A | 10/1996 | Gante et al. |
| 5,565,571 A | 10/1996 | Barbachyn et al. |
| 5,654,428 A | 8/1997 | Barbachyn et al. |
| 5,654,435 A | 8/1997 | Barbachyn et al. |
| 5,688,792 A | 11/1997 | Barbachyn et al. |
| 5,756,732 A | 5/1998 | Barbachyn et al. |
| 5,792,765 A | 8/1998 | Riedl et al. |
| 5,801,246 A | 9/1998 | Barbachyn et al. |
| 5,827,857 A | 10/1998 | Riedl et al. |
| 5,910,504 A | 6/1999 | Hutchinson et al. |
| 5,922,708 A | 7/1999 | Riedl et al. |
| 5,929,248 A | 7/1999 | Barbachyn et al. |
| 5,972,947 A | 10/1999 | Tsaklakidis et al. |
| 6,069,160 A | 5/2000 | Stolle et al. |
| 6,251,869 B1 | 6/2001 | Bohanon |
| 6,273,913 B1 | 8/2001 | Wright et al. |
| 6,294,201 B1 | 9/2001 | Kettelhoit et al. |
| 6,413,981 B1 | 7/2002 | Paget et al. |
| 6,610,682 B2 | 8/2003 | Tsujita et al. |
| 6,805,881 B1 | 10/2004 | Kanikanti et al. |
| 6,818,243 B2 | 11/2004 | Nagashima et al. |
| 7,034,017 B2 | 4/2006 | Straub et al. |
| 7,045,631 B2 | 5/2006 | Rosentreter et al. |
| 7,078,417 B2 | 7/2006 | Rosentreter et al. |

(Continued)

FOREIGN PATENT DOCUMENTS

| | | |
|---|---|---|
| AU | 744002 | 7/1999 |
| CA | 2 437 587 | 8/2002 |

(Continued)

OTHER PUBLICATIONS

Abendschein, D., Ph.D. et al., "Inhibition of Thrombin Attenuates Stenosis After Arterial Injury in Minipigs," J. Am. Col. Card., vol. 28, No. 7, Dec. 1996; pp. 1849-1855.

Adamset al., "Sulfanilimide Derivatives," J. Am. Chem. Soc. 1939, 61, 2342-2349.

(Continued)

*Primary Examiner* — Rebecca Anderson
(74) *Attorney, Agent, or Firm* — Buchanan, Ingersoll & Rooney PC

(57) ABSTRACT

The invention relates to the field of blood coagulation. Novel oxazolidinone derivatives of the general formula (I)

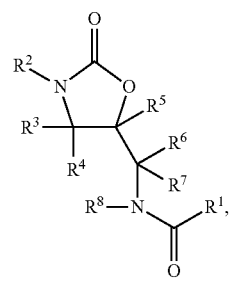

(I)

processes for their preparation and their use as medicinally active compounds for the prophylaxis and/or treatment of disorders are described.

21 Claims, No Drawings

(56) References Cited

U.S. PATENT DOCUMENTS

| | | |
|---|---|---|
| 7,109,218 B2 | 9/2006 | Rosentreter et al. |
| 7,129,255 B2 | 10/2006 | Rosentreter et al. |
| 7,157,456 B2 | 1/2007 | Straub et al. |
| 7,351,823 B2 | 4/2008 | Berwe et al. |
| 2001/0029351 A1 | 10/2001 | Falotico et al. |
| 2003/0153610 A1 | 8/2003 | Straub et al. |
| 2003/0161882 A1 | 8/2003 | Waterman |
| 2004/0162427 A1 | 8/2004 | Rosentreter et al. |
| 2004/0242660 A1 | 12/2004 | Straub et al. |
| 2005/0064006 A1 | 3/2005 | Perzborn et al. |
| 2005/0182055 A1 | 8/2005 | Berwe et al. |
| 2005/0261502 A1 | 11/2005 | Rosentreter et al. |
| 2006/0154969 A1 | 7/2006 | Rosentreter et al. |
| 2006/0258724 A1 | 11/2006 | Straub et al. |
| 2007/0026065 A1 | 2/2007 | Benke et al. |
| 2007/0149522 A1 | 6/2007 | Thomas |
| 2008/0026057 A1 | 1/2008 | Benke |
| 2008/0090815 A1 | 4/2008 | Straub et al. |
| 2008/0200674 A1 | 8/2008 | Straub et al. |

FOREIGN PATENT DOCUMENTS

| | | |
|---|---|---|
| CA | 2 451 258 | 1/2003 |
| CA | 2 464 290 | 5/2003 |
| DE | 2836305 A1 | 3/1979 |
| DE | 196 04 223 | 8/1997 |
| DE | 19962924 A1 | 7/2001 |
| DE | 10105989 A1 | 8/2002 |
| DE | 10129725 A1 | 1/2003 |
| DE | 10355461 A1 | 6/2005 |
| EP | 0 127 902 | 12/1984 |
| EP | 0 316 594 | 5/1989 |
| EP | 0 352 781 | 1/1990 |
| EP | 0350002 A1 | 1/1990 |
| EP | 0 623 615 | 11/1994 |
| EP | 0 645 376 | 3/1995 |
| EP | 0 738 726 | 10/1996 |
| EP | 0 785 200 | 7/1997 |
| EP | 0930076 A1 | 7/1999 |
| EP | 0950386 A2 | 10/1999 |
| GB | 2140687 | 12/1984 |
| WO | WO-93/09103 | 5/1993 |
| WO | WO-93/23384 | 11/1993 |
| WO | WO-97/03072 | 1/1997 |
| WO | WO-97/09328 | 3/1997 |
| WO | WO-97/10223 | 3/1997 |
| WO | WO-98/01446 | 1/1998 |
| WO | WO-98/54161 | 12/1998 |
| WO | WO-99/02525 | 1/1999 |
| WO | WO-99/03846 | 1/1999 |
| WO | WO-99/06371 | 2/1999 |
| WO | WO-99/21535 A1 | 5/1999 |
| WO | WO-99/24428 | 5/1999 |
| WO | WO-99/29688 A1 | 6/1999 |
| WO | WO-99/31092 | 6/1999 |
| WO | WO-99/37304 | 7/1999 |
| WO | WO-99/37630 | 7/1999 |
| WO | WO-99/37641 | 7/1999 |
| WO | WO-99/40094 | 8/1999 |
| WO | WO-99/59616 | 11/1999 |
| WO | WO-00/16748 A1 | 3/2000 |
| WO | WO-01/42242 A1 | 6/2001 |
| WO | WO-01/44212 | 6/2001 |
| WO | WO-01/46185 | 6/2001 |
| WO | WO-01/47919 A1 | 7/2001 |
| WO | WO-01/47949 A1 | 7/2001 |
| WO | WO-02/25210 A1 | 3/2002 |
| WO | WO-02/064575 A1 | 8/2002 |
| WO | WO-02/070484 A1 | 9/2002 |
| WO | WO-02/070485 A1 | 9/2002 |
| WO | WO-02/070520 A1 | 9/2002 |
| WO | WO-02/079195 A1 | 10/2002 |
| WO | WO-02/079196 A1 | 10/2002 |
| WO | WO-03/000256 | 1/2003 |
| WO | WO-03/008384 A1 | 1/2003 |
| WO | WO-03/035133 A1 | 5/2003 |
| WO | WO-03/053441 A1 | 7/2003 |
| WO | WO-2004/060887 | 7/2004 |
| WO | WO-2005/060940 A1 | 5/2005 |
| WO | WO-2005/068456 A1 | 7/2005 |
| WO | WO-2006/072367 A1 | 7/2006 |
| WO | WO-2006/079474 A1 | 8/2006 |
| WO | WO-2007/036306 A1 | 4/2007 |
| WO | WO-2007/039122 A2 | 4/2007 |
| WO | WO-2007/039132 A1 | 4/2007 |
| WO | WO-2007/039134 A1 | 4/2007 |
| WO | WO-2007/042146 A1 | 4/2007 |
| WO | WO-2008/012002 A1 | 1/2008 |
| WO | WO-2008/052671 A1 | 5/2008 |

OTHER PUBLICATIONS

Aebischer et al., "Synthesis of N-Arylrolipram Derivatives—Potent and Selective Phosphodiesterase-IV Inhibitors—by Copper Catalyzed Lactam-Aryl Halide Coupling," Heterocycles. 1998, 48, 2225-2229.

Ai-Obeidi, F., Ostrem, J., "Factor Xa Inhibitors by Classical and Combinatorial Chemistry," *DDT*, 3: 223-231 (May 1998).

Al-Obeidi, F., Ostrem, J., "Factor Xa Inhibitors," *Expert Opin. Therapeutic Patents*, 9: 931-953 (1999).

Altieri, D.et al., "Identification of Effector Cell Protease Receptor-1: A Leukocyte-Distributed Receptor for the Serine Protease Factor Xa," The Journal of Immunology (1990); vol. 145, No. 1, Jul. 1, 1990; pp. 246-253.

Artico, M. et al., "Research on Compounds with Antiblastic Activity," Farmaco Ed. Sci. 1969, 24, 179-190.

Barbachyn, M.R. et al., "Identification of a Novel Oxazolidinone (U-100480) with Potent Antimycobacterial Activity," J. Med. Chem. 1996, 39, 680-685.

Bartoli et al, "Electronic and Steric Effects in Nucleophilic Aromatic Substitution. Reaction by Phenoxides as Nucleophiles in Dimethyl Sulfoxide," J. Org. Chem. 1975, 40, 872-874.

Becker, M.R.et al., "Synthesis, Sar and in Vivo Activity of Novel Thienopyridine Sulfonamide Pyrrolidininones as Factor Xa Inhibitors," *Bioorganic and Medicinal Chemistry Letters*, 9: 2753-2758 (1999).

Benzakour, O.et al., "Cellular and molecular events in atherogenesis; basis for pharmocological and gene therapy approaches to stenosis," Cellular Pharmacology, vol. 3., (1996); pp. 7-22.

Berry, C.N. et al., "Antithrombotic Actions of Argatroban in Rat Models of Venous, 'Mixed' and Arterial Thrombosis, and its Effects on the Tail Transection Bleeding Time," Br. J. Pharmacol. 1994, 113, 1209-1214.

Betz, A. Recent advances in Factor Xa inhibitors. Expert Opinion Ther. Patents 2001, 11, 1007-1017.

Bevilacqua, M., MD, Ph.D.et al., "Inducible Endothelial Functions in Inflammation and Coagulation," Sem. in Thrombosis and Hemostasis, vol. 13, No. 4, 1987; pp. 425-433.

[Database Bielstein] Bielstein Institute for Organic Chemistry, Frankfurt-Main, DE. Database Accession No. 8822985, 2001.

Bono, F.et al., "Factor Xa Activates Endothelial Cells by a Receptor Cascade Between EPR-1 and PAR-2," Arterioscler Thromb Vasc Biol., Nov. 2000; pp. 1-6.

Bono, F.et al., "Human Umbilical Vein Endothelial Cells Express High Affinity Receptors for Factor Xa," Journal of Cellular Physiology; 172:36-43 (1997); pp. 36-43.

Bonomini, V. et al. A New Antithrombotic Agent in the Treatment of Acute Renal Failure Due to Hemolytic-Uremic Syndrome and Thrombotic Thrombocytopenic Purpura. Nephron 37, 1984, 144.

Bots, M.et al., Coagulation and Fibrinolysis Markers and Risk of Dementia, Haemostasis, vol. 28 (1998); pp. 216-222.

Bouchard, B.et al., "Effector Cell Protease Receptor-1, a Platelet Activation-dependent Membrane Protein, Regulates Prothrombinase-catalyzed Thrombin Generation," J. Biological Chemisstry, vol. 272, No. 14, Apr. 4, 1997; pp. 9244-9251.

Bouchet al., J. Chem. Soc. Perkin Trans. 2, 1974, 449-451.

Breitenbach, J. Feste Loesungen durch Schmelzextrusion—ein integriertes Herstellkonzept. Pharmazie in unserer Zeit 29 (2000), 46-49.

Breitenbach, J. Melt extrusion: from process to drug delivery technology. European Journal of Pharmaceutics and Biopharmaceutics 54 (2002) 107-117.

Brickner, S.J. et al., "Synthesis and Antibacterial Activity of U-100592 and U-100766, Two Oxazolidinone Antibacterial Agents for the Potential Treatment of Multidrug-Resistant Gram-Positive Bacterial Infections," J. Med. Chem. 1996, 39, 673.

Caira, M. Crystalline Polymorphism of Organic Compounds. Springer Verlag Berlin Heidelberg 198, 1998, pp. 163-208.

Camerer, E.et al., "Tissue factor- and factor X-dependent activation of protease-activated receptor 2 by factor Vlla," PNAS, vol. 97, No. 10, May 9, 2000; pp. 5255-5260.

Carmeliet, P., MDet al., "Gene Manipulation and Transfer of the Plasminogen and Coagulation System in Mice," Sem. in Thrombosis and Hemostatis, vol. 22, No. 6, 1996; pp. 525-542.

Chern, J.W. et al., "Studies on Quinazolines IX: Fluorination versus 1,2-Migration in the Reaction of 1,3-Bifunctionalized amino-2-propanol with DAST," Tetrahedron Lett. 1998, 39, 8483-8486.

Chiou, W.L. et al. Pharmaceutical Applications of Solid Dispersion Systems. Journal of Pharmaceutical Sciences 60, (1971). 128-1302.

Cirino, G.et al., "Factor Xa as an Interface Between Coagulation and Inflammation," J. Clin. Invest., vol. 99, No. 10, May 1997, pp. 2446-2451.

Cirino, G.et al., "Inflammation-coagulation network: are serine protease receptors the knot?" TiPS—May 2000 (vol. 21); pp. 170-172.

Cocks, Tet al., "Protease-activated receptors: sentries for inflammation?" TiPS; Mar. 2000 (vol. 21); pp. 103-108.

Coughlin, Shaun R., "Thrombin signalling and protease-activated receptors," Nature, vol. 407, Sep. 14, 2000; pp. 258-264.

Dabbagh, K.et al., "Thrombin Stimulates Smooth Muscle Cell Procollagen Synthesis and mRNA Levels via a PAR-1 Mediated Mechanism," Center for Cardiopulmonary Biochemistry and Respiratory Medicine, (1997); pp. 405-409.

Dankwardt et al., "Nonpeptide Bradykinin Antagonist Analogs Based on a Model of a Sterling-Winthrop Nonpeptide Bradykinin Antagonist Overlapped with Cyclic Hexapeptide Bradykinin Antagonist Peptides," Bioorg. Med. Chem. Lett. 1997, 1921-1926.

Delande, S.A., Chem. Abstr., 1979, 90, 186926.

Donnelly, K.et al,, "Ancylostoma canninum Anticoagulant Peptide Blocks Metastasis In Vivo and Inhibits Factor Xa Binding to Melanoma Cells In Vitro," Thromb Haemost 1998; 79; pp. 1041-1047.

Donovan, F.et al., "Thrombin Induces Apoptosis in Cultured Neurons and Astrocytes via a Pathway Requiring Tyrosine Kinase and RhoA Activities," J. Neuroscience, Jul. 15, 1997, vol. 17, No. 14; pp. 5316-5326.

Espinosa, G. et al. Thrombotic microangiopathic haemolytic anaemia and antiphospholipid antibodies. Annals of the Rheumatic Diseases, 63, 6, Jun. 2004, pp. 730-736.

FDA mulls drug to slow late-stage Alzheimer's [online], [retrieved on Sep. 23, 2003]. Retrieved from the internet, URL:http://www.cnn.com/2003/HEALTH/conditions/09/24/alzheimers.drug.ap/index.html>.

Ford, J.L. The Current Status of Solid Dispersions. Pharm Acta Helv. 61, (1986)69-88.

Gasic, G.et al., "Coagulation factors X, Xa, and protein S as potent mitogens of cultured aortic smooth muscle cells," Proc. Natl. Acad. Sci. USA; vol. 89, Mar. 1992, Cell Biology, pp. 2317-2320.

Gilligan, D.M. et al. The Management of Atrial Fibrillation. The American Journal of Medicine, vol. 101, (4) 1996, 413-421.

Golub, T.R. et al., "Molecular classification of cancer: class discovery and class prediction by gene expression monitoring," *Science* (1999), vol. 286, pp. 531-537.

Greaves et al., Novel Approaches to the Preparation of Low-Dose Solid Dosage Forms,Pharmaceutical Technology. Jan., pp. 60-64, (1995).

Green, D.et al., "Lower mortality in cancel patients treated with low-molecular-weight versus standard heparin," Letters to the Editor, The Lancet, vol. 339, Jun. 13, 1992, p. 1476.

Gregory, W.A. et al., "Antibacterials. Synthesis and Structure-Activity Studies of 3-Aryl-2-oxooxazolidines. 1. The "B" Group," J. Med. Chem. 1989, 32, 1673-1681.

Grell, W.et al., "Repaglinide and Related Hypoglycemic Benzoic Acid Derivatives," J. Med. Chem. 1998, 41, 5219-5246.

Gutcalt, A. et al., "Studies on Quinazolines. 6. Asymmetric Synthesis of (S)-(+)- and (R)-(–)- 3[[4-(2-Methoxyphenyl)piperazin-1-yl]methyl]-5-methylthio-2,3-dihydroimidazo[1,2- c]quinazolines," Tetrahedron Asym. 1996, 7, 1641-1648.

Hancock, B. et al. Characteristics and Significance of the Amorphous State in Pharmaceutical Systems. Journal of Pharmaceutical Science. 86, 1 (1997-1), pp. 1-12.

Hauptmann, J., Sturzebecher, J., "Synthetic Inhibitors of Thrombin and Factor Xa: From Bench to Bedside," *Thrombosis Research*, 93: 203-241 (1999).

Herault, J.et al., "Activation of Human Vascular Endothelial Cells by Factor Xa: Effect of Specitic Inhibitors," Biochemical Pharmacology, vol. 57, pp. 603-610, 1999.

Herbert, J.-M,et al., "Effector Protease Receptor 1 Mediates the Mitogenic Activity of Factor Xa for Vascular Smooth Muscle Cells in Vitro and in Vivo," J. Clin. Invest., vol. 101, No. 5 (1998); pp. 993-1000.

Howells, G.et al,, "Proteinase-activated receptor-2: expression by human neutrophils," Journal of Cell Science 110 (1997); pp. 881-887.

http://familydoctor.org/online/famdocen/home/common/heartdisease/basics/290.html (created Sep. 2000, updated/reviewed Nov. 2006).

Justus Liebigs Ann. Chem. 1955, 596, 204.

Kaiser, B., "Thrombin and Factor Xa Inhibitors," *Drugs of the Future*, 23: 423-426 (1998).

Kaiser, B.et al., "A Synthetic Inhibitor of Factor Xa, DX-9065a, Reduces Proliferation of Vascular Smooth Muscle Cells in Vivo in Rats," Elsevier Science Ltd., Thrombosis Research 98 (2000); pp. 175-185.

Kaiser, B.et al., "Antiproliferation Action of Factor Xa Inhibitors in a Rat Model of Chronic Restenosis," Abstracts of the XVIIth Congress of the International Society on Thrombosis and Haemostasis, Aug. 1999, p. 144.

Kakkar, A.et al., "Antithrombotic therapy in cancer," BMJ, vol. 318, Jun. 1999, pp. 1571-1572.

Kanthou, C.et al., "Cellular effects of thrombin and their signalling pathways," Cellular Pharmacology, vol. 2 (1995); pp. 293-302.

Khanna, I.K. et al., "1,2-Diarylpyrroles as Potent and Selective Inhibitors of Cyclooxygenase-2," J. Med. Chem. 1997, 40 ,1619-1633.

Ko, F.et al., "Coagulation Factor Xa Stimulates Platelet-derived Growth Factor Release and Mitogenesis in Cultured Vascular Smooth Muscle Cells of Rat," J. Clin. Invest., vol. 98, No. 6, Sep. 1996; pp. 1493-1501.

Kranzhöfer, R.et al., "Thrombin Potently Stimulates Cytokine Production in Human Vascular Smooth Muscle Cells but Not in Mononuclear Phagocytes," Circulation Research, vol. 79, No. 2, Aug. 1996; pp. 286-294.

Kubitza, D. et al. Novel factor Xa inhibitors for prevention and treatment of thromboembolic diseases. Expert Opinion on Investig. Drugs, vol. 15, (8) 2006, pp. 843-855.

Kubitzaet al., Abstract 3010, Single dose escalation study investigating the pharmacodyanamlcs, safety, and pharmacokinetics of BAY 59/7939 an oral, direct Factor Xa inhibitor in healthy male subjects, Blood, vol. 102:11. Nov. 16, 2003, p. 813a.

Kubitzaet al., Multiple dose escalation study Investigating the pharmacodyanamics, safety, and pharmacokinetics of BAY 59/7939 an oral, direct Factor Xa inhibitor in healthy male subjects, Blood, vol. 102:11: Nov. 16, 2003, p. 811a.

Lala, P.K. et al., "Role of nitric oxide in tumor progressin: lessons from experimental tumors," *Cancer and Metastasis Review*, vol. 17, pp. 91-106 (1998).

Leadley, R.J. Coagulation Factor Xa Inhibition: Biological Background and Rationale. Current Topics in Medical Chemistry 2001, 1, 151-159.

Lerket al., Effect of Hydrophilization Drugs on Release Rat from Capsules, J. of Pharma. Sciences, 67(7), pp. 935-939 (1978).

Lerket al., In Vitro and in Vivo Availability of Hydrophilized Phenytoin from Capsules, J. of Pharma. Sciences, 68(5), pp. 634-638 (1979).

Leveugle, B.et al., "Heparin Oligosaccharides that Pass the Blood—Brain Barrier Inhibit β-Amyloid Precursor Protein Secretion and Heparin Binding to β-Amyloid Peptide," Journal of Neurochemistry, vol. 70, No. 2, 1998; pp. 736-744.

Lindner, J. et al., "Delayed Onset of Inflammation in Protease-Activated Receptor-2-Deficient Mice," J. Immunology, 2000, pp. 6504-6510.

LuValle, J.E. et al., "Oxidation Processes. XXI. The Autoxidation of the ρ-Phenylenediamines," J. Am. Chem. Soc. 1948, 70, 2223.

Meng, K. et al., "Effect of Acetylsalicylic Acid on Experimentally Induced Arterial Thrombosis in Rats," Naunyn-Schmiedeberg's Arch. Pharmacol. 1977, 301, 115-119.

Molino, M. et al., "Differential Expression of Functional Protease-Activated Receptor-2 (PAR-2) in Human Vascular Smooth Muscle Cells," Dept. of Medicine and Center for Experimental Therapeutics; U. of Penn.; 1997; pp. 825-832.

Molino, M. et al., "Endothelial Cell Thrombin Receptors and PAR-2," J. Biological Chem., vol. 272, No. 17, Apr. 25, 1997; pp. 11133-11141.

Nakata, M. et al.; "DX9065a, an Xa inhibitor, inhibits prothrombin-induced A549 lung adenocarcinoma cell proliferation," Elsevier Science Ireland Ltd., Cancer Letters 122 (1998); pp. 127-133.

Nicholson, A. et al., "Effector Cell Protease Receptor-1 Is a Vascular Receptor for Coagulation Factor Xa," J. Biological Chem., vol. 271, No. 45, Nov. 8, 1996; pp. 28407-28413.

Ornstein, D., MD et al., "Cancer, thrombosis, and anticoagulants," Current Opinion in Pulmonary Medicine, 2000, pp. 301-308.

Papapetropoulos, A. et al., "Hypotension and inflammatory cytokine gene expression triggered by factor Xa-nitric oxide signaling," Proc. Natl. Acad. Sci. USA; vol. 95, Pharmacology, Apr. 1998, pp. 4738-4742.

Perzborn, E. et al. In vitro and in vivo studies of the novel antithrombotic agent BAY 59-7939-an oral, direct Factor Xa inhibitor. Journal of Thrombosis and Haemostasis 3, Mar. 3, 2005, pp. 514-521.

Pfeil, E. et al., "Synthese von Oxalactamen aus Aziridinium-tetrafluoroborat und Hydroxysaureestern," Agnew Chem. 79, 1967, 188.

Plescia, J. et al., "Activation of Mac-1 (CD11b/CD18)-bound factor X by released cathepsin G defines an alternative pathway o leucoyte initiation of coagulation," Journal of Biochemistry, vol. 319 (1996); pp. 873-879.

Pschyrembel, Klinisches Worterbuch, 257. Auflage, 1994, Walter de Gruyter Verlag, p. 199-200, Stichwort "Blutgerinnung".

Pschyrembel, Klinisches Worterbuch, 257. Auflage, 1994, Walter de Gruyter Verlag, p. 610, Stichwort "Heparin".

Pschyrembel, Klinisches Worterbuch, 257. Auflage, 1994, Walter de Gruyter Verlag, p. 292, Stichwort "Cumarinderivate".

Quan, M.L. The race to an orally active Factor Xa inhibitor: Recent advances. Current Opinion in Drug Discovery & Development 2004, 7, 460-469.

Ragosta, M., MD et al., "Specific Factor Xa Inhibition REduces Restenosis After Balloon Angioplasty of Atherosclerotic Femoral Arteries in Rabbits," Circulation, vol. 89, No. 3, Mar. 1994; pp. 1262-1271.

Rasenack, N. et al. Poorly Water-soluble Drugs for Oral Delivery—A Challenge for Pharmaceutical Development. Pharmazeutische Industrie 67, Nr. 5 (2005), 583-591.

Renger, "Direct N-Arylation of Amides: An Improvement of the Goldberg-Reaction," Synthesis Sep. 1985, 856-860.

Reppe et al., Justus Liebigs Ann, Chem. 1955, vol. 596, p. 204.

Reppe et al., Justus Liebigs Ann. Chem. 596, 1955, p. 209.

Riedl, B., Endermann, "Recent Developments with Oxazolidinone Antibiotics," R., Exp. Opin. Ther. Patents 1999, 9 (5), 625-633.

Roehrig, S. et al. Discovery of the Novel Antithrombotic Agent 5-Chloro-N-(((5S)-2-oxo-3-[4-(3-oxomorpholin-4-yl)phenyl]-1,3-oxazolidin-5-yl}methyl)thiophene-2-carboxamide (BAY 59-7939): An Oral, Direct Factor Xa Inhibitor. J. Med. Chem. 48, Sep. 22, 2005, pp. 5900-5908.

Rompp Lexikon Chemie, Ver. 1.5, 1998, Georg Thieme Verlag Stuttgart, Stichwort "Blutgerrinung" Lubert Stryer, Biochemie, Spektrum der Wissenschaft Verlagsgesellschaft mbH Heidelberg, 1990, p. 259.

Rompp Lexikon Chemie, Ver. 1.5, 1998, Georg Thieme Verlag Stuttgart, Stichwort "Heparin".

Ross, Russell, "Atherosclerosis—An Inflammatory Disease," The New England Journal of Medicine; vol. 340, No. 2; pp. 115-126 (Jan. 14, 1999).

Ruef, J. et al. New antithrombotic drugs on the horizon. Expert Opinion Investig. Drugs 2003, 12, 781-797.

Samama, M.L. Synthetic direct and indirect factor Xa inhibitors. Thromobis Research 2002, 106, V267-V273.

Schwartz, R., MD et al., "Neointimal Thickening AFter Severe Coronary Artery Injury Is Limited by Short-term Administration of a Factor Xa Inhibitor," Circulation, vol. 93, No. 8, Apr. 15, 1996; pp. 1542-1548.

Senden, N. et al., "Factor Xa Induces Cytokine Production and Expression of Adhesion Molecules by Human Umbilical Vein Endothelial Cells," J. Immunology, 1998, pp. 4318-4324.

Shakespeare, W.C., "Palladium-Catalyzed Coupling of Lactones with Bromobenzenes," Tetrahedron Lett. 1999, 40, 2035-2038.

Sinha, U. et al. Antithrombotic and hemostatic capacity of factor Xa versus thrombin inhibitors in models of venous and arteriovenous thrombosis. European Journal of Pharmacology 2000, 395, 51-59.

Smirnova, I. et al., "Thrombin Is an Extracellular Signal that Activates Intracellular Death Protease Pathways Inducing Apoptosis in Model Motor Neurons," J. Neurobiology, vol. 36 (1998); pp. 64-80.

Snyder, H.R. et al., "Imidazo[4,5-f]guinolines III: Antibacterial 7-Methyl-9-(substituted Arylamino)imidazo[4,5-f]guinolines," J. Pharm. Sci. 1977, 66, 1204-1206.

Stouffer, G., MD et al., "The Role of Secondary Growth Factor Production in Thrombin-Induced Proliferation of Vascular Smooth Muscle Cells," Sem. in Thrombosis and Hemostasis, vol. 24, No. 2, 1998; pp. 145-150.

Surrey et al., "The Preparation of N-Benzyl-3-morpholones and N-Benzyl-3-homomorpholones from N-(Hydroxyalkyl)-chloroacetamides," J. Amer. Chem. Soc., 77, 1955, 633-636.

Tac, K.T. et al. Factor X inhibitors. Expert Opinion Investig. Drugs 2003, 12, 799-804.

The Ephesus Study, Blood 2000, 96, 490a.

The Pentamaks Study, Blood 2000, 96, 490a-491a.

The Pentathlon 2000 Study, Blood 2000, 96, 491a.

The Penthifra Study, Blood 2000, 96, 490a.

Tong, L.K.J. et al., "The Mechanism of Dye Formation in Color Photography. VII. Intermediate Bases in the Deamination of Quinonediimines," J. Amer. Chem. Soc. 1960, 82, 1988-2001.

Tucker, J.A. et al, "Piperazinyl Oxazolidinone Antibacterial Agents Containing a Pyridine, Diazene, or Triazene Heteroaromatic Ring," J. Med. Chem. 1998, 41, 3727-3735.

Tuszynski, G. et al., "Isolation and Characterization of Antistasin," J. Biological Chem., vol. 262, No. 20, Jul. 15, 1987; pp. 9718-9723.

Tyrrell, D. et al., "Heperin in Inflammation: Potential Therapeutic Applications Beyond Anticoagulation," Advances in Pharmacology, vol. 46 (1999); pp. 151-208.

Ulllman's Encyclopedia of Industrial Chemistry, Fifth Revised Ed., Editors: Elvers, B., Hawkins, S., VCH Verlagsgesellschaft mbH, Weinheim, 19985-1996, Ch. 5, 488-506.

Uzan, A., "Antithrombotic Agents," *Emerging Drugs: The Prospect for Improved Medicines* 3: 189-208 (1998).

Watson, D. et al., "Heparin-binding Properties of the Amyloidogenic Peptides Aβ and Amylin," J. Biological Chem., vol. 272, No. 50, Dec. 12, 1997; pp. 31617-31624.

Williams, E.M. Vaughan. Classificating anti-arrhythimic drugs. In: Cardiac Arrythias-Proceedings of a symposium, sandoe E., soedertaeje: Astra (1970), pp. 449-469.

Wong et al., The Journal of Pharmacology and Experimental Therapeutics, vol. 295, No. 1 (2000) pp. 212-218.

Zhang, Y. et al., "Tissue Factor Controls the Balance of Angiogenic and Antiangiogenic Properties of Tumor Cells in Mice," J. Clin. Invest., vol. 94, Sep. 1994; pp. 1320-1327.

Zhu, B., Scarborough, R., "Recent Advances in Inhibitors of Factor Xa in the Prothrombinase Complex," *Curr. Opinions Card. Pul. Ren. Inv. Drugs*, 1:63-87 (1999).

Ziegler, C.B. et al., "Synthesis of Some Novel 7-Substituted Quinolonecarboxylic Adds via Nitroso and Nitrone Cycloadditions," J. Hetercycl. Chem. 25, 2, 1988, 719-723.

Epstein F. MD (ed.), "Atherosclerosis—An Inflammatory Disease," The New England Journal of Medicine, vol. 340, No. 2, Nov. 4, 2005, pp. 115-126.

SUBSTITUTED OXAZOLIDINONES AND THEIR USE IN THE FIELD OF BLOOD COAGULATION

CROSS-REFERENCE TO RELATED APPLICATIONS

This application is a continuation of U.S. application Ser. No. 12/494,879, filed Jun. 30, 2009, which issued on Mar. 6, 2012 as U.S. Pat. No. 8,129,378, which is hereby incorporated by reference herein in its entirety, which is a continuation of U.S. application Ser. No. 11/932,082, filed Oct. 31, 2007, which issued on Aug. 18, 2009 as U.S. Pat. No. 7,576,111, which is hereby incorporated herein by reference in its entirety, which is a continuation of U.S. application Ser. No. 11/460,529 filed Jul. 27, 2006, which issued on Sep. 22, 2009 as U.S. Pat. No. 7,592,339, which is hereby incorporated herein by reference in its entirety, which is a continuation of U.S. application Ser. No. 10/181,051 filed Jun. 24, 2002, which issued on Jan. 2, 2007 as U.S. Pat. No. 7,157,456, which is hereby incorporated herein by reference in its entirety, which is the national stage entry under 35 U.S.C. §371 of International Application No. PCT/EP00/12492, filed Dec. 11, 2000, which claims priority to German Application No. 199 62 924.2, filed Dec. 24, 1999.

FIELD OF THE INVENTION

The present invention relates to the field of blood coagulation. In particular, the present invention relates to novel oxazolidinone derivatives, to processes for their preparation and to their use as active compounds in medicaments.

BACKGROUND OF THE INVENTION

Blood coagulation is a protective mechanism of the organism which helps to "seal" defects in the wall of the blood vessels quickly and reliably. Thus, loss of blood can be avoided or kept to a minimum. Haemostasis after injury of the blood vessels is effected mainly by the coagulation system in which an enzymatic cascade of complex reactions of plasma proteins is triggered. Numerous blood coagulation factors are involved in this process, each of which factors converts, on activation, the respectively next inactive precursor into its active form. At the end of the cascade comes the conversion of soluble fibrinogen into insoluble fibrin, resulting in the formation of a blood clot. In blood coagulation, traditionally the intrinsic and the extrinsic system, which end in a joint reaction path, are distinguished. Here factor Xa, which is formed from the proenzyme factor X, plays a key role, since it connects the two coagulation paths. The activated serine protease Xa cleaves prothrombin to thrombin. The resulting thrombin, in turn, cleaves fibrinogen to fibrin, a fibrous/gelatinous coagulant. In addition, thrombin is a potent effector of platelet aggregation which likewise contributes significantly to haemostasis.

Maintenance of normal haemostasis—between bleeding and thrombosis—is subject to a complex regulatory mechanism. Uncontrolled activation of the coagulant system or defective inhibition of the activation processes may cause formation of local thrombi or embolisms in vessels (arteries, veins, lymph vessels) or in heart cavities. This may lead to serious disorders, such as myocardial infarct, angina pectoris (including unstable angina), reocclusions and restenoses after angioplasty or aortocoronary bypass, stroke, transitory ischaemic attacks, peripheral arterial occlusive disorders, pulmonary embolisms or deep venous thromboses; hereinbelow, these disorders are collectively also referred to as thromboembolic disorders. In addition, in the case of consumption coagulopathy, hypercoagulability may—systemically—result in disseminated intravascular coagulation.

These thromboembolic disorders are the most frequent cause of morbidity and mortality in most industrialized countries (Pschyrembel, Klinisches Wörterbuch [clinical dictionary], 257th edition, 1994, Walter de Gruyter Verlag, page 199 ff., entry "Blutgerinnung" [blood coagulation]; Römpp Lexikon Chemie, Version 1.5, 1998, Georg Thieme Verlag Stuttgart, entry "Blutgerinnung"; Lubert Stryer, Biochemie [biochemistry], Spektrum der Wissenschaft Verlagsgesellschaft mbH Heidelberg, 1990, page 259 ff.).

The anticoagulants, i.e. substances for inhibiting or preventing blood coagulation, which are known from the prior art have various, often grave disadvantages. Accordingly, in practice, an efficient treatment method or prophylaxis of thromboembolic disorders is very difficult and unsatisfactory.

In the therapy and prophylaxis of thromboembolic disorders, use is firstly made of heparin, which is administered parenterally or subcutaneously. Owing to more favourable pharmacokinetic properties, preference is nowadays more and more given to low-molecular-weight heparin; however, even with low-molecular-weight heparin, it is not possible to avoid the known disadvantages described below, which are involved in heparin therapy. Thus, heparin is ineffective when administered orally and has a relatively short half-life. Since heparin inhibits a plurality of factors of the blood coagulation cascade at the same time, the action is nonselective. Moreover, there is a high risk of bleeding; in particular, brain haemorrhages and gastrointestinal bleeding may occur, which may result in thrombopenia, drug-induced alopecia or osteoporosis (Pschyrembel, Klinisches Wörterbuch, 257th edition, 1994, Walter de Gruyter Verlag, page 610, entry "Heparin"; Römpp Lexikon Chemie, Version 1.5, 1998, Georg Thieme Verlag Stuttgart, entry "Heparin").

A second class of anticoagulants are the vitamin K antagonists. These include, for example, 1,3-indanediones, and especially compounds such as warfarin, phenprocoumon, dicumarol and other coumarin derivatives which inhibit the synthesis of various products of certain vitamin K-dependent coagulation factors in the liver in a non-selective manner. Owing to the mechanism of action, however, the onset of the action is very slow (latency to the onset of action 36 to 48 hours). It is possible to administer the compounds orally; however, owing to the high risk of bleeding and the narrow therapeutic index, a time-consuming individual adjustment and monitoring of the patient are required. Moreover, other adverse effects, such as gastrointestinal disturbances, hair loss and skin necroses, have been described (Pschyrembel, Klinisches Wörterbuch, 257th edition, 1994, Walter de Gruyter Verlag, page 292 ff., entry "coumarin derivatives"; Ullmann's Encyclopedia of Industrial Chemistry, 5th edition, VCH Verlagsgesellschaft, Weinheim, 1985-1996, entry "vitamin K").

Recently, a novel therapeutic approach for the treatment and prophylaxis of thromboembolic disorders has been described. This novel therapeutic approach aims to inhibit factor Xa (cf. WO-A-99/37304; WO-A-99/06371; J. Hauptmann, J. Stürzebecher, Thrombosis Research 1999, 93, 203; F. Al-Obeidi, J. A. Ostrem, Factor Xa inhibitors by classical and combinatorial chemistry, DDT 1998, 3, 223; F. Al-Obeidi, J. A. Ostrem, Factor Xa inhibitors, Exp. Opin. Ther. Patents 1999, 9, 931; B. Kaiser, Thrombin and factor Xa inhibitors, Drugs of the Future 1998, 23, 423; A. Uzan, Antithrombotic agents, Emerging Drugs 1998, 3, 189; B.-Y. Zhu, R. M. Scarborough, Curr. Opin. Card. Pulm. Ren. Inv. Drugs 1999, 1 (1), 63). It has been shown that, in animal models, various both peptidic and nonpeptidic compounds are effective as factor Xa inhibitors.

Accordingly, it is an object of the present invention to provide novel substances for controlling disorders, which substances have a wide therapeutic spectrum.

In particular, they should be suitable for a more efficient prophylaxis and/or treatment of thromboembolic disorders, avoiding—at least to some extent—the disadvantages of the prior art described above, where the term "thromboembolic disorders" in the context of the present invention is to be understood as meaning, in particular, serious disorders, such as myocardial infarct, angina pectoris (including unstable angina), reocclusions and restenoses after angioplasty or aortocoronary bypass, stroke, transitory ischaemic attacks, peripheral arterial occlusive disorders, pulmonary embolisms or deep venous thromboses.

It is another object of the present invention to provide novel anticoagulants which inhibit the blood coagulation factor Xa with increased selectivity, avoiding—at least to some extent—the problems of the therapeutic methods for thromboembolic disorders known from the prior art.

SUMMARY OF THE INVENTION

Accordingly, the present invention provides substituted oxazolidinones of the general formula (I)

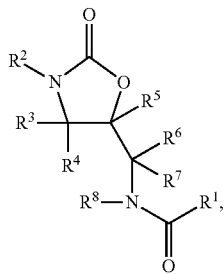

in which:
$R^1$ represents optionally benzo-fused thiophene (thienyl) which may optionally be mono- or polysubstituted;
$R^2$ represents any organic radical;
$R^3$, $R^4$, $R^5$, $R^6$, $R^7$ and $R^8$ are identical or different and each represents hydrogen or represents ($C_1$-$C_6$)-alkyl
and their pharmaceutically acceptable salts, hydrates and prodrugs,
except for compounds of the general formula (I) in which the radical $R^1$ is an unsubstituted 2-thiophene radical and the radical $R^2$ is simultaneously a mono- or polysubstituted phenyl radical and the radicals $R^3$, $R^4$, $R^5$, $R^6$, $R^7$ and $R^8$ are each simultaneously hydrogen.

Preference is given here to compounds of the general formula (I),
in which
$R^1$ represents optionally benzo-fused thiophene (thienyl) which may optionally be mono- or polysubstituted by a radical from the group consisting of halogen; cyano; nitro; amino; aminomethyl; ($C_1$-$C_8$)-alkyl which for its part may optionally be mono- or polysubstituted by halogen; ($C_3$-$C_7$)-cycloalkyl; ($C_1$-$C_8$)-alkoxy; imidazolinyl; —C(=NH)NH$_2$; carbamoyl; and mono- and di-($C_1$-$C_4$)-alkyl-aminocarbonyl, $R^2$ represents one of the groups below:
A-,
A-M-,
D-M-A-,
B-M-A-,
B—,
B-M-,
B-M-B—,
D-M-B—,
where:
the radical "A" represents ($C_6$-$C_{14}$)-aryl, preferably ($C_6$-$C_{10}$)-aryl, in particular phenyl or naphthyl, very particularly preferably phenyl;
the radical "B" represents a 5- or 6-membered aromatic heterocycle which contains up to 3 heteroatoms and/or hetero chain members, in particular up to 2 heteroatoms and/or hetero chain members, from the group consisting of S, N, NO (N-oxide) and O;
the radical "D" represents a saturated or partially unsaturated, mono- or bicyclic, optionally benzo-fused 4- to 9-memebered heterocycle which contains up to three heteroatoms and/or hetero chain members from the group consisting of S, SO, SO$_2$, N, NO (N-oxide) and O;
the radical "M" represents —NH—, —CH$_2$—, —CH$_2$CH$_2$—, —O—, —NH—CH$_2$—; —CH$_2$—NH—, —OCH$_2$—, —CH$_2$O—, —CONH—, —COO—, —OOC—, —S—, —SO$_2$— or represents a covalent bond;
where
the groups "A", "B" and "D" defined above may each optionally be mono- or polysubstituted by a radical from the group consisting of halogen; trifluoromethyl; oxo; cyano; nitro; carbamoyl; pyridyl; ($C_1$-$C_6$)-alkanoyl; ($C_3$-$C_7$)-cycloalkanoyl; ($C_6$-$C_{14}$)-arylcarbonyl; ($C_5$-$C_{10}$)-heteroarylcarbonyl; ($C_1$-$C_6$)-alkanoyloxymethyloxy; ($C_1$-$C_4$)-hydroxyalkylcarbonyl; —COOR$^{27}$; —SO$_2$R$^{27}$; —C(NR$^{27}$R$^{28}$)=NR$^{29}$; —CONR$^{28}$R$^{29}$; —SO$_2$NR$^{28}$R$^{29}$; —OR$^{30}$; —NR$^{30}$R$^{31}$, ($C_1$-$C_6$)-alkyl and ($C_3$-$C_7$)-cycloalkyl,
where ($C_1$-$C_6$)-alkyl and ($C_3$-$C_7$)-cycloalkyl for their part may optionally be substituted by a radical from the group consisting of cyano; —OR$^{27}$; —NR$^{28}$R$^{29}$; —CO(NH)$_v$(NR$^{27}$R$^{28}$) and —C(NR$^{27}$R$^{28}$)=NR$^{29}$,
where:
v is either 0 or 1 and
$R^{27}$, $R^{28}$ and $R^{29}$ are identical or different and independently of one another each represents hydrogen, ($C_1$-$C_4$)-alkyl, ($C_3$-$C_7$)-cycloalkyl, ($C_1$-$C_4$)-alkanoyl, carbamoyl, trifluoromethyl, phenyl or pyridyl,
and/or
$R^{27}$ and $R^{28}$ or $R^{27}$ and $R^{29}$ together with the nitrogen atom to which they are attached form a saturated or partially unsaturated 5- to 7-membered heterocycle having up to three, preferably up to two, identical or different heteroatoms from the group consisting of N, O and S, and
$R^{30}$ and $R^{31}$ are identical or different and independently of one another each represents hydrogen, ($C_1$-$C_4$)-alkyl, ($C_3$-$C_7$)-cycloalkyl, ($C_1$-$C_4$)-alkylsulphonyl, ($C_1$-$C_4$)-hydroxyalkyl, ($C_1$-$C_4$)-aminoalkyl, di-($C_1$-$C_4$)-alkylamino-($C_1$-$C_4$)-alkyl, —CH$_2$C(NR$^{27}$R$^{28}$)=NR$^{29}$ or —COR$^{33}$,
where
$R^{33}$ represents ($C_1$-$C_6$)-alkoxy, ($C_1$-$C_4$)-alkoxy-($C_1$-$C_4$)-alkyl, ($C_1$-$C_{14}$)-alkoxycarbonyl-($C_1$-$C_4$)- alkyl, $(C_1\text{-}C_4)$-aminoalkyl, $(C_1\text{-}C_4)$-alkoxycarbonyl, $(C_1\text{-}C_4)$-alkanoyl-$(C_1\text{-}C_4)$-alkyl, $(C_3\text{-}C_7)$-cycloalkyl, $(C_1\text{-}C_6)$-alkenyl, $(C_1\text{-}C_8)$-alkyl, which may optionally be substituted by phenyl or acetyl, $(C_6\text{-}C_{14})$-aryl, $(C_5\text{-}C_{10})$-heteroaryl, trifluoromethyl, tetrahydrofuranyl or butyrolactone, $R^3$, $R^4$, $R^5$, $R^6$, $R^7$ and $R^8$ are identical or different and each represents hydrogen or represents $(C_1\text{-}C_6)$-alkyl and their pharmaceutically acceptable salts, hydrates and prodrugs, except for compounds of the general formula (I) in which the radical $R^1$ is an unsubstituted 2-thiophene radical and the radical $R^2$ is simultaneously a mono- or polysubstituted phenyl radical and the radicals $R^3$, $R^4$, $R^5$, $R^6$, $R^7$ and $R^8$ are each simultaneously hydrogen.

Preference is also given here to compounds of the general formula (I), in which $R^1$ represents thiophene (thienyl), in particular 2-thiophene, which may optionally be mono- or polysubstituted by halogen, preferably chlorine or bromine, by amino, aminomethyl or $(C_1\text{-}C_8)$-alkyl, preferably methyl, where the $(C_1\text{-}C_8)$-alkyl radical for its part may optionally be mono- or polysubstituted by halogen, preferably fluorine, $R^2$ represents one of the groups below:

A-,
A-M-,
D-M-A-,
B-M-A-,
B—,
B-M-,
B-M-B—,
D-M-B—, where:

the radical "A" represents $(C_6\text{-}C_{14})$-aryl, preferably $(C_6\text{-}C_{10})$-aryl, in particular phenyl or naphthyl, very particularly preferably phenyl; the radical "B" represents a 5- or 6-membered aromatic heterocycle which contains up to 3 heteroatoms and/or hetero chain members, in particular up to 2 heteroatoms and/or hetero chain members, from the group consisting of S, N, NO (N-oxide) and O;

the radical "D" represents a saturated or partially unsaturated 4- to 7-membered heterocycle which contains up to three heteroatoms and/or hetero chain members from the group consisting of S, SO, $SO_2$, N, NO (N-oxide) and O;

the radical "M" represents —NH—, —$CH_2$—, —$CH_2CH_2$—, —O—, —NH—$CH_2$—, $CH_2$—NH—, —$OCH_2$—, —$CH_2O$—, —CONH—, —NHCO—, —COO—, —OOC—, —S— or represents a covalent bond;

where the groups "A", "B" and "D" defined above may in each case optionally be mono- or polysubstituted by a radical from the group consisting of halogen; trifluoromethyl; oxo; cyano; nitro; carbamoyl; pyridyl; $(C_1\text{-}C_6)$-alkanoyl; $(C_3\text{-}C_7)$-cycloalkanoyl; $(C_6\text{-}C_{14})$-arylcarbonyl; $(C_5\text{-}C_{10})$-heteroarylcarbonyl; $(C_1\text{-}C_6)$-alkanoyloxymethyloxy; —$COOR^{27}$; —$SO_2R^{27}$; —$C(NR^{27}R^{28})\!=\!\!NR^{29}$; —$CONR^{28}R^{29}$; —$SO_2NR^{28}R^{29}$; —$OR^{30}$; —$NR^{30}R^{31}$, $(C_1\text{-}C_6)$-alkyl and $C_3\text{-}C_7)$-cycloalkyl, where $(C_1\text{-}C_6)$-alkyl and $(C_3\text{-}C_7)$-cycloalkyl for their part may optionally be substituted by a radical from the group consisting of cyano; —$OR^{27}$; —$NR^{28}R^{29}$; —$CO(NH)_v(NR^{27}R^{28})$ and —$C(NR^{27}R^{28})\!=\!\!NR^{29}$, where:

v is either 0 or 1 and $R^{27}$, $R^{28}$ and $R^{29}$ are identical or different and independently of one another each represents hydrogen, $(C_1\text{-}C_4)$-alkyl or $(C_3\text{-}C_7)$-cycloalkyl, and/or $R^{27}$ and $R^{28}$ or $R^{27}$ and $R^{29}$ together with the nitrogen atom to which they are attached form a saturated or partially unsaturated 5- to 7-membered heterocycle having up to three, preferably up to two, identical or different heteroatoms from the group consisting of N, O and S, and $R^{30}$ and $R^{31}$ are identical or different and independently of one another each represents hydrogen, $(C_1\text{-}C_4)$-alkyl, $(C_3\text{-}C_7)$-cycloalkyl, $(C_1\text{-}C_4)$-alkylsulphonyl, $(C_1\text{-}C_4)$-hydroxyalkyl, $(C_1\text{-}C_4)$-aminoalkyl, di-$(C_1\text{-}C_4)$-alkylamino-$(C_1\text{-}C_4)$-alkyl, $(C_1\text{-}C_4)$-alkanoyl, $(C_6\text{-}C_{14})$-arylcarbonyl, $(C_5\text{-}C_{10})$-heteroarylcarbonyl, $(C_1\text{-}C_4)$-alkylaminocarbonyl or —$CH_2C(NR^{27}R^{28})\!=\!\!NR^{29}$, $R^3$, $R^4$, $R^5$, $R^6$, $R^7$ and $R^8$ are identical or different and each represents hydrogen or represents $(C_1\text{-}C_6)$-alkyl and their pharmaceutically acceptable salts, hydrates and prodrugs, except for compounds of the general formula (I) in which the radical $R^1$ is an unsubstituted 2-thiophene radical and the radical $R^2$ is simultaneously a mono- or polysubstituted phenyl radical and the radicals $R^3$, $R^4$, $R^5$, $R^6$, $R^7$ and $R^8$ are each simultaneously hydrogen.

Particular preference is given here to compounds of the general formula (I), in which $R^1$ represents thiophene (thienyl), in particular 2-thiophene, which may optionally be mono- or polysubstituted by halogen, preferably chlorine or bromine, or by $(C_1\text{-}C_8)$-alkyl, preferably methyl, where the $(C_1\text{-}C_8)$-alkyl radical for its part may optionally be mono- or polysubstituted by halogen, preferably fluorine, $R^2$ represents one of the groups below:

A-,
A-M-,
D-M-A-,
B-M-A-,
B—,
B-M-,
B-M-B—,
D-M-B—, where:

the radical "A" represents phenyl or naphthyl, in particular phenyl; the radical "B" represents a 5- or 6-membered aromatic heterocycle which contains up to 2 heteroatoms from the group consisting of S, N, NO (N-oxide) and O;

the radical "D" represents a saturated or partially unsaturated 5- or 6-membered heterocycle which contains up to two heteroatoms and/or hetero chain members from the group consisting of S, SO, $SO_2$, N, NO (N-oxide) and O;

the radical "M" represents —NH—, —O—, —NH—$CH_2$—, —$CH_2$—NH—, —$OCH_2$—, —$CH_2O$—, —CONH—, —NHCO— or represents a covalent bond;

where the groups "A", "B" and "D" defined above may in each case optionally be mono- or polysubstituted by a radical from the group consisting of halogen; trifluoromethyl; oxo; cyano; pyridyl; ($C_1$-$C_3$)-alkanoyl; ($C_6$-$C_{10}$)-arylcarbonyl; ($C_5$-$C_6$)-heteroarylcarbonyl; ($C_1$-$C_3$)-alkanoyloxymethyloxy; —C($NR^{27}R^{28}$)=$NR^{29}$; —CO$NR^{28}R^{29}$; —SO$_2NR^{28}R^{29}$; —OH; —$NR^{30}R^{31}$; ($C_1$-$C_4$)-alkyl; and cyclopropyl, cyclopentyl or cyclohexyl, where ($C_1$-$C_4$)-alkyl and cyclopropyl, cyclopentyl or cyclohexyl for their part may optionally be substituted by a radical from the group consisting of cyano; —OH; —OCH$_3$; —$NR^{28}R^{29}$; —CO(NH)$_v$($NR^{27}R^{28}$) and —C($NR^{27}R^{28}$)=$NR^{29}$;

where:

v is either 0 or 1, preferably 0, and $R^{27}$, $R^{28}$ and $R^{29}$ are identical or different and independently of one another each represents hydrogen, ($C_1$-$C_4$)-alkyl or else cyclopropyl, cyclopentyl or cyclohexyl and/or $R^{27}$ and $R^{28}$ or $R^{27}$ and $R^{29}$ together with the nitrogen atom to which they are attached may form a saturated or partially unsaturated 5- to 7-membered heterocycle having up to two identical or different heteroatoms from the group consisting of N, O and S, and $R^{30}$ and $R^{31}$ are identical or different and independently of one another each represents hydrogen, ($C_1$-$C_4$)-alkyl, cyclopropyl, cyclopentyl, cyclohexyl, ($C_1$-$C_4$)-alkylsulphonyl, ($C_1$-$C_4$)-hydroxyalkyl, ($C_1$-$C_4$)-aminoalkyl, di-($C_1$-$C_4$)-alkylamino-($C_1$-$C_4$)-alkyl, ($C_1$-$C_3$)-alkanoyl or phenylcarbonyl, $R^3$, $R^4$, $R^5$, $R^6$, $R^7$ and $R^8$ are identical or different and each represents hydrogen or represents ($C_1$-$C_6$)-alkyl and their pharmaceutically acceptable salts, hydrates and prodrugs, except for compounds of the general formula (I) in which the radical $R^1$ is an unsubstituted 2-thiophene radical and the radical $R^2$ is simultaneously a mono- or polysubstituted phenyl radical and the radicals $R^3$, $R^4$, $R^5$, $R^6$, $R^7$ and $R^8$ are each simultaneously hydrogen.

Particular preference is given here to compounds of the general formula (I), in which $R^1$ represents 2-thiophene which may optionally be substituted in the 5-position by a radical from the group consisting of chlorine, bromine, methyl or trifluoromethyl, $R^2$ represents one of the groups below:

A-,
A-M-,
D-M-A-,
B-M-A-,
B—,
B-M-,
B-M-B—,
D-M-B—, where:

the radical "A" represents phenyl or naphthyl, in particular phenyl; the radical "B" represents a 5- or 6-membered aromatic heterocycle which contains up to 2 heteroatoms from the group consisting of S, N, NO (N-oxide) and O;

the radical "D" represents a saturated or partially unsaturated 5- or 6-membered heterocycle which contains a nitrogen atom and optionally a further heteroatom and/or hetero chain member from the group consisting of S, SO, SO$_2$ and O; or contains up to two heteroatoms and/or hetero chain members from the group consisting of S, SO, SO$_2$ and O;

the radical "M" represents —NH—, —O—, —NH—CH$_2$—, —CH$_2$—NH—, —OCH$_2$—, —CH$_2$O—, —CONH—, —NHCO— or represents a covalent bond;

where the groups "A", "B" and "D" defined above may in each case optionally be mono- or polysubstituted by a radical from the group consisting of halogen; trifluoromethyl; oxo; cyano; pyridyl; ($C_1$-$C_3$)-alkanoyl; ($C_6$-$C_{10}$)-arylcarbonyl; ($C_5$-$C_6$)-heteroarylcarbonyl; ($C_1$-$C_3$)-alkanoyloxymethyloxy; —CO$NR^{28}R^{29}$; —SO$_2NR^{28}R^{29}$; —OH; —$NR^{30}R^{31}$; ($C_1$-$C_4$)-alkyl; and cyclopropyl, cyclopentyl or cyclohexyl, where ($C_1$-$C_4$)-alkyl and cyclopropyl, cyclopentyl or cyclohexyl for their part may optionally be substituted by a radical from the group consisting of cyano; —OH; —OCH$_3$; —$NR^{28}R^{29}$; —CO(NH)$_v$($NR^{27}R^{28}$) and —C($NR^{27}R^{28}$)=$NR^{29}$, where:

v is either 0 or 1, preferably 0, and $R^{27}$, $R^{28}$ and $R^{29}$ are identical or different and independently of one another each represents hydrogen, ($C_1$-$C_4$)-alkyl or else cyclopropyl, cyclopentyl or cyclohexyl and/or $R^{27}$ and $R^{28}$ or $R^{27}$ and $R^{29}$ together with the nitrogen atom to which they are attached may form a saturated or partially unsaturated 5- to 7-membered heterocycle having up to two identical or different heteroatoms from the group consisting of N, O and S, and $R^{30}$ and $R^{31}$ are identical or different and independently of one another each represents hydrogen, ($C_1$-$C_4$)-alkyl, cyclopropyl, cyclopentyl, cyclohexyl, ($C_1$-$C_4$)-alkylsulphonyl, ($C_1$-$C_{14}$)-hydroxyalkyl, ($C_1$-$C_4$)-aminoalkyl, di-($C_1$-$C_4$)-alkylamino-($C_1$-$C_4$)-alkyl, ($C_1$-$C_3$)-alkanoyl or phenylcarbonyl, $R^3$, $R^4$, $R^5$, $R^6$, $R^7$ and $R^8$ are identical or different and each represents hydrogen or represents ($C_1$-$C_4$)-alkyl and their pharmaceutically acceptable salts, hydrates and prodrugs, except for compounds of the general formula (I) in which the radical $R^1$ is an unsubstituted 2-thiophene radical and the radical $R^2$ is simultaneously a mono- or polysubstituted phenyl radical and the radicals $R^3$, $R^4$, $R^5$, $R^6$, $R^7$ and $R^8$ are each simultaneously hydrogen.

Very particular preference is given here to compounds of the general formula (I), in which $R^1$ represents 2-thiophene which is substituted in the 5-position by a radical from the group consisting of chlorine, bromine, methyl and trifluoromethyl, $R^2$ represents D-A-:

where:

the radical "A" represents phenylene;

the radical "D" represents a saturated 5- or 6-membered heterocycle, which is attached to "A" via a nitrogen atom, which has a carbonyl group directly adjacent to the linking nitrogen atom and in which one carbon ring member may be replaced by a heteroatom from the group consisting of S, N and O;

where the group "A" defined above may optionally be mono- or disubstituted in the meta position with respect to the point of attachment to the oxazolidinone, by a radical from the group consisting of fluorine, chlorine, nitro, amino, trifluoromethyl, methyl and cyano, $R^3$, $R^4$, $R^5$, $R^6$, $R^7$ and $R^8$ each represent hydrogen and their pharmaceutically acceptable salts, hydrates and prodrugs.

Very particular preference is also given here to the compound having the following formula

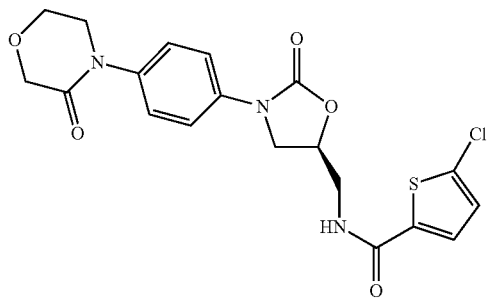 [SMILES: O=C(NC[C@H]1CN(c2ccc(N3CCOCC3=O)cc2)C(=O)O1)c1ccc(Cl)s1]

and to its pharmaceutically acceptable salts, hydrates and prodrugs.

In the compounds of the general formula (I) above, the radical $R^1$ may in particular represent optionally benzo-fused thiophene (thienyl) which may optionally be mono- or polysubstituted by a radical from the group consisting of halogen; cyano; nitro; $(C_1-C_8)$-alkyl, which for its part may optionally be mono- or polysubstituted by halogen; $(C_3-C_7)$-cycloalkyl; $(C_1-C_8)$-alkoxy; imidazolinyl; —C(=NH)NH$_2$; carbamoyl; and mono- and di-$(C_1-C_4)$-alkylaminocarbonyl.

In the compounds of the general formula (I), the radical $R^1$ may preferably represent thiophene (thienyl), in particular 2-thiophene, which may optionally be mono- or polysubstituted by halogen, preferably chlorine or bromine, or by $(C_1-C_8)$-alkyl, preferably methyl, where the $(C_1-C_8)$-alkyl radical, preferably the methyl radical, may for its part optionally be mono- or polysubstituted by halogen, preferably fluorine.

In the compounds of the general formula (I), the radicals $R^3$, $R^4$, $R^5$, $R^6$, $R^7$ and $R^8$ may be identical or different and may represent, in particular, hydrogen or $(C_1-C_6)$-alkyl, preferably hydrogen or $(C_1-C_4)$-alkyl, very particularly preferably hydrogen.

The radical $R^2$, i.e. the organic radical, can in particular be selected from the substituent groups listed below:

In the compounds of the general formula (I), the radical $R^2$ may, in particular, represent a group of the following formula:

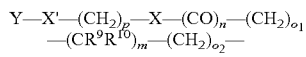

where:
m is an integer from 0 to 6, preferably from 1 to 3,
n is either 0 or 1,
p is an integer from 0 to 3, preferably either 0 or 1,
$o_1$ is an integer 0 or 1,
$o_2$ is an integer 0 or 1,
$R^9$ and $R^{10}$ are identical or different and each represents hydrogen; $(C_1-C_4)$-alkyl, preferably methyl; $(C_1-C_4)$-alkoxy, preferably methoxy; $(C_3-C_7)$-cycloalkyl; hydroxyl or fluorine,
X and X' are identical or different and each represents O; N—$R^{11}$ or a covalent bond, where $R^{11}$ represents H; $(C_1-C_4)$-alkyl, preferably methyl, or $(C_3-C_7)$-cycloalkyl, Y represents a 3- to 7-membered saturated or partially unsaturated cyclic hydrocarbon radical which optionally contains 1 to 3 identical or different heteroatoms and/or hetero chain members from the group consisting of N, O, S, SO and SO$_2$, where:
this radical Y may optionally be substituted by a 5- or 6-membered aromatic or a 3- to 7-membered saturated or partially unsaturated cyclic hydrocarbon radical which optionally contains up to 3 identical or different heteroatoms from the group consisting of N, O and S and where this radical may for its part optionally be substituted by a radical from the group consisting of cyano; hydroxyl; halogen; $(C_1-C_4)$-alkyl; —C(NR$^{12}$)NR$^{13}$R$^{13'}$; and —NR$^{14}$R$^{15}$, where:
$R^{12}$ represents hydrogen, $(C_1-C_4)$-alkyl or $(C_3-C_7)$-cycloalkyl;
$R^{13}$ and $R^{13'}$ are identical or different and independently of one another each represents hydrogen, $(C_1-C_4)$-alkyl or $(C_3-C_7)$-cycloalkyl
and/or
$R^{13}$ and $R^{13'}$ together with the N atom to which they are attached form a 5- to 7-membered heterocycle which may optionally contain up to 2 further heteroatoms from the group consisting of N, O and S;
$R^{14}$ and $R^{15}$ are identical or different and independently of one another each represents hydrogen, $(C_1-C_4)$-alkyl, $(C_3-C_7)$-cycloalkyl or $(C_1-C_5)$-alkanoyl;
and/or
this radical Y may furthermore optionally be substituted by a radical from the group consisting of oxo; cyano; thiono; halogen; —OR$^{16}$; =NR$^{16}$; —NR$^{16}$R$^{17}$; —C(=NR$^{18}$)NR$^{19}$R$^{19'}$ and $(C_1-C_4)$-alkyl,
in which $(C_1-C_4)$-alkyl for its part may optionally be substituted by a radical from the group consisting of hydroxyl; cyano; —NR$^{16}$R$^{17}$ and —C(=NR$^{18}$)NR$^{19}$R$^{19'}$,
where:
$R^{16}$ and $R^{17}$ are identical or different and independently of one another each represents hydrogen, $(C_1-C_4)$-alkyl, $(C_3-C_7)$-cycloalkyl or $(C_1-C_3)$-alkanoyl;
$R^{18}$ represents hydrogen, $(C_1-C_4)$-alkyl or $(C_3-C_7)$-cycloalkyl;
$R^{19}$ and $R^{19'}$ are identical or different and independently of one another each represents hydrogen, $(C_1-C_4)$-alkyl or $(C_3-C_7)$-cycloalkyl
and/or
$R^{19}$ and $R^{19'}$ together with the N atom to which they are attached form a 5- to 7-membered heterocycle which may optionally contain up to 2 further heteroatoms from the group consisting of N, O and S.

Particular preference is given to compounds of the general formula (I) in which the radical $R^2$ represents a group of the following formula:

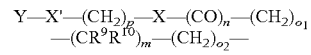

where
m is an integer from 0 to 3,
n is an integer 0 or 1,
p is an integer 0 or 1, $o_1$ is an integer 0 or 1,
$o_2$ is an integer 0 or 1,
$R^9$ and $R^{10}$ are identical or different and each represents hydrogen; methyl; methoxy; hydroxyl or fluorine,
X and X' are identical or different and each represents O; N—$R^{11}$ or a covalent bond,
  where $R^{11}$ represents H or methyl,
Y represents a 5- to 7-membered saturated cyclic hydrocarbon radical which optionally contains 1 or 2 identical or different heteroatoms and/or hetero chain members from the group consisting of N, O, S, SO and $SO_2$, in particular cyclohexyl, piperazinyl, morpholinyl, thiomorpholinyl, diazepinyl, pyrrolidinyl and piperidinyl,
  where:
    this radical Y may optionally be substituted by a 5- or 6-membered aromatic or a 5- to 7-membered saturated or partially unsaturated cyclic hydrocarbon radical which optionally contains up to 2 identical or different heteroatoms from the group consisting of N, O and S and
    where this radical for its part may be substituted by a radical from the group consisting of cyano; hydroxyl; fluorine; chlorine; ($C_1$-$C_4$)-alkyl; —C(=$NR^{12}$)$NR^{13}R^{13'}$; and —$NR^{14}R^{15}$,
    where:
      $R^{12}$ represents hydrogen, methyl, ethyl, cyclopropyl, cyclopentyl or cyclohexyl;
      $R^{13}$ and $R^{13'}$ are identical or different and independently of one another each represents hydrogen, methyl, ethyl, cyclopropyl, cyclopentyl or cyclohexyl
      and/or
      $R^{13}$ and $R^{13'}$ together with the N atom to which they are attached form a 5- to 7-membered heterocycle which may optionally contain up to 2 further heteroatoms from the group consisting of N, O and S, in particular piperidinyl, piperazinyl, morpholinyl and thiomorpholinyl;
      $R^{14}$ and $R^{15}$ are identical or different and independently of one another each represents hydrogen, methyl, ethyl, cyclopropyl, cyclopentyl or cyclohexyl or else acetyl;
    and/or
    this radical Y may furthermore optionally be substituted by a radical from the group consisting of oxo; cyano; thiono; fluorine; chlorine; —OH; —$OCH_3$; =$NR^{16}$; —$NH_2$; —$N(CH_3)_2$; —C(=$NR^{18}$)$NR^{19}R^{19'}$ and methyl,
    in which methyl for its part may optionally be substituted by a radical from the group consisting of hydroxyl; cyano; —$NR^{16}R^{17}$ and —C(=$NR^{18}$)$NR^{19}R^{19'}$,
    where:
      $R^{16}$ and $R^{17}$ are identical or different and independently of one another each represents hydrogen, methyl, ($C_3$-$C_7$)-cycloalkyl or acetyl;
      $R^{18}$ represents hydrogen, methyl or ($C_3$-$C_7$)-cycloalkyl;
      $R^{19}$ and $R^{19'}$ are identical or different and independently of one another each represents hydrogen, methyl or ($C_3$-$C_7$)-cycloalkyl
      and/or
      $R^{19}$ and $R^{19'}$ together with the N atom to which are attached form a 5- to 7-membered heterocycle which may optionally contain up to 2 further heteroatoms from the group consisting of N, O and S, in particular piperidinyl, piperazinyl, morpholinyl and thiomorpholinyl.

Likewise, in the compounds of the general formula (I), the radical
$R^2$ may represent a group of the formula below:

$$Z-(CO)_t-(CR^{20}R^{21})_s-$$

where:
s is an integer from 1 to 6,
t is either 0 or 1,
$R^{20}$ and $R^{21}$ are identical or different and each represents hydrogen, ($C_1$-$C_4$)-alkyl, ($C_1$-$C_4$)-alkoxy, ($C_3$-$C_7$)-cycloalkyl, hydroxyl or fluorine,
Z represents a radical which is selected from the group consisting of cyano; —C($NR^{22}R^{23}$)=$NR^{24}$; —CO(NH)$_u NR^{22}R^{23}$; and —$NR^{25}R^{26}$,
  where:
    u is either 0 or 1, preferably 0, and
    $R^{22}$, $R^{23}$ and $R^{24}$ are identical or different and independently of one another each represents hydrogen, ($C_1$-$C_4$)-alkyl or ($C_3$-$C_7$)-cycloalkyl, preferably hydrogen or methyl,
    and/or
    $R^{22}$ and $R^{23}$ together with the N atom to which they are attached form a 5- to 7-membered heterocycle which may optionally contain up to 2 further heteroatoms and/or hetero chain members from the group consisting of N, O, S, SO and $SO_2$;
    $R^{25}$ and $R^{26}$ are identical or different and independently of one another each represents hydrogen, ($C_1$-$C_4$)-alkyl or ($C_3$-$C_7$)-cycloalkyl, preferably hydrogen, methyl or ethyl, where ($C_1$-$C_4$)-alkyl and ($C_3$-$C_7$)-cycloalkyl for their part may optionally be substituted by hydroxyl or ($C_1$-$C_6$)-alkoxy.

Furthermore, in the compounds of the general formula (I), the radical
$R^2$ may represent one of the following groups:
A-,
A-M-,
D-M-A-,
B-M-A-,
B—,
B-M-,
B-M-B—,
D-M-B—,
where:
the radical "A" represents ($C_6$-$C_{14}$)-aryl, preferably ($C_6$-$C_{10}$)-aryl, in particular phenyl or naphthyl, very particularly preferably phenyl;
the radical "B" represents a 5- or 6-membered aromatic heterocycle which contains up to 3 heteroatoms and/or hetero chain members, in particular up to 2 heteroatoms and/or hetero chain members, from the group consisting of S, N, NO (N-oxide) and O;
the radical "D" represents a saturated or partially unsaturated 4- to 7-membered heterocycle which contains up to three heteroatoms and/or hetero chain members from the group consisting of S, SO, $SO_2$, N, NO (N-oxide) and O;
the radical "M" represents —NH—, —$CH_2$—, —$CH_2CH_2$—, —O—, —NH—$CH_2$—, —$CH_2$—NH—, —$OCH_2$—, —$CH_2O$—, —CONH—, —NHCO—, —COO—, —OOC—, —S— or represents a covalent bond;
where
the groups "A", "B" and "D" defined above may in each case optionally be mono- or polysubstituted by a radical from the group consisting of halogen; trifluoromethyl; oxo; cyano; nitro; carbamoyl; pyridyl; ($C_1$-$C_6$)-alkanoyl; ($C_3$-$C_7$)-cycloalkanoyl; ($C_6$-$C_{14}$)-arylcarbonyl;

($C_5$-$C_{10}$)-heteroarylcarbonyl; ($C_1$-$C_6$)-alkanoyloxymethyloxy; —COOR$^{27}$; —SO$_2$R$^{27}$; —C(NR$^{27}$R$^{28}$)=NR$^{29}$; —CONR$^{28}$R$^{29}$; —SO$_2$NR$^{28}$R$^{29}$; —OR$^{30}$; —NR$^{30}$R$^{31}$, ($C_1$-$C_6$)-alkyl and ($C_3$-$C_7$)-cycloalkyl, where ($C_1$-$C_6$)-alkyl and ($C_3$-$C_7$)-cycloalkyl for their part may optionally be substituted by a radical from the group consisting of cyano; —OR$^{27}$; —NR$^{28}$R$^{29}$; —CO(NH)$_v$(NR$^{27}$R$^{28}$) and —C(NR$^{27}$R$^{28}$)=NR$^{29}$, where:

v is either 0 or 1 and

R$^{27}$, R$^{28}$ and R$^{29}$ are identical or different and independently of one another each represents hydrogen, ($C_1$-$C_4$)-alkyl or ($C_3$-$C_7$)-cycloalkyl and/or R$^{27}$ and R$^{28}$ or R$^{27}$ and R$^{29}$ together with the nitrogen atom to which they are attached form a saturated or partially unsaturated 5- to 7-membered heterocycle having up to three, preferably up to two, identical or different heteroatoms from the group consisting of N, O and S, and R$^{30}$ and R$^{31}$ are identical or different and independently of one another each represents hydrogen, ($C_1$-$C_4$)-alkyl, ($C_3$-$C_7$)-cycloalkyl, ($C_1$-$C_4$)-alkylsulphonyl, ($C_1$-$C_4$)-hydroxyalkyl, ($C_1$-$C_4$)-aminoalkyl, di-($C_1$-$C_4$)-alkylamino-($C_1$-$C_4$)-alkyl, ($C_1$-$C_4$)-alkanoyl, ($C_6$-$C_{14}$)-arylcarbonyl, ($C_5$-$C_{10}$)-heterarylcarbonyl, ($C_1$-$C_4$)-alkylaminocarbonyl or —CH$_2$C(NR$^{27}$R$^{28}$)=NR$^{29}$.

Preference is also given to compounds of the general formula (I) in which the radical R$^2$ represents one of the groups below:

A-,

A-M-,

D-M-A-,

B-M-A-,

B—,

B-M-,

B-M-B—,

D-M-B—, where:

the radical "A" represents phenyl or naphthyl, in particular phenyl;

the radical "B" represents a 5- or 6-membered aromatic heterocycle which contains up to 2 heteroatoms from the group consisting of S, N, NO (N-oxide) and O;

the radical "D" represents a saturated or partially unsaturated 5- or 6-membered heterocycle which contains up to two heteroatoms and/or hetero chain members from the group consisting of S, SO, SO$_2$, N, NO (N-oxide) and O;

the radical "M" represents —NH—, —O—, —NH—CH$_2$—, —CH$_2$—NH—, —OCH$_2$—, —CH$_2$O—, —CONH—, —NHCO— or represents a covalent bond;

where the groups "A", "B" and "D" defined above may in each case optionally be mono- or polysubstituted by a radical from the group consisting of halogen; trifluoromethyl; oxo; cyano; pyridyl; ($C_1$-$C_3$)-alkanoyl; ($C_6$-$C_{10}$)-arylcarbonyl; ($C_5$-$C_6$)-hetero arylcarbonyl; ($C_1$-$C_3$)-alkanoyloxymethyloxy; —C(NR$^{27}$R$^{28}$)=NR$^{29}$; —CONR$^{28}$R$^{29}$; —SO$_2$NR$^{28}$R$^{29}$; —OH; —NR$^{30}$R$^{31}$; ($C_1$-$C_4$)-alkyl; and cyclopropyl, cyclopentyl or cyclohexyl, where ($C_1$-$C_4$)-alkyl and cyclopropyl, cyclopentyl or cyclohexyl for their part may optionally be substituted by a radical from the group consisting of cyano; —OH; —OCH$_3$; —NR$^{28}$R$^{19}$; —CO(NH)$_v$(NR$^{27}$R$^{28}$) and —C(NR$^{27}$R$^{28}$)=NR$^{29}$, where:

v is either 0 or 1, preferably 0, and

R$^{27}$, R$^{28}$ and R$^{29}$ are identical or different and independently of one another each represents hydrogen, ($C_1$-$C_4$)-alkyl or else cyclopropyl, cyclopentyl or cyclohexyl and/or R$^{27}$ and R$^{28}$ or R$^{27}$ and R$^{29}$ together with the nitrogen atom to which they are attached may form a saturated or partially unsaturated 5- to 7-membered heterocycle having up to two identical or different heteroatoms from the group consisting of N, O and S, and R$^{30}$ and R$^{31}$ are identical or different and independently of one another each represents hydrogen, ($C_1$-$C_4$)-alkyl, cyclopropyl, cyclopentyl, cyclohexyl, ($C_1$-$C_4$)-alkylsulphonyl, ($C_1$-$C_4$)-hydroxyalkyl, ($C_1$-$C_4$)-aminoalkyl, di-($C_1$-$C_4$)-alkylamino-($C_1$-$C_4$)-alkyl, ($C_1$-$C_3$)-alkanoyl or phenylcarbonyl.

Likewise, in the compounds of the general formula (I), the radical

R$^2$ may represent a group of the following formula:

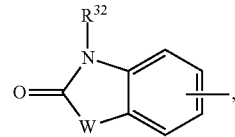

where

R$^{32}$ represents hydrogen or ($C_1$-$C_4$)-alkyl, preferably hydrogen or methyl, and W represents S, NH or O, preferably S.

Moreover, in the compounds of the general formula (I), the radical

R$^2$ may be a group of the formula below

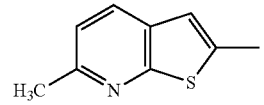

Finally, in the compounds of the general formula (I), the radical

R$^2$ may be a group of the formula below

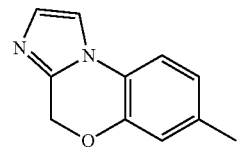

DETAILED DESCRIPTION

To date, oxazolidinones have essentially only been described as antibiotics, and in individual cases also as MAO inhibitors and fibrinogen antagonists (review: Riedl, B., Endermann, R., Exp. Opin. Ther. Patents 1999, 9 (5), 625), where a small 5-[acylaminomethyl] group (preferably 5-[acetylaminomethyl]) appears to be essential for the antibacterial activity.

Substituted aryl- and heteroarylphenyloxazolidinones in which a mono- or polysubstituted phenyl radical may be attached to the N atom of the oxazolidinone ring and which may have an unsubstituted N-methyl-2-thiophenecarboxamide radical in the 5-position of the oxazolidinone ring, and their use as antibacterial substances, are known from U.S. Pat. No. 5,929,248, U.S. Pat. No. 5,801,246, U.S. Pat. No. 5,756,732, U.S. Pat. No. 5,654,435, U.S. Pat. No. 5,654,428 and U.S. Pat. No. 5,565,571.

In addition, benzamidine-containing oxazolidinones are known as synthetic intermediates in the synthesis of factor Xa inhibitors and/or fibrinogen antagonists (WO-A-99/31092, EP-A-623615).

Depending on the substitution pattern, the compounds of the general formula (I) according to the invention may exist in stereoisomeric forms which are either like image and mirror image (enantiomers) or not like image and mirror image (diastereomers). The invention relates both to the enantiomers or diastereomers and to their respective mixtures. The racemic forms, like the diastereomers, can be separated in a known manner into the stereoisomerically uniform components.

Furthermore, certain compounds of the general formula (I) can be present in tautomeric forms. This is known to the person skilled in the art, and such compounds are likewise within the scope of the invention.

Physiologically acceptable, i.e. pharmaceutically compatible, salts can be salts of the compounds according to the invention with inorganic or organic acids. Preference is given to salts with inorganic acids, such as, for example, hydrochloric acid, hydrobromic acid, phosphoric acid or sulphuric acid, or to salts with organic carboxylic or sulphonic acids, such as, for example, acetic acid, trifluoroacetic acid, propionic acid, maleic acid, fumaric acid, malic acid, citric acid, tartaric acid, lactic acid, benzoic acid, or methanesulphonic acid, ethanesulphonic acid, benzenesulphonic acid, toluenesulphonic acid or naphthalenedisulphonic acid.

Other pharmaceutically compatible salts which may be mentioned are salts with customary bases, such as, for example, alkali metal salts (for example sodium or potassium salts), alkaline earth metal salts (for example calcium or magnesium salts) or ammonium salts, derived from ammonia or organic amines, such as, for example, diethylamine, triethylamine, ethyldiisopropylamine, procaine, dibenzylamine, N-methylmorpholine, dihydroabietylamine or methylpiperidine.

According to the invention, "hydrates" are forms of the compounds of the general formula (I) above which form a molecule compound (solvate) in the solid or liquid state by hydration with water. In the hydrates, the water molecules are attached through secondary valencies by intermolecular forces, in particular hydrogen bridges. Solid hydrates contain water as so-called crystal water in stoichiometric ratios, where the water molecules do not have to be equivalent with respect to their binding state. Examples of hydrates are sesquihydrates, monohydrates, dihydrates or trihydrates. Equally suitable are the hydrates of salts of the compounds according to the invention.

According to the invention, "prodrugs" are forms of the compounds of the general formula (I) above which for their part can be biologically active or inactive, but which can be converted into the corresponding biologically active form (for example metabolically, solvolytically or in another way).

Halogen represents fluorine, chlorine, bromine and iodine. Preference is given to chlorine or fluorine.

$(C_1-C_8)$-Alkyl represents a straight-chain or branched alkyl radical having 1 to 8 carbon atoms. Examples which may be mentioned are: methyl, ethyl, n-propyl, isopropyl, n-butyl, isobutyl, tert-butyl, n-pentyl and n-hexyl. The corresponding alkyl groups with fewer carbon atoms, such as, for example, $(C_1-C_6)$-alkyl and $(C_1-C_4)$-alkyl, are derived analogously from this definition. In general, preference is given to $(C_1-C_4)$-alkyl.

The meaning of the corresponding component of other more complex substituents, such as, for example, alkylsulphonyl, hydroxyalkyl, hydroxyalkylcarbonyl, alkoxyalkyl, alkoxycarbonyl-alkyl, alkanoylalkyl, aminoalkyl or alkylaminoalkyl is likewise derived from this definition.

$(C_3-C_7)$-Cycloalkyl represents a cyclic alkyl radical having 3 to 7 carbon atoms. Examples which may be mentioned are: cyclopropyl, cyclobutyl, cyclopentyl, cyclohexyl or cycloheptyl. The corresponding cycloalkyl groups having fewer carbon atoms, such as, for example, $(C_3-C_5)$-cycloalkyl, are derived analogously from this definition. Preference is given to cyclopropyl, cyclopentyl and cyclohexyl.

The meaning of the corresponding component of other more complex substituents, such as, for example, cycloalkanoyl, is likewise derived from this definition.

In the context of the invention, $(C_7-C_6)$-alkenyl represents a straight-chain or branched alkenyl radical having 2 to 6 carbon atoms. Preference is given to a straight-chain or branched alkenyl radical having 2 to 4 carbon atoms. Examples which may be mentioned are: vinyl, allyl, isopropenyl and n-but-2-en-1-yl.

$(C_1-C_8)$-Alkoxy represents a straight-chain or branched alkoxy radical having 1 to 8 carbon atoms. Examples which may be mentioned are: methoxy, ethoxy, n-propoxy, isopropoxy, n-butoxy, isobutoxy, tert-butoxy, n-pentoxy, n-hexoxy, n-heptoxy and n-octoxy. The corresponding alkoxy groups having fewer carbon atoms, such as, for example, $(C_1-C_6)$-alkoxy and $(C_1-C_4)$-Alkoxy, are derived analogously from this definition. In general, preference is given to $(C_1-C_4)$-alkoxy.

The meaning of the corresponding component of other more complex substituents, such as, for example alkoxyalkyl, alkoxycarbonyl-alkyl and alkoxycarbonyl, is likewise derived from this definition.

Mono- or di-$(C_1-C_4)$-alkylaminocarbonyl represents an amino group which is attached via a carbonyl group and which has a straight-chain or branched or two identical or different straight-chain or branched alkyl substitutents having in each case 1 to 4 carbon atoms. Examples which may be mentioned are: methylamino, ethylamino, n-propylamino, isopropylamino, t-butylamino, N,N-dimethylamino, N,N-diethylamino, N-ethyl-N-methylamino, N-methyl-N-n-propylamino, N-isopropyl-N-n-propylamino and N-t-butyl-N-methylamino.

$(C_1-C_6)$-Alkanoyl represents a straight-chain or branched alkyl radical having 1 to 6 carbon atoms which carries a doubly attached oxygen atom in the 1-position and is attached via the 1-position. Examples which may be mentioned are: formyl, acetyl, propionyl, n-butyryl, i-butyryl, pivaloyl, n-hexanoyl. The corresponding alkanoyl groups with fewer carbon atoms, such as, for example, $(C_1-C_5)$-alkanoyl, $(C_1-$ $C_4$)-alkanoyl and ($C_1$-$C_3$)-alkanoyl, are derived analogously from this definition. In general, preference is given to ($C_1$-$C_3$)-alkanoyl.

The meaning of the corresponding component of other more complex substituents, such as, for example, cycloalkanoyl and alkanoylalkyl, is likewise derived from this definition.

($C_3$-$C_7$)-Cycloalkanoyl represents a cycloalkyl radical having 3 to 7 carbon atoms as defined above which is attached via a carbonyl group.

($C_1$-$C_6$)-Alkanoyloxymethyloxy represents a straight-chain or branched alkanoyloxymethyloxy radical having 1 to 6 carbon atoms. Examples which may be mentioned are: acetoxymethyloxy, propionoxymethyloxy, n-butyroxymethyloxy, i-butyroxymethyloxy, pivaloyloxymethyloxy, n-hexanoyloxymethyloxy. The corresponding alkanoyloxymethyloxy groups having fewer carbon atoms, such as, for example, ($C_1$-$C_3$)-alkanoyloxymethyloxy, are derived analogously from this definition. In general, preference is given to ($C_1$-$C_3$)-alkanoyloxymethyloxy.

($C_6$-$C_{14}$)-Aryl represents an aromatic radical having 6 to 14 carbon atoms. Examples which may be mentioned are: phenyl, naphthyl, phenanthrenyl and anthracenyl. The corresponding aryl groups with fewer carbon atoms, such as, for example, ($C_6$-$C_{10}$)-aryl are derived analogously from this definition. In general, preference is given to ($C_6$-$C_{10}$)-aryl.

The meaning of the corresponding component of other more complex substituents, such as, for example, arylcarbonyl, is likewise derived from this definition.

($C_5$-$C_{10}$)-Heteroaryl or a 5- to 10-membered aromatic heterocycle having up to 3 heteroatoms and/or hetero chain members from the group consisting of S, O, N and NO (N-oxide) represents a mono- or bicyclic heteroaromatic which is attached via a carbon ring atom of the heteroaromatic or, if appropriate, via a nitrogen ring atom of the heteroaromatic. Examples which may be mentioned are: pyridyl, pyridyl N-oxide, pyrimidyl, pyridazinyl, pyrazinyl, thienyl, furyl, pyrrolyl, pyrazolyl, imidazolyl, thiazolyl, oxazolyl or isoxazolyl, indolinyl, indolyl, benzo[b]thienyl, benzo[b]furyl, indazolyl, quinolyl, isoquinolyl, naphthyridinyl, quinazolinyl. The corresponding heterocycles having a smaller ring size, such as, for example, 5- or 6-membered aromatic heterocycles, are derived analogously from this definition. In general, preference is given to 5- or 6-membered aromatic heterocycles, such as, for example, pyridyl, pyridyl N-oxide, pyrimidyl, pyridazinyl, furyl and thienyl.

The meaning of the corresponding component of other more complex substituents, such as, for example, ($C_5$-$C_{10}$)-heteroarylcarbonyl, is likewise derived from this definition.

A 3- to 9-membered saturated or partially unsaturated, mono- or bicyclic, optionally benzo-fused heterocycle having up to 3 heteroatoms and/or hetero chain members from the group consisting of S, SO, $SO_2$, N, NO (N-oxide) and O represents a heterocycle which may contain one or more double bonds, which may be mono- or bicyclic, to which a benzene ring may be fused to two adjacent carbon ring atoms and which is attached via a carbon ring atom or a nitrogen ring atom. Examples which may be mentioned are: tetrahydrofuryl, pyrrolidinyl, pyrrolinyl, piperidinyl, 1,2-dihydropyridinyl, 1,4-dihydropyridinyl, piperazinyl, morpholinyl, morpholinyl N-oxide, thiomorpholinyl, azepinyl, and 1,4-diazepinyl. Preference is given to piperidinyl, morpholinyl and pyrrolidinyl.

The corresponding cycles having a smaller ring size, such as, for example, 5- to 7-membered cycles, are derived analogously from this definition.

The present invention also provides a process for preparing the compounds of the general formula (I) according to the invention where either, according to one process alternative

[A] Compounds of the General Formula (II)

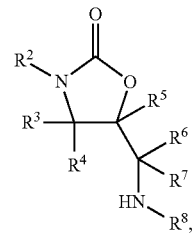

(II)

in which
the radicals $R^2$, $R^3$, $R^4$, $R^5$, $R^6$, $R^7$, and $R^8$ are each as defined above, are reacted with carboxylic acids of the general formula (III)

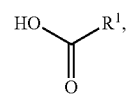

(III)

in which
the radical $R^1$ is as defined above,
or else with the corresponding carbonyl halides, preferably carbonyl chlorides, or else with the corresponding symmetric or mixed carboxylic anhydrides of the carboxylic acids of the general formula (III) defined above
in inert solvents, if appropriate in the presence of an activating or coupling agent and/or a base, to give compounds of the general formula (I)

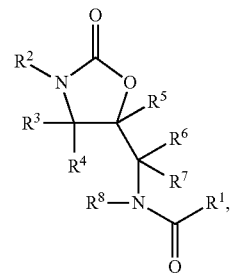

(I)

in which
the radicals $R^1$, $R^2$, $R^3$, $R^4$, $R^5$, $R^6$, $R^7$ and $R^8$ are each as defined above,
or else according to a process alternative

[B] Compounds of the General Formula (IV)

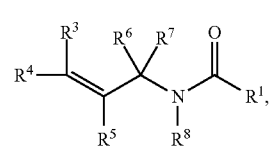

(IV)

in which
the radicals $R^1$, $R^3$, $R^4$, $R^5$, $R^6$, $R^7$ and $R^8$ are each as defined above, are converted, using a suitable selective oxidizing agent in an inert solvent, into the corresponding epoxide of the general formula (V)

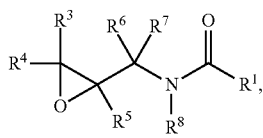

in which
the radicals $R^1$, $R^3$, $R^4$, $R^5$, $R^6$, $R^7$ and $R^8$ are each as defined above,
and, by reaction in an inert solvent, if appropriate in the presence of a catalyst, with an amine of the general formula (VI)

in which
the radical $R^2$ is as defined above,
the compounds of the general formula (VII)

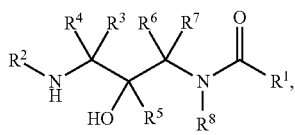

in which
the radicals $R^1$, $R^2$, $R^3$, $R^4$, $R^5$, $R^6$, $R^7$ and $R^8$ are each as defined above,
are initially prepared and
subsequently, in an inert solvent in the presence of phosgene or phosgene equivalents, such as, for example, carbonyldiimidazole (CDT), cyclized to give the compounds of the general formula (I)

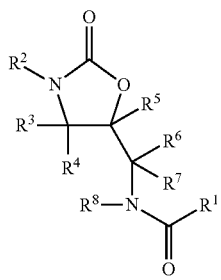

in which
the radicals $R^1$, $R^2$, $R^3$, $R^4$, $R^5$, $R^6$, $R^7$ and $R^8$ are each as defined above,
where—both for process alternative [A] and for process alternative [B]—in the case where $R^2$ contains a 3- to 7-membered saturated or partially unsaturated cyclic hydrocarbon radical having one or more identical or different heteroatoms from the group consisting of N and S, an oxidation with a selective oxidizing agent to afford the corresponding sulphone, sulphoxide or N-oxide may follow and/or
where—both for process alternative [A] and for process alternative [B]—in the case where the compound prepared in this manner has a cyano group in the molecule, an amidination of this cyano group by customary methods may follow and/or
where—both for process alternative [A] and for process alternative [B]—in the case where the compound prepared in this manner has a BOC amino protective group in the molecule, removal of this BOC amino protective group by customary methods may follow and/or
where—both for process alternative [A] and for process alternative [B]—in the case where the compound prepared in this manner has an aniline or benzylamine radical in the molecule, a reaction of this amino group with various reagents such as carboxylic acids, carboxylic anhydrides, carbonyl chlorides, isocyanates, sulphonyl chlorides or alkyl halides to give the corresponding derivatives may follow and/or
where—both for process alternative [A] and for process alternative [B]—in the case where the compound prepared in this manner has a phenyl ring in the molecule, a reaction with chlorosulphonic acid and subsequent reaction with amines to give the corresponding sulphonamides may follow.

The processes according to the invention can be illustrated in an exemplary manner by the equations below:

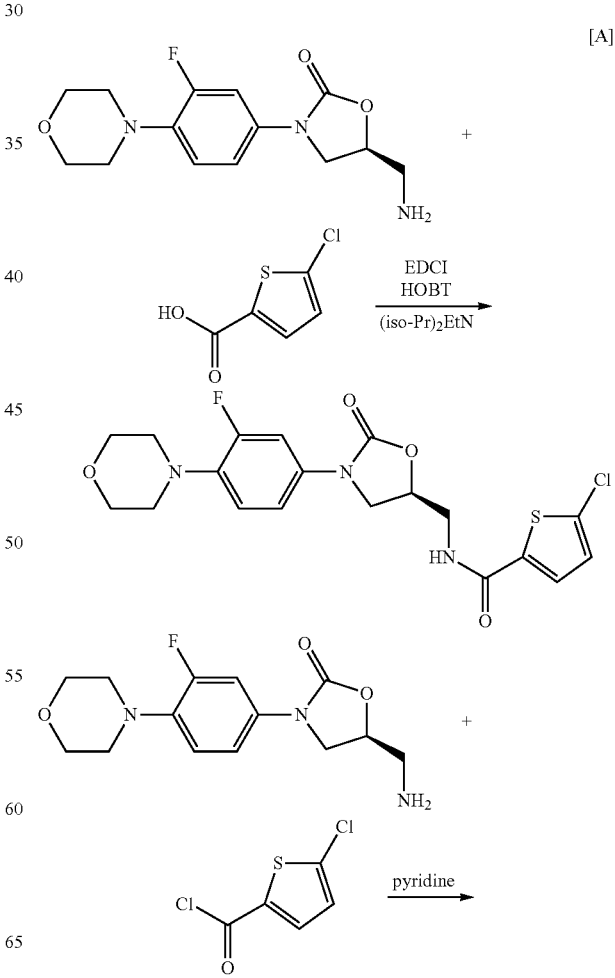

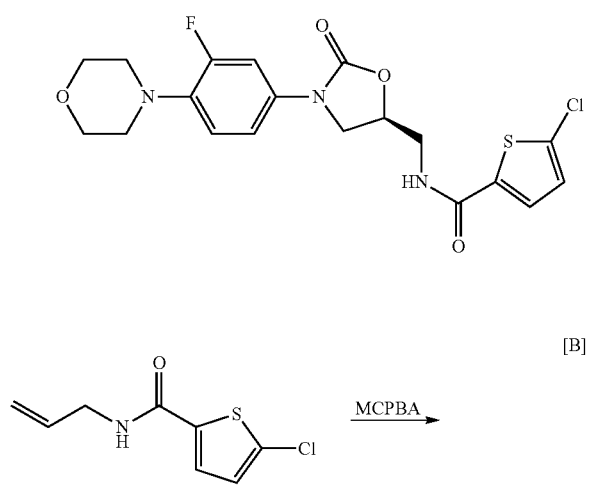

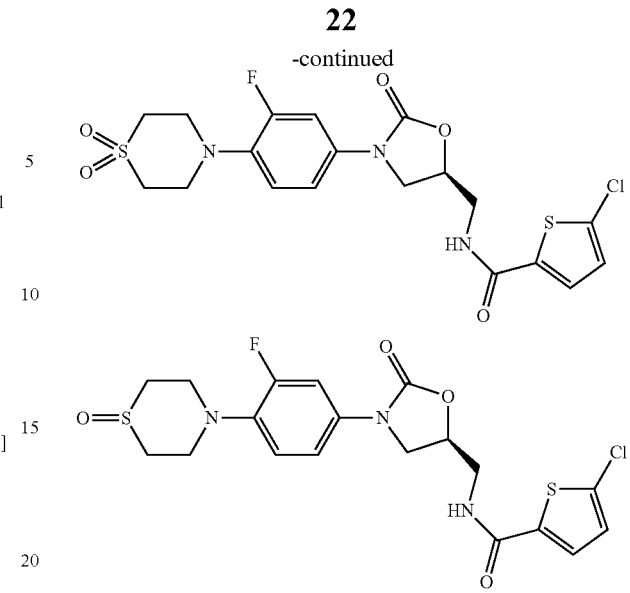

[B]

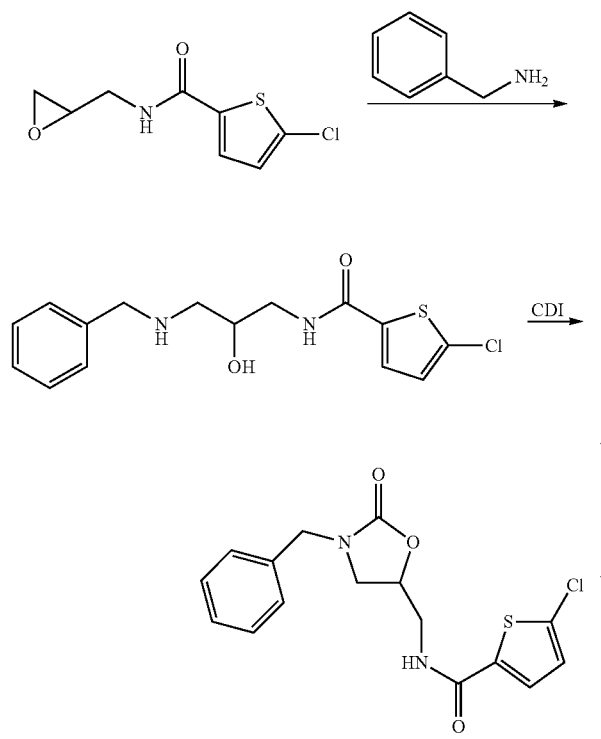

The oxidation step described above, which is optional, can be illustrated in an exemplary manner by the equation below:

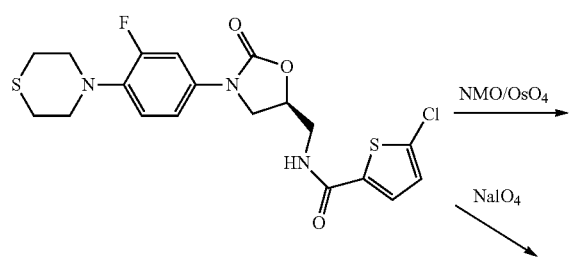

Suitable solvents for the processes described above are organic solvents which are inert under the reaction conditions. These include halogenated hydrocarbons, such as dichloromethane, trichloromethane, carbon tetrachloride, 1,2-dichloroethane, trichloroethane, tetrachloroethane, 1,2-dichloroethylene or trichloroethylene, ethers, such as diethyl ether, dioxane, tetrahydrofuran, glycol dimethyl ether or diethylene glycol dimethyl ether, alcohols, such as methanol, ethanol, n-propanol, isopropanol, n-butanol or tert-butanol, hydrocarbons, such as benzene, xylene, toluene, hexane or cyclohexane, dimethylformamide, dimethyl sulphoxide, acetonitrile, pyridine, hexamethylphosphoric triamide or water.

It is also possible to use solvent mixtures of the solvents mentioned above.

Suitable activating or coupling agents for the processes described above are the reagents which are customarily used for this purpose, for example N'-(3-dimethylaminopropyl)-N-ethylcarbodiimide —HCl, N,N'-dicyclohexylcarbodiimide, 1-hydroxy-1H-benzotriazole.H$_2$O and the like.

Suitable bases are the customary inorganic or organic bases. These preferably include alkali metal hydroxides, such as, for example, sodium hydroxide or potassium hydroxide, or alkali metal carbonates, such as sodium carbonate or potassium carbonate, or sodium methoxide or potassium methoxide or sodium ethoxide or potassium ethoxide or potassium-tert-butoxide, or amides, such as sodium amide, lithium bis-(trimethylsilyl)amide or lithium diisopropylamide, or amines, such as triethylamine, diisopropylethylamine, diisopropylamine, 4-N,N-dimethylaminopyridine or pyridine.

The base can be employed here in an amount of from 1 to 5 mol, preferably from 1 to 2 mol, based on 1 mol of the compounds of the general formula (II).

The reactions are generally carried out in a temperature range of from −78° C. to reflux temperature, preferably in the range from 0° C. to reflux temperature.

The reactions can be carried out at atmospheric, elevated or reduced pressure (for example in the range from 0.5 to 5 bar). In general, the reactions are carried out at atmospheric pressure.

Suitable selective oxidizing agents, both for the preparation of the epoxides and for the optional oxidation to give the sulphone, sulphoxide or N-oxide, are m-chloroperbenzoic acid (MCPBA), sodium metaperiodate, N-methylmorpholine N-oxide (NMO), monoperoxyphthalic acid or osmium tetroxide.

With respect to the preparation of the epoxides, the preparation conditions which are customary for this purpose are employed.

With respect to more detailed process conditions for the optional oxidation to give the sulphone, sulphoxide or N-oxide, reference is made to the following literature: M. R. Barbachyn et al., J. Med. Chem. 1996, 39, 680 and WO-A-97/10223.

Furthermore, reference is made to Examples 14 to 16 given in the experimental part.

The optional amidation is carried out under customary conditions. For more details, reference is made to Examples 31 to 35 and 140 to 147.

The compounds of the general formulae (II), (III), (IV) and (VI) are known per se to the person skilled in the art or can be prepared by customary methods. For oxazolidinones, in particular the 5-(aminomethyl)-2-oxooxazolidines required, cf. WO-A-98/01446; WO-A-93/23384; WO-A-97/03072; J. A. Tucker et al., J. Med. Chem. 1998, 41, 3727; S. J. Brickner et al., J. Med. Chem. 1996, 39, 673; W. A. Gregory et al., J. Med. Chem. 1989, 32, 1673.

The compounds of the general formula (I) according to the invention have an unforeseeable useful pharmacological activity spectrum and are therefore particularly suitable for the prophylaxis and/or treatment of disorders.

The compounds of the general formula (I) according to the ivnention—including the compounds which are excluded by disclaimer from the chemical product protection—act in particular as anticoagulants and can therefore preferably be employed in medicaments for the prophylaxis and/or therapy of thromboembolic disorders. For the purpose of the present invention, "thromboembolic disorders" include, in particular, serious disorders such as myocardial infarct, angina pectoris (including unstable angina), reocclusions and restenoses after angioplasty or aortocoronary bypass, stroke, transitory ischaemic attacks, peripheral arterial occlusion disorders, pulmonary embolisms or deep venous thromboses.

Furthermore, the compounds of the general formula (I) according to the invention—including the compounds which are excluded by disclaimer from the chemical product protection—are also suitable for treating disseminated intravascular coagulation (DIC).

Finally, the compounds of the general formula (I) according to the invention—including the compounds which are excluded by disclaimer from the chemical product protection—are also suitable for the prophylaxis and/or treatment of atherosclerosis and arthritis, and additionally also for the prophylaxis and/or treatment of Alzheimer's disease and cancer.

The compounds of the general formula (I) according to the invention—including the compounds excluded by disclaimer from the chemical product protection—act in particular as selective inhibitors of the blood coagulation factor Xa and do not inhibit, or only inhibit at considerably higher concentrations, other serine proteases as well, such as thrombin, plasmin or trypsin.

In the context of the present invention, inhibitors of the blood coagulation factor Xa in which the $IC_{50}$ values for the factor Xa inhibition are lower by a factor of 100, preferably by a factor of 500, in particular by a factor of 1000, than the $IC_{50}$ values for the inhibition of other serine proteases, in particular thrombin, plasmin and trypsin, are referred to as being "selective", where with a view to the test methods for selectivity, reference is made to the test methods of Examples A-1) a.1) and a.2) described below.

The compounds of the general formula (I) according to the invention—including the compounds which are excluded by disclaimer from the chemical product protection—can furthermore be used for preventing coagulation ex vivo, for example for banked blood or biological samples which contain factor Xa.

The present invention thus provides oxazolidinones of the formula (I) effecting in particular an unexpected, strong and selective inhibition of factor Xa, and this also applies to the compounds excluded by disclaimer from the chemical product protection.

The present invention further provides medicaments and pharmaceutical compositions comprising at least one compound of the general formula (I) according to the invention together with one or more pharmacologically acceptable auxiliaries or excipients, which medicaments and pharmaceutical compositions can be used for the indications mentioned above.

Furthermore, the present invention relates to a method for the prophylaxis and/or treatment of disorders of the human or animal body, in particular of the abovementioned disorders, using the compounds of the general formula (I) according to the invention—including the compounds excluded by disclaimer from the chemical product protection.

Furthermore, the present invention also includes a method for preventing blood coagulation in vitro, in particular in banked blood or biological samples which contain factor Xa, which method is characterized in that compounds of the general formula (I)—including the compounds excluded by disclaimer from the chemical product protection—are added.

All customary administration forms are suitable for administration of the compounds according to the invention. Administration is preferably carried out orally, lingually, sublingually, buccally, rectally or parenterally (i.e. bypassing the intestinal tract, that is intravenously, intraarterially, intracardially, intracutaneously, subcutaneously, transdermally, intraperitoneally or intramuscularly). Particularly suitable are oral and intravenous administration. Very particular preference is given to oral administration, this being a further advantage with respect to the prior-art therapy of thromboembolic disorders.

The novel active compounds of the general formula (I) can be converted in a known manner into the customary formulations, such as tablets, sugar-coated tablets, pills, granules, aerosols, syrups, emulsions, suspensions and solutions, using inert non-toxic pharmaceutically suitable excipients or solvents. Here, the therapeutically active compound should in each case be present in a concentration of from about 0.1 to 95% by weight, preferably from 0.5 to 90% by weight, in particular from 1 to 85% by weight, of the total mixture, i.e. in amounts which are sufficient in order to achieve the dosage range indicated.

In spite of this, if appropriate, it may be necessary to depart from the amounts mentioned, namely depending on the body weight or on the type of administration route, on the individual response to the medicament, on the manner of its formulation and the time or interval at which administration takes place. Thus, in some cases it may be adequate to manage with less than the abovementioned minimum amount, while in other cases the upper limit mentioned must be exceeded. In the case of the administration of relatively large amounts, it may be advisable to divide these into several individual administrations over the course of the day.

The formulations are prepared, for example, by extending the active compounds with solvents and/or excipients, if appropriate using emulsifiers and/or dispersants, it being possible, for example if the diluent used is water, optionally to use organic solvents as auxiliary solvents.

In general it has proved advantageous in the case of intravenous administration to administer amounts from approximately 0.001 to 10 mg/kg, preferably approximately 0.01 to 10 mg/kg, in particular approximately 0.1 to 8 mg/kg, of body weight to achieve effective results.

In general, it has proved advantageous in the case of oral administration to administer amounts from approximately 0.01 to 50 mg/kg, preferably approximately 0.1 to 10 mg/kg, in particular approximately 0.5 to 8 mg/kg, of body weight to achieve effective results.

In spite of this, if appropriate, it may be necessary in the case of intravenous or oral administration to depart from the amounts mentioned, namely depending on the body weight or on the type of administration route, on the individual response to the medicament, on the manner of its formulation and the time or interval at which administration takes place. Thus, in some cases it may be adequate to manage with less than the abovementioned minimum amount, while in other cases the upper limit mentioned must be exceeded. In the case of the administration of relatively large amounts, it may be advisable to divide these over the course of the day, namely into several individual doses or as a continuous infusion.

Compared to the conventional preparations for treating thromboembolic disorders, the compounds of the general formula (I) according to the invention—including the compounds excluded by disclaimer from the chemical product protection—are distinguished in particular by the fact that a greater therapeutic range is achieved by the selective inhibition of factor Xa. For the patient, this means a lower risk of bleeding, and for the treating physician, this means that the patient is easier to adjust. Moreover—owing to the mechanism—the onset of action is more rapid. Above all, however, the compounds according to the invention permit an oral administration form, which is a further advantage of the therapy with the compounds according to the invention.

The present invention is illustrated by the examples below; however, these examples are not meant to restrict the invention in any way.

EXAMPLES

A Evaluation of the Physiological Activity

1. General Test Methods

The particularly advantageous biological properties of the compounds according to the invention can be determined by the following methods.

a) Test Description (In Vitro)

a.1) Determination of the Factor Xa Inhibition

The enzymatic activity of human factor Xa (FXa) was measured using the conversion of a chromogenic substrate specific for FXa. Factor Xa cleaves p-nitroaniline from the chromogenic substrate. The determinations were carried out in microtitre plates as follows.

The test substances, in various concentrations, were dissolved in DMSO and incubated at 25° C. with human FXa (0.5 nmol/l dissolved in 50 mmol/l of tris buffer [C,C,C-tris (hydroxymethyl)-aminomethane], 150 mmol/l of NaCl, 0.1% BSA (bovine serum albumin), pH=8.3) for 10 minutes. Pure DMSO was used as control. The chromogenic substrate (150 µmol/l of Pefachrome® FXa from Pentapharm) was then added. After an incubation time of 20 minutes at 25° C., the extinction at 405 nm was determined. The extinctions of the test mixtures containing test substance were compared with the control mixtures without test substance, and the $IC_{50}$ values were calculated from these data.

a.2) Determination of the Selectivity

To assess selective FXa inhibition, the test substances were examined for their inhibition of other human serine proteases such as thrombin, trypsin and plasmin. To determine the enzymatic activity of thrombin (75 mU/ml), trypsin (500 mU/ml) and plasmin (3.2 nmol/l), these enzymes were dissolved in tris buffer (100 mmol/l, 20 mmol/l $CaCl_2$, pH=8.0) and incubated with test substance or solvent for 10 minutes. The enzymatic reaction was then started by adding the corresponding specific chromogenic substrates (Chromozym Thrombin® from Boehringer Mannheim, Chromozym Trypsin® from Boehringer Mannheim, Chromozym Plasmin® from Boehringer Mannheim) and the extinction at 405 nm was determined after 20 minutes. All determinations were carried out at 37° C. The extinctions of the test mixtures containing test substance were compared with the control samples without test substance, and the $IC_{50}$ values were calculated from these data.

a.3) Determination of the Anticoagulant Action

The anticoagulant action of the test substances was determined in vitro in human plasma. To this end, human blood was drawn off in a mixing ratio of sodium citrate/blood of 1/9 using a 0.11 molar sodium citrate solution as receiver. Immediately after the blood had been drawn off, it was mixed thoroughly and centrifuged at about 2000 g for 10 minutes. The supernatant was pipetted off. The prothrombin time (PT, synonyms: thromboplastin time, quick test) was determined in the presence of varying concentrations of test substance or the corresponding solvent using a commercial test kit (Neoplastin® from Boehringer Mannheim). The test compounds were incubated with the plasma at 37° C. for 10 minutes. Coagulation was then started by addition of thromboplastin, and the time when coagulation occurred was determined. The concentration of test substance which effected a doubling of the prothrombin time was determined.

b) Determination of the Antithrombotic Activity (In Vivo)

b.1) Arteriovenous Shunt Model (Rat)

Fasting male rats (strain: HSD CPB:WU) having a weight of 200-250 g were anaesthetized using a Rompun/Ketavet solution (12 mg/kg/50 mg/kg). Thrombus formation was initiated in an arteriovenous shunt in accordance with the method described by Christopher N. Berry et al., Br. J. Pharmacol. (1994), 113, 1209-1214. To this end, the left jugular vein and the right carotid artery were exposed. The two vessels were connected by an extracorporeal shunt using a polyethylene tube (PE 60) of a length of 10 cm. In the middle, this polyethylene tube was attached to a further polyethylene tube (PE 160) of a length of 3 cm which contained a roughened nylon thread which had been arranged to form a loop, to form a thrombogenic surface. The extracorporeal circulation was maintained for 15 minutes. The shunt was then removed and the nylon thread with the thrombus was weighed immediately. The weight of the nylon thread on its own had been determined before the experiment was started. Before the extracorporeal circulation was set up, the test substances were administered to the animals while awake either intravenously via the tail vein or orally using a pharyngeal tube.

The results are shown in Table 1:

TABLE 1

Antithrombotic activity in the arteriovenous shunt
model (rat) after oral or intravenous administration

| Example | ED$_{50}$ [mg/kg] p.o. | ED$_{50}$ [mg/kg] i.v. |
|---|---|---|
| 1 | | 10 |
| 17 | | 6 |
| 44 | 3 | |
| 95 | | 3 |
| 114 | | 3 |
| 115 | | 3 |
| 123 | 3 | |
| 162 | | 3 | b.2) Arterial Thrombosis Model (Rat)

Male fasting rats (strain: HSD CPB: WU) were anaesthetized as described above. On average, the rats had a weight of about 200 g. The left carotid artery was exposed (about 2 cm). The formation of an arterial thrombus was induced by mechanical injury to the blood vessel in accordance with the method described by K. Meng et al., Naunyn-Schmiedeberg's Arch. Pharmacol. (1977), 301, 115-119. To this end, the exposed carotid artery was clamped from the blood flow, cooled to −12° C. in a metal trough for 2 minutes and, to standardize the size of the thrombi, simultaneously compressed using a weight of 200 g. The blood flow was then additionally reduced by a clip which was placed around the carotid artery distally from the injured section of the vessel. The proximal clamp was removed, and the wound was closed and reopened after 4 hours to remove the injured section of the vessel. The section of the vessel was opened longitudinally and the thrombus was removed from the injured section of the vessel. The moist weight of the thrombi was determined immediately. The test substances were administered to the animals while awake at the beginning of the experiment, either intravenously via the tail vein or orally using a pharyngeal tube.

b.3) Venous Thrombosis Model (Rat)

Male fasting rats (strain: HSD CPB: WU) were anaesthetized as described above. On average, the rats had a weight of about 200 g. The left jugular vein was exposed (about 2 cm). The formation of a venous thrombus was induced by mechanical injury to the blood vessel in accordance with the method described by K. Meng et al., Naunyn-Schmiedeberg's Arch. Pharmacol. (1977), 301, 115-119. To this end, the jugular vein was clamped from the blood flow, cooled to −12° C. in a metal trough for 2 minutes and, to standardize the size of the thrombi, simultaneously compressed using a weight of 200 g. The blood flow was re-opened and the wound was closed. After 4 hours, the wound was re-opened to remove the thrombi from the injured sections of the vessel. The moist weight of the thrombi was determined immediately. The test substances were administered to the animals while awake at the beginning of the experiment, either intravenously via the tail vein or orally using a pharyngeal tube.

B Preparation Examples

Starting Materials

The preparation of 3-morpholinone is described in U.S. Pat. No. 5,349,045.

The preparation of N-(2,3-epoxypropyl)phthalimide is described in J.-W. Chern et al. Tetrahedron Lett. 1998, 39, 8483.

The substituted anilines can be obtained by reacting, for example, 4-fluoronitrobenzene, 2,4-difluoronitrobenzene or 4-chloronitrobenzene with the appropriate amines or amides in the presence of a base. This can also be carried out using Pd catalysts, such as Pd(OAc)$_2$/DPPF/NaOt-Bu (Tetrahedron Lett. 1999, 40, 2035) or copper (Renger, Synthesis 1985, 856; Aebischer et al., Heterocycles 1998, 48, 2225). Likewise, it is possible to initially convert halogenated aromatics without nitro group into the corresponding amides, followed by nitration in the 4-position (U.S. Pat. No. 3,279,880).

I. 4-(4-Morpholin-3-onyl)nitrobenzene

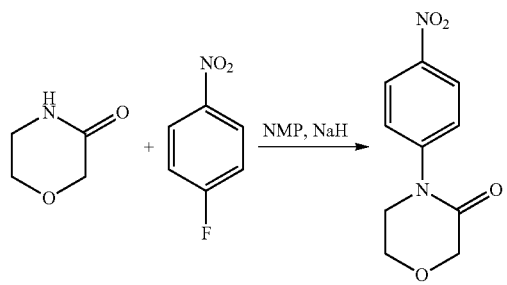

2 mol (202 g) of morpholin-3-one (E. Pfeil, U. Harder, Angew. Chem. 79, 1967, 188) are dissolved in 2 l of N-methylpyrrolidone (NMP). Over a period of 2 h, 88 g (2.2 mol) of sodium hydride (60% in paraffin) are then added a little at a time. After the evolution of hydrogen has ceased, 282 g (2 mol) of 4-fluoronitrobenzene are added dropwise with cooling at room temperature, over a period of 1 h, and the reaction mixture is then stirred overnight. At 12 mbar and 76° C., 1.7 l of the liquid volume are then distilled off, the residue is poured into 2 l of water and this mixture is extracted twice with in each case 1 l of ethyl acetate. After washing of the combined organic phases with water, the mixture is dried over sodium sulphate and the solvent is distilled off under reduced pressure. Purification is carried out by silica gel chromatography using hexane/ethyl acetate (1:1) and subsequent crystallization from ethyl acetate. This gives 78 g of product as a colourless to brownish solid, in a yield of 17.6% of theory.

$^1$H-NMR (300 MHz, CDCl$_3$): 3.86 (m, 2H, CH$_2$CH$_2$), 4.08 (m, 2H, CH$_2$CH$_2$), 4.49 (s, 2H, CH$_2$CO), 7.61 (d, 2H, $^3$J=8.95 Hz, CHCH), 8.28 (d, 2H, $^3$J=8.95 Hz, CHCH)

MS (r.I. %)=222 (74, M$^+$), 193 (100), 164 (28), 150 (21), 136 (61), 117 (22), 106 (24), 90 (37), 76 (38), 63 (32), 50 (25)

The following compounds were synthesized analogously:

3-fluoro-4-(4-morpholin-3-onyl)nitrobenzene 4-(N-piperidonyl)nitrobenzene 3-fluoro-4-(N-piperidonyl)nitrobenzene 4-(N-pyrrolidonyl)nitrobenzene 3-fluoro-4-(N-pyrrolidonyl)nitrobenzene

II. 4-(4-Morpholin-3-onyl)aniline

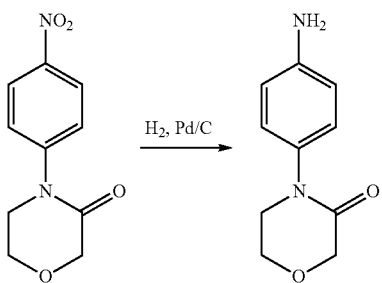 [SMILES: O=C1COCCN1c1ccc([N+](=O)[O-])cc1 ; Nc1ccc(N2CCOCC2=O)cc1]

In an autoclave, 63 g (0.275 mol) of 4-(4-morpholin-3-onyl)nitrobenzene are dissolved in 200 ml of tetrahydrofuran, admixed with 3.1 g of Pd/C (5% ig) and hydrogenated at 70° C. and a hydrogen pressure of 50 bar for 8 h. The catalyst is filtered off, the solvent is then distilled off under reduced pressure and the product is purified by crystallization from ethyl acetate. 20 g of product are obtained as a colourless to bluish solid, in a yield of 37.6% of theory.

Purification can also be carried out by silica gel chromatography using hexane/ethyl acetate.

$^1$H-NMR (300 MHz, CDCl$_3$): 3.67 (m, 2H, CH$_2$CH$_2$), 3.99 (m, 2H, CH$_2$CH$_2$), 4.27 (s, 2H, CH$_2$CO), 6.68 (d, 2H, $^3$J=8.71 Hz, CHCH), 7.03 (d, 2H, $^3$J=8.71 Hz, CHCH)

MS (r.I. %)=192 (100, M$^+$), 163 (48), 133 (26), 119 (76), 106 (49), 92 (38), 67 (27), 65 (45), 52 (22), 28 (22)

The following compounds were synthesized analogously:
3-fluoro-4-(4-morpholin-3-onyl)aniline
4-(N-piperidonyl)aniline
3-fluoro-4-(N-piperidonyl)aniline
4-(N-pyrrolidonyl)aniline
3-fluoro-4-(N-pyrrolidonyl)aniline General method for preparing 4-substituted anilines by reacting 1-fluoro-4-nitrobenzenes and 1-chloro-4-nitrobenzenes with primary or secondary amines, followed by reduction

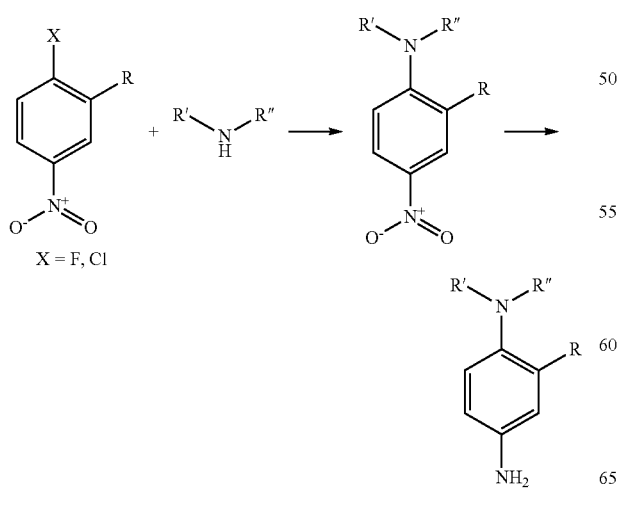

Equimolar amounts of the fluoronitrobenzene or chloronitrobenzene and the amine are dissolved in dimethyl sulphoxide or acetonitrile (0.1 M to 1 M solution), and the mixture is stirred at 100° C. overnight. After cooling to RT, the reaction mixture is diluted with ether and washed with water. The organic phase is dried over MgSO$_4$, filtered and concentrated. If a precipitate forms in the reaction mixture, the precipitate is filtered off and washed with ether or acetonitrile. If the mother liquor also contains product, it is worked up as described using ether and water. The crude products can be purified by silica gel chromatography (dichloromethane/cyclohexane and dichloromethane/ethanol mixtures).

For the subsequent reduction, the nitro compound is dissolved in methanol, ethanol or ethanol/dichloromethane mixtures (0.01 M to 0.5 M solution) admixed with palladium on carbon (10%) and stirred under an atmospheric hydrogen pressure overnight. The mixture is then filtered and concentrated. The crude product can be purified by silica gel chromatography (dichloromethane/ethanol mixtures) or preparative reversed-phase HPLC (acetonitrile/water mixtures).

Alternatively, the reducing agent used can also be iron powder. To this end, the nitro compound is dissolved in acetic acid (0.1 M to 0.5 M solution) and, at 90° C., six equivalents of iron powder and water (0.3 to 0.5 times the volume of the acetic acid) are added a little at a time over a period of 10-15 min. After a further 30 min at 90° C., the mixture is filtered and the filtrate is concentrated. The residue is worked up by extraction with ethyl acetate and 2N aqueous sodium hydroxide solution. The organic phase is dried over magnesium sulphate, filtered and concentrated. The crude product can be purified by silica gel chromatography (dichloromethane/ethanol mixtures) or preparative reversed-phase HPLC (acetonitrile/water mixtures).

The following starting materials were prepared in an analogous manner:

III-1. tert-butyl-1-(4-aminophenyl)-L-prolinate

MS (ESI): m/z (%)=304 (M+H+MeCN, 100), 263 (M+H, 20);
HPLC (method 4): rt=2.79 min.

III-2. 1-(4-aminophenyl)-3-piperidinecarboxamide

MS (ESI): m/z (%)=220 (M+H, 100);
HPLC (method 4): rt=0.59 min.

III-3. 1-(4-aminophenyl)-4-piperidincarboxamide

MS (ESI): m/z (%)=220 (M+H, 100);
HPLC (method 4): rt=0.57 min.

III-4. 1-(4-aminophenyl)-4-piperidinone

MS (ESI): m/z (%)=191 (M+H, 100);
HPLC (method 4): rt=0.64 min.

III-5. 1-(4-aminophenyl)-L-prolinamide

MS (ESI): m/z (%)=206 (M+H, 100);
HPLC (method 4): rt=0.72 min.

III-6. [1-(4-aminophenyl)-3-piperidinyl]methanol

MS (ESI): m/z (%)=207 (M+H, 100);
HPLC (method 4): rt=0.60 min.

III-7. [1-(4-aminophenyl)-2-piperidinyl]methanol

MS (ESI): m/z (%)=207 (M+H, 100);
HPLC (method 4): rt=0.59 min.

III-8. ethyl 1-(4-aminophenyl)-2-piperidinecarboxylate

MS (ESI): m/z (%)=249 (M+H, 35), 175 (100);
HPLC (method 4): rt=2.43 min.

III-9. [1-(4-aminophenyl)-2-pyrrolidinyl]methanol

MS (ESI): m/z (%)=193 (M+H, 45);
HPLC (method 4): rt=0.79 min.

III-10. 4-(2-methylhexahydro-5H-pyrrolo[3,4-d]isoxazol-5-yl)phenylamine starting from 2-methylhexahydro-2H-pyrrolo[3,4-d]isoxazole (Ziegler, Carl B., et al.; J. Heterocycl. Chem.; 25; 2; 1988; 719-723)
MS (ESI): m/z (%)=220 (M+H, 50), 171 (100);
HPLC (method 4): rt=0.54 min.

III-11. 4-(1-pyrrolidinyl)-3-(trifluoromethyl)aniline

MS (ESI): m/z (%)=231 (M+H, 100);
HPLC (method 7): rt=3.40 min.

III-12. 3-chloro-4-(1-pyrrolidinyl)aniline

MS (ESI): m/z (%)=197 (M+H, 100);
HPLC (method 4): rt=0.78 min.

III.43. 5-amino-2-(4-morpholinyl)benzamide

MS (ESI): m/z (%)=222 (M+H, 100);
HPLC (method 4): rt=0.77 min.

III-14. 3-methoxy-4-(4-morpholinyl)aniline

MS (ESI): m/z (%)=209 (M+H, 100);
HPLC (method 4): rt=0.67 min.

III-15. 1-[5-amino-2-(4-morpholinyl)phenyl]ethanone

MS (ESI): m/z (%)=221 (M+H, 100);
HPLC (method 4): rt=0.77 min.

General method for preparing 4-substituted anilines by reacting 1-fluoro-4-nitrobenzenes with amides, followed by reduction

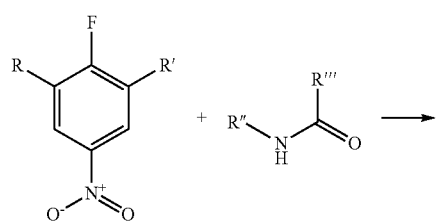

-continued

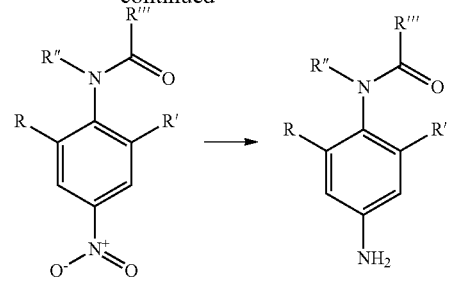

The amide is dissolved in DMF and admixed with 1.5 equivalents of potassium tert-butoxide. The mixture is stirred at RT for 1 h, and 1.2 equivalents of the 1-fluoro-4-nitrobenzene are then added a little at a time. The reaction mixture is stirred at RT overnight, diluted with ether or ethyl acetate and washed with sat. aqu. sodium bicarbonate solution. The organic phase is dried over magnesium sulphate, filtered and concentrated. The crude product can be purified by silica gel chromatography (dichloromethane/ethanol mixtures).

For the subsequent reduction, the nitro compound is dissolved in ethanol (0.01 M to 0.5 M solution), admixed with palladium on carbon (10%) and stirred under atmospheric hydrogen pressure overnight. The mixture is then filtered and concentrated. The crude product can be purified by silica gel chromatography (dichloromethane/ethanol mixtures) or preparative reversed-phase HPLC (acetonitrile/water mixtures).

Alternatively, the reducing agent used can also be iron powder. To this end, the nitro compound is dissolved in acetic acid (0.1 M to 0.5 M solution) and, at 90° C., six equivalents of iron powder and water (0.3 to 0.5 times the volume of the acetic acid) are added a little at a time over a period of 10-15 min. After a further 30 min at 90° C., the mixture is filtered and the filtrate is concentrated. The residue is worked up by extraction with ethyl acetate and 2N aqueous sodium hydroxide solution. The organic phase is dried over magnesium sulphate, filtered and concentrated. The crude product can be purified by silica gel chromatography (dichloromethane/ethanol mixtures) or preparative reversed-phase HPLC (acetonitrile/water mixtures).

The following starting materials were prepared in an analogous manner:

IV-1. 1-[4-amino-2-(trifluoromethyl)phenyl]-2-pyrrolidinone

MS (ESI): m/z (%)=245 (M+H, 100);
HPLC (method 4): rt=2.98 min

IV-2. 4-[4-amino-2-(trifluoromethyl)phenyl]-3-morpholinone

MS (ESI): m/z (%)=261 (M+H, 100);
HPLC (method 4): rt=2.54 min.

IV-3. 4-(4-amino-2-chlorophenyl)-3-morpholinone

MS (ESI): m/z (%)=227 (M+H, 100);
HPLC (method 4): rt=1.96 min.

IV-4. 4-(4-amino-2-methylphenyl)-3-morpholinone

MS (ESI): m/z (%)=207 (M+H, 100);
HPLC (method 4): rt=0.71 min.

IV-5. 5-amino-2-(3-oxo-4-morpholinyl)benzonitrile

MS (ESI): m/z (%)=218 (M+H, 100);
HPLC (method 4): rt=1.85 min.

IV-6. 1-(4-amino-2-chlorophenyl)-2-pyrrolidinone

MS (ESI): m/z (%)=211 (M+H, 100);
HPLC (method 4): rt=2.27 min.

IV-7. 4-(4-amino-2,6-dimethylphenyl)-3-morpholinone starting from 2-fluoro-1,3-dimethyl-5-nitrobenzene (Bartoli et al., J. Org. Chem. 1975, 40, 872):
MS (ESI): m/z (%)=221 (M+H, 100);
HPLC (method 4): rt=0.77 min.

IV-8. 4-(2,4-diaminophenyl)-3-morpholinone starting from 1-fluoro-2,4-dinitrobenzene:
MS (ESI): m/z (%)=208 (M+H, 100);
HPLC (method 4): rt=0.60 min.

IV-9. 4-(4-amino-2-chlorophenyl)-2-methyl-3-morpholinone starting from 2-methyl-3-morpholinone (Pfeil, E.; Harder, U.; Angew. Chem. 1967, 79, 188):
MS (ESI): m/z (%)=241 (M+H, 100);
HPLC (method 4): rt=2.27 min.

IV-10. 4-(4-amino-2-chlorophenyl)-6-methyl-3-morpholinone starting from 6-methyl-3-morpholinone (EP 350 002):
MS (ESI): m/z (%)=241 (M+H, 100);
HPLC (method 4): rt=2.43 min.

SYNTHESIS EXAMPLES

The Examples 1 to 13, 17 to 19 and 36 to 57 below refer to process variant [A].

Example 1

Preparation of 5-chloro-N-{[(5S)-3-(3-fluoro-4-morpholinophenyl)-2-oxo-1,3-oxazolidin-5-yl]methyl}-2-thiophenecarboxamide

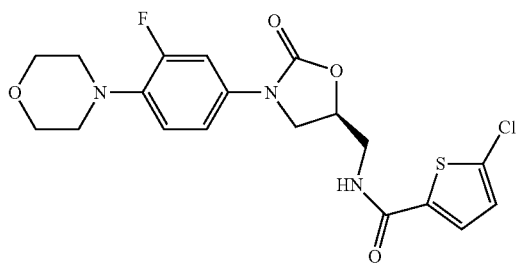 [SMILES: O=C(NC[C@H]1CN(c2ccc(N3CCOCC3)c(F)c2)C(=O)O1)c1ccc(Cl)s1]

(5S)-5-(Aminomethyl)-3-(3-fluoro-4-morpholinophenyl)-1,3-oxazolidin-2-one (preparation see S. J. Brickner et al., J. Med. Chem. 1996, 39, 673) (0.45 g, 1.52 mmol), 5-chlorothiophene-2-carboxylic acid (0.25 g, 1.52 mmol) and 1-hydroxy-1H-benzotriazole (HOBT) (0.3 g, 1.3 equivalents) are dissolved in 9.9 ml of DMF. 0.31 g (1.98 mmol, 1.3 equivalents) of N'-(3-dimethylaminopropyl)-N-ethylcarbodiimide (EDCI) are added, and 0.39 g (0.53 ml, 3.05 mmol, 2 equivalents) of diisopropylethylamine (DIEA) are added dropwise at room temperature. The mixture is stirred at room temperature overnight. 2 g of silica gel are added, and the mixture is evaporated to dryness under reduced pressure. The residue is chromatographed on silica gel using a toluene/ethyl acetate gradient. This gives 0.412 g (61.5% of theory) of the target compound of melting point (m.p.) 197° C.
$R_f$ (SiO$_2$, toluene/ethyl acetate 1:1)=0.29 (starting material=0.0);
MS (DCI) 440.2 (M+H), Cl pattern;
$^1$H-NMR (d$_6$-DMSO, 300 MHz) 2.95 (m, 4H), 3.6 (t, 2H), 3.72 (m, 4H), 3.8 (dd, 1H), 4.12 (t, 1H), 4.75-4.85 (m, 1H), 7.05 (t, 1H), 7.15-7.2 (m, 3H), 7.45 (dd, 1H), 7.68 (d, 1H), 8.95 (t, 1H).

Example 2

5-Chloro-N-{[(5S)-3-(4-morpholinophenyl)-2-oxo-1,3-oxazolidin-5-yl]methyl}-2-thiophenecarboxamide

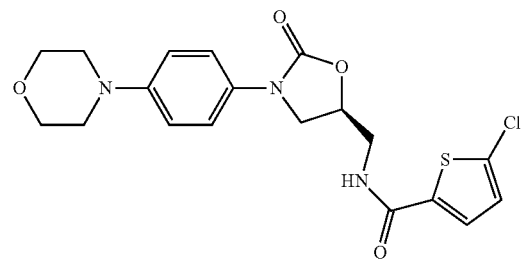 [SMILES: O=C(NC[C@H]1CN(c2ccc(N3CCOCC3)cc2)C(=O)O1)c1ccc(Cl)s1]

is obtained analogously from benzyl 4-morpholinophenylcarbamate via the (5S)-5-(aminomethyl)-3-(4-morpholinophenyl)-1,3-oxazolidin-2-one intermediate (see Example 1).
M.p.: 198° C.;
IC$_{50}$ value=43 nM;
$R_f$(SiO$_2$, toluene/ethyl acetate 1:1)=0.24.

Example 3

5-Chloro-N-({(5S)-3-[3-fluoro-4-(1,4-thiazinan-4-yl)phenyl]-2-oxo-1,3-oxazolidin-5-yl}methyl)-2-thiophenecarboxamide

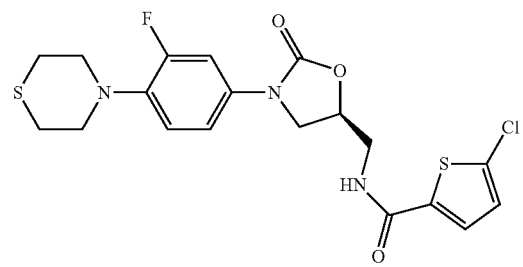 [SMILES: O=C(NC[C@H]1CN(c2ccc(N3CCSCC3)c(F)c2)C(=O)O1)c1ccc(Cl)s1]

is obtained analogously from (5S)-5-(aminomethyl)-3-[3-fluoro-4-(1,4-thiazinan-4-yl)phenyl]-1,3-oxazolidin-2-one (preparation see M. R. Barbachyn et al., J. Med. Chem. 1996, 39, 680).

M.p.: 193° C.;

Yield: 82%;

$R_f$ (SiO$_2$, toluene/ethyl acetate 1:1)=0.47 (starting material=0.0).

Example 4

5-Bromo-N-({(5S)-3-[3-fluoro-4-(1,4-thiazinan-4-yl)phenyl]-2-oxo-1,3-oxazolidin-5-yl}methyl)-2-thiophenecarboxamide

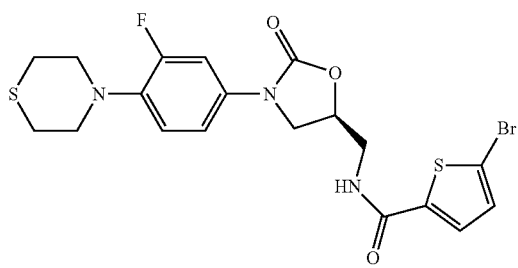 [SMILES: O=C(NC[C@H]1CN(c2ccc(N3CCSCC3)c(F)c2)C(=O)O1)c1ccc(Br)s1]

is obtained analogously from 5-bromothiophene-2-carboxylic acid.

M.p.: 200° C.

Example 5

N-({(5S)-3-[3-Fluoro-4-(1,4-thiazinan-4-yl)phenyl]-2-oxo-1,3-oxazolidin-5-yl}methyl)-5-methyl-2-thiophenecarboxamide

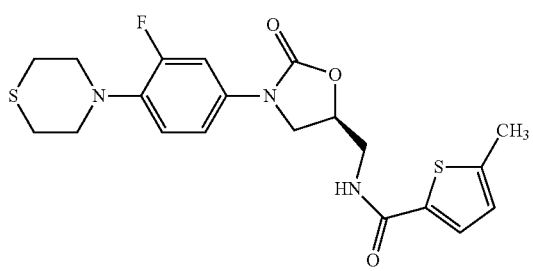 [SMILES: Cc1ccc(C(=O)NC[C@H]2CN(c3ccc(N4CCSCC4)c(F)c3)C(=O)O2)s1]

is obtained analogously from 5-methylthiophene-2-carboxylic acid.

M.p.: 167° C.

Example 6

5-Chloro-N-{[(5S)-3-(6-methylthieno[2,3-b]pyridin-2-yl)-2-oxo-1,3-oxazolidin-5-yl]methyl}-2-thiophenecarboxamide

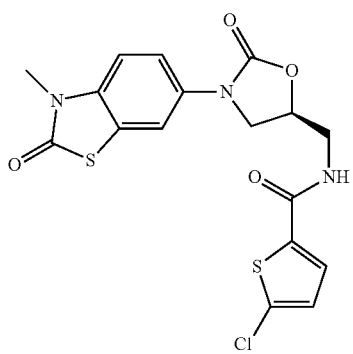 [SMILES: Cn1c(=O)sc2cc(N3C[C@H](CNC(=O)c4ccc(Cl)s4)OC3=O)ccc21]

is obtained analogously from (5S)-5-(aminomethyl)-3-(6-methylthieno[2,3-b]pyridin-2-yl)-1,3-oxazolidin-2-one (preparation see EP-A-785 200).

M.p.: 247° C.

Example 7

5-Chloro-N-{[(5S)-3-(3-methyl-2-oxo-2,3-dihydro-1,3-benzothiazol-6-yl)-2-oxo-1,3-oxazolidin-5-yl]methyl}-2-thiophenecarboxamide is obtained analogously from 6-[(5S)-5-(aminomethyl)-2-oxo-1,3-oxazolidin-3-yl]-3-methyl-1,3-benzothiazol-2(3H)-one (preparation see EP-A-738 726).

M.p.: 217° C.

Example 8

5-Chloro-N-[((5S)-3-{3-fluoro-4-[4-(4-pyridinyl)piperazino]phenyl}-2-oxo-1,3-oxazolidin-5-yl)methyl]-2-thiophenecarboxamide

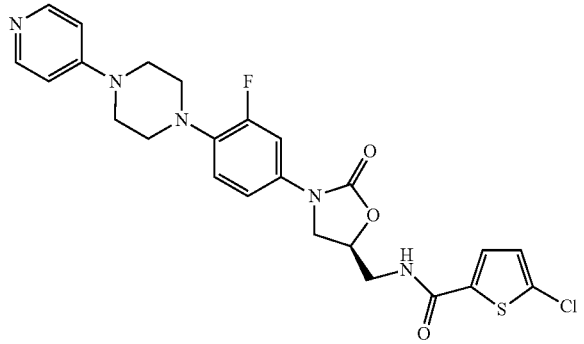 [SMILES: O=C(NC[C@H]1CN(c2ccc(N3CCN(c4ccncc4)CC3)c(F)c2)C(=O)O1)c1ccc(Cl)s1]

is obtained analogously from (5S)-5-(aminomethyl)-3-{3-fluoro-4-[4-(4-pyridinyl)piperazino]phenyl}-1,3-oxazolidin-2-one (preparation analogously to J. A. Tucker et al., J. Med. Chem. 1998, 41, 3727).
MS (ESI) 516 (M+H), Cl pattern.

Example 9

5-Chloro-N-({(5S)-3-[3-fluoro-4-(4-methylpiperazino)phenyl]-2-oxo-1,3-oxazolidin-5-yl}methyl)-2-thiophenecarboxamide

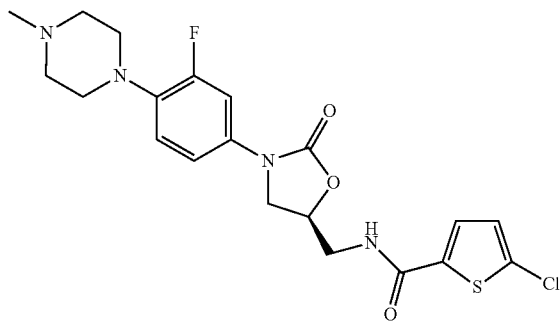 [SMILES: CN1CCN(c2ccc(N3C[C@H](CNC(=O)c4ccc(Cl)s4)OC3=O)cc2F)CC1]

is obtained analogously from (5S)-5-(aminomethyl)-3-[3-fluoro-4-(4-methylpiperazino)phenyl]-1,3-oxazolidin-2-one.

Example 10

5-Chloro-N-({(5S)-3-[3-fluoro-4-(4-tert-butoxycarbonylpiperazin-1-yl)phenyl]-2-oxo-1,3-oxazolidin-5-yl}methyl)-2-thiophenecarboxamide

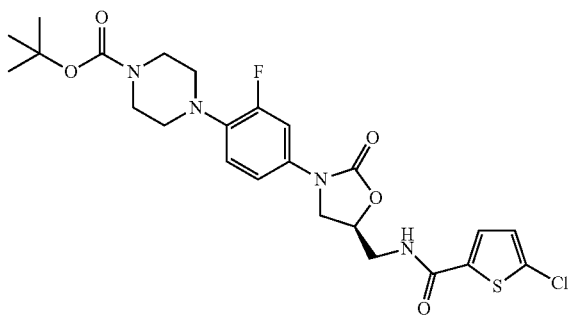 [SMILES: CC(C)(C)OC(=O)N1CCN(c2ccc(N3C[C@H](CNC(=O)c4ccc(Cl)s4)OC3=O)cc2F)CC1]

is obtained analogously from (5S)-5-(aminomethyl)-3-[3-fluoro-4-(4-tert-butoxycarbonylpiperazin-1-yl)phenyl]-1,3-oxazolidin-2-one (preparation see WO-A-93/23384, which has already been cited).
M.p.: 184° C.;
$R_f$ (SiO$_2$, toluene/ethyl acetate 1:1)=0.42.

Example 11

5-Chloro-N-({(5S)-3-[3-fluoro-4-(piperazin-1-yl)phenyl]-2-oxo-1,3-oxazolidin-5-yl}methyl)-2-thiophenecarboxamide

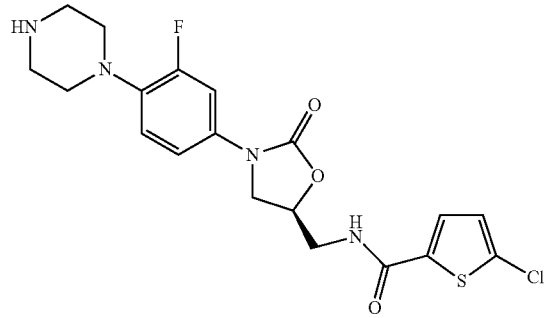 [SMILES: O=C(NC[C@H]1CN(c2ccc(N3CCNCC3)c(F)c2)C(=O)O1)c1ccc(Cl)s1]

is obtained by reacting Example 10 with trifluoroacetic acid in methylene chloride.
IC$_{50}$ value=140 nM;
$^1$H-NMR [d$_6$-DMSO]: 3.01-3.25 (m, 8H), 3.5-3.65 (m, 2H), 3.7-3.9 (m, 1H), 4.05-4.2 (m, 1H), 4.75-4.9 (m, 1H), 7.05-7.25 (m, 3H), 7.5 (dd, 1H), 7.7 (d, 1H), 8.4 (broad s, 1H), 9.0 (t, 1H).

Example 12

5-Chloro-N-[((5S)-3-(2,4'-bipyridinyl-5-yl)-2-oxo-1,3-oxazolidin-5-yl)methyl]-2-thiophenecarboxamide

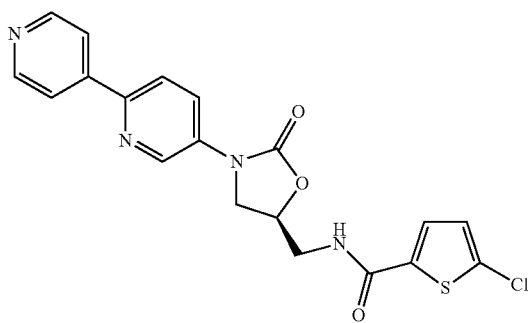 [SMILES: O=C(NC[C@H]1CN(c2ccc(-c3ccncc3)nc2)C(=O)O1)c1ccc(Cl)s1]

is obtained analogously from (5S)-5-aminomethyl-3-(2,4'-bipyridinyl-5-yl)-2-oxo-1,3-oxazolidin-2-one (preparation see EP-A-789 026).

R$_f$ (SiO$_2$, ethyl acetate/ethanol 1:2)=0.6;
MS (ESI) 515 (M+H), Cl pattern.

Example 13

5-Chloro-N-{[(5S)-2-oxo-3-(4-piperidinophenyl)-1,3-oxazolidin-5-yl]methyl}-2-thiophenecarboxamide

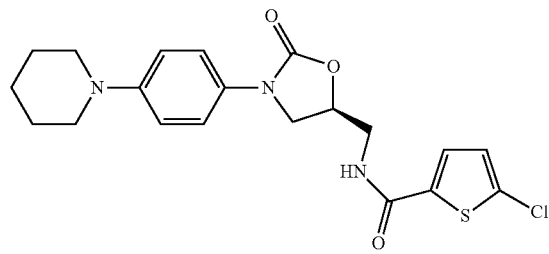 [SMILES: O=C(NC[C@H]1CN(c2ccc(N3CCCCC3)cc2)C(=O)O1)c1ccc(Cl)s1]

is obtained from 5-(hydroxymethyl)-3-(4-piperidinophenyl)-1,3-oxazolidin-2-one (preparation see DE 2708236) after mesylation, reaction with potassium phthalimide, hydrazinolysis and reaction with 5-chlorothiophene-2-carboxylic acid.

R$_f$ (SiO$_2$, ethyl acetate/toluene 1:1)=0.31;
m.p. 205° C.

Example 17

5-Chloro-N-({(5S)-2-oxo-3-[4-(2-oxo-1-pyrrolidinyl)phenyl]-1,3-oxazolidin-5-yl}methyl)-2-thiophenecarboxamide

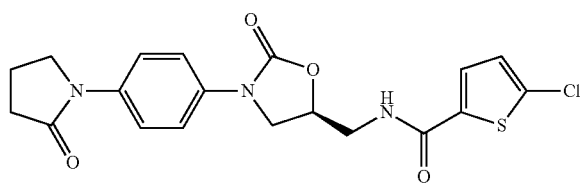 [SMILES: O=C(NC[C@H]1CN(c2ccc(N3CCCC3=O)cc2)C(=O)O1)c1ccc(Cl)s1]

Analogously to the known synthesis scheme (see S. J. Brickner et al., J. Med. Chem. 1996, 39, 673), 1-(4-aminophenyl)pyrrolidin-2-one (preparation see Reppe et al., Justus Liebigs Ann. Chem.; 596; 1955; 209) gives, after reaction with benzyloxycarbonyl chloride, followed by reaction with R-glycidyl butyrate, mesylation, reaction with potassium phthalimide, hydrazinolysis in methanol and reaction with 5-chlorothiophene-2-carboxylic acid, finally 5-chloro-N-({(5S)-2-oxo-3-[4-(2-oxo-1-pyrrolidinyl)phenyl]-1,3-oxazolidin-5-yl}methyl)-2-thiophenecarboxamide. The 5-chloro-N-({(5S)-2-oxo-3-[4-(2-oxo-1-pyrrolidinyl)-phenyl]-1,3-oxazolidin-5-yl}methyl)-2-thiophenecarboxamide obtained in this manner has an IC$_{50}$ value of 4 nM (test method for the IC$_{50}$ value according to Example A-1.a.1 described above) "determination of the inhibition of factor Xa").

M.p.: 229° C.;
R$_f$ value (SiO$_2$, toluene/ethyl acetate 1:1)=0.05 (starting material:=0.0);

MS (ESI): 442.0 (21%, M+Na, Cl pattern), 420.0 (72%, M+H, Cl pattern), 302.3 (12%), 215 (52%), 145 (100%);

$^1$H-NMR (d$_6$-DMSO, 300 MHz): 2.05 (m, 2H), 2.45 (m, 2H), 3.6 (t, 2H), 3.77-3.85 (m, 3H), 4.15 (t, 1H), 4.75-4.85 (m, 1H), 7.2 (d, 1H), 7.5 (d, 2H), 7.65 (d, 2H), 7.69 (d, 1H), 8.96 (t, 1H).

The individual steps of the synthesis of Example 17 described above with the respective precursors are as follows:

At −20° C., 4 g (22.7 mmol) of 1-(4-aminophenyl)pyrrolidin-2-one and 3.6 ml (28.4 mmol) of N,N-dimethylaniline in 107 ml of tetrahydrofuran are admixed slowly with 4.27 g (25.03 mmol) of benzyl chloroformate. The mixture is stirred at −20° C. for 30 minutes and then allowed to warm to room temperature. 0.5 l of ethyl acetate are added, and the organic phase is washed with 0.5 l of saturated NaCl solution. The organic phase is separated off and dried with MgSO$_4$, and the solvent is evaporated under reduced pressure. The residue is triturated with diethyl ether and filtered off with suction. This gives 5.2 g (73.8% of theory) of benzyl 4-(2-oxo-1-pyrrolidinyl)phenylcarbamate as light-beige crystals of melting point 174° C.

At −10° C. and under argon, 1.47 g (16.66 mmol) of isoamyl alcohol in 200 ml of tetrahydrofuran are admixed dropwise with 7.27 ml of a 2.5 M solution of n-butyllithium (BuLi) in hexane, a further 8 ml of BuLi solution being required for the added indicator N-benzylidenebenzylamine to change colour. The mixture is stirred at −10° C. for 10 minutes and cooled to −78° C., and a solution of 4.7 g (15.14 mmol) of benzyl 4-(2-oxo-1-pyrrolidinyl)phenylcarbamate is added slowly. Another 4 ml of n-BuLi solution are then added until the colour of the indicator changes to pink. The mixture is stirred at −78° C. for 10 minutes, 2.62 g (18.17 mmol) of R-glycidyl butyrate are added and the mixture is stirred at −78° C. for another 30 minutes.

Overnight, the mixture is allowed to warm to room temperature, 200 ml of water are added and the THF fraction is evaporated under reduced pressure. The aqueous residue is extracted with ethyl acetate and the organic phase is dried with MgSO$_4$ and evaporated under reduced pressure. The residue is triturated with 500 ml of diethyl ether and the precipitated crystals are filtered off with suction under reduced pressure.

This gives 3.76 g (90% of theory) of (5R)-5-(hydroxymethyl)-3-[4-(2-oxo-1-pyrrolidinyl)phenyl]-1,3-oxazolidin-2-one of melting point 148° C., with an R$_f$ value (SiO$_2$, toluene/ethyl acetate 1:1) of 0.04 (starting material=0.3).

At 0° C., 3.6 g (13.03 mmol) of (5R)-5-(hydroxymethyl)-3-[4-(2-oxo-1-pyrrolidinyl)phenyl]-1,3-oxazolidin-2-one and 2.9 g (28.67 mmol) of triethylamine are initially charged with stirring in 160 ml of dichloromethane. 1.79 g (15.64 mmol) of methanesulphonyl chloride are added with stirring, and the mixture is stirred at 0° C. for 1.5 hours and then at room temperature for 3 h.

The reaction mixture is washed with water and the aqueous phase is reextracted with methylene chloride. The combined organic extracts are dried with MgSO$_4$ and concentrated. The residue (1.67 g) is then dissolved in 70 ml of acetonitrile, admixed with 2.62 g (14.16 mmol) of potassium phthalimide and stirred in a closed vessel at 180° C. in a microwave oven for 45 minutes.

The mixture is filtered off from insoluble residues, the filtrate is evaporated under reduced pressure and the residue (1.9 g) is dissolved in methanol and admixed with 0.47 g (9.37 mmol) of hydrazine hydrate. The mixture is boiled for 2 hours, cooled, admixed with saturated sodium bicarbonate solution and extracted six times with a total of 2 l of methylene chloride. The combined organic extracts of the crude (5S)-5-(aminomethyl)-3-[4-(2-oxo-1-pyrrolidinyl)phenyl]-1,3-oxazolidin-2-one are dried with MgSO$_4$ and concentrated under reduced pressure.

The end product, 5-chloro-N-({(5S)-2-oxo-3-[4-(2-oxo-1-pyrrolidinyl)phenyl]-1,3-oxazolidin-5-yl}methyl)-2-thiophenecarboxamide, is prepared by dissolving 0.32 g (1.16 mmol) of the (5S)-5-(aminomethyl)-3-[4-(2-oxo-1-pyrrolidinyl)phenyl]-1,3-oxazolidin-2-one prepared above, 5-chlorothiophene-2-carboxylic acid (0.19 g; 1.16 mmol) and 1-hydroxy-1H-benzotriazole hydrate (HOBT) (0.23 g, 1.51 mmol) in 7.6 ml of DMF. 0.29 g (1.51 mmol) of N'-(3-dimethylaminopropyl)-N-ethylcarbodiimide (EDCI) are added, and 0.3 g (0.4 ml; 2.32 mmol, 2 equivalents) of diisopropylethylamine (DIEA) are added dropwise at room temperature. The mixture is stirred at room temperature overnight.

The mixture is evaporated to dryness under reduced pressure and the residue is dissolved in 3 ml of DMSO and chromatographed on an RP-MPLC using an acetonitrile/water/0.5% TFA gradient. From the appropriate fractions, the acetonitrile fraction is evaporated and the precipitated compound is filtered off with suction. This gives 0.19 g (39% of theory) of the target compound.

The following compounds were prepared in an analogous manner:

Example 18

5-Chloro-N-({(5S)-2-oxo-3-[4-(1-pyrrolidinyl)phenyl]-1,3-oxazolidin-5-yl}methyl)-2-thiophenecarboxamide Analogously to Example 17, 4-pyrrolidin-1-yl-aniline (Reppe et al., Justus Liebigs Ann. Chem.; 596; 1955; 151) gives the compound 5-chloro-N-({(5S)-2-oxo-3-[4-(1-pyrrolidinyl)phenyl]-1,3-oxazolidin-5-yl}methyl)-2-thiophenecarboxamide.
IC$_{50}$=40 nM;
m.p.: 216° C.;
R$_f$ value (SiO$_2$, toluene/ethyl acetate 1:1)=0.31 [starting material:=0.0].

Example 19

5-Chloro-N-({(5S)-2-oxo-3-[4-(diethylamino)phenyl]-1,3-oxazolidin-5-yl}methyl)-2-thiophenecarboxamide Analogously, N,N-diethylphenyl-1,4-diamine (U.S. Pat. No. 2,811,555; 1955) gives the compound 5-chloro-N-({(5S)-2-oxo-3-[4-(diethylamino)phenyl]-1,3-oxazolidin-5-yl}methyl)-2-thiophenecarboxamide.
IC$_{50}$=270 nM;
m.p.: 181° C.;
R$_f$ value (SiO$_2$, toluene/ethyl acetate 1:1)=0.25 [starting material:=0.0].

Example 36

5-Chloro-N-({(5S)-3-[2-methyl-4-(4-morpholinyl)phenyl]-2-oxo-1,3-oxazolidin-5-yl}methyl)-2-thiophenecarboxamide starting from 2-methyl-4-(4-morpholinyl)aniline (J. E. LuValle et al. J. Am. Chem. Soc. 1948, 70, 2223):

MS (ESI): m/z (%)=436 ([M+H]$^+$, 100), Cl pattern;
HPLC (method 1): rt (%)=3.77 (98).
IC$_{50}$: 1.26 μM

Example 37

5-Chloro-N-({[(5S)-3-(3-chloro-4-morpholinophenyl)-2-oxo-1,3-oxazolidin-5-yl]methyl}-2-thiophenecarboxamide starting from 3-chloro-4-(4-morpholinyl)aniline (H. R. Snyder et al. J. Pharm. Sci. 1977, 66, 1204):
MS (ESI): m/z (%)=456 ([M+H]$^+$, 100), Cl$_2$ pattern;
HPLC (method 2): rt (%)=4.31 (100).
IC$_{50}$: 33 nM

Example 38

5-Chloro-N-({(5S)-3-[4-(4-morpholinylsulphonyl)phenyl]-2-oxo-1,3-oxazolidin-5-yl}methyl)-2-thiophenecarboxamide starting from 4-(4-morpholinylsulphonyl)aniline (Adams et al. J. Am. Chem. Soc. 1939, 61, 2342):
MS (ESI): m/z (%)=486 ([M+H]$^+$, 100), Cl pattern;
HPLC (method 3): rt (%)=4.07 (100).
IC$_{50}$: 2 μM

Example 39

5-Chloro-N-({(5S)-3-[4-(1-azetidinylsulphonyl)phenyl]-2-oxo-1,3-oxazolidin-5-yl}methyl)-2-thiophenecarboxamide starting from 4-(1-azetidinylsulphonyl)aniline:
MS (DCI, NH$_3$): (%)=473 ([M+NH$_4$]$^+$, 100), Cl pattern;
HPLC (method 3): rt (%)=4.10 (100).
IC$_{50}$: 0.84 μM

Example 40

5-Chloro-N-[((5S)-3-{4-[(dimethylamino)sulphonyl]phenyl}-2-oxo-1,3-oxazolidin-5-yl)methyl]-2-thiophenecarboxamide starting from 4-amino-N,N-dimethylbenzenesulphonamide (I. K. Khanna et al. J. Med. Chem. 1997, 40, 1619):
MS (ESI): m/z (%)=444 ([M+H]$^+$, 100), Cl pattern;
HPLC (method 3): rt (%)=4.22 (100).
IC$_{50}$: 90 nM General method for the acylation of 5-(aminomethyl)-3-[4-(2-oxo-1-pyrrolidinyl)phenyl]-1,3-oxazolidin-2-one with carbonyl chlorides

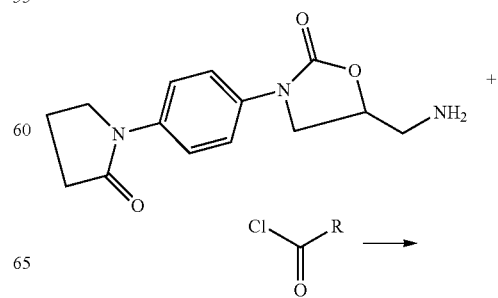

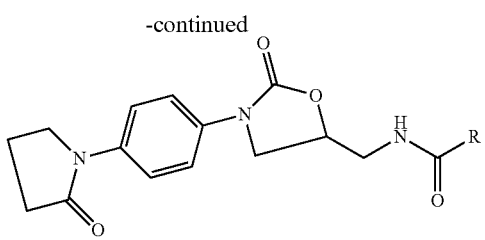

Under argon and at room temperature, an about 0.1 molar solution of 5-(aminomethyl)-3-[4-(2-oxo-1-pyrrolidinyl)phenyl]-1,3-oxazolidin-2-one (from Example 45) (1.0 eq.) and absolute pyridine (about 6 eq.) in absolute dichloromethane is added dropwise to the appropriate acid chloride (2.5 eq.). The mixture is stirred at room temperature for about 4 h, and about 5.5 eq of PS-trisamine (Argonaut Technologies) are then added. The suspension is stirred gently for 2 h, diluted with dichloromethane/DMF (3:1) and then filtered (the resin is washed with dichloromethane/DMF) and the filtrate is concentrated. If appropriate, the product that is obtained is purified by preparative RP-HPLC.

The following compounds were prepared in an analogous manner:

Example 41

N-({2-oxo-3-[4-(2-oxo-1-pyrrolidinyl)phenyl]-1,3-oxazolidin-5-yl}methyl)-2-thiophene-carboxamide LC-MS (method 6): m/z (%)=386 (M+H, 100);
LC-MS: rt (%)=3.04 (100).
  IC$_{50}$: 1.3 μM General method for preparing acyl derivatives starting from 5-(aminomethyl)-3-[4-(2-oxo-1-pyrrolidinyl)phenyl]-1,3-oxazolidin-2-one and carboxylic acids

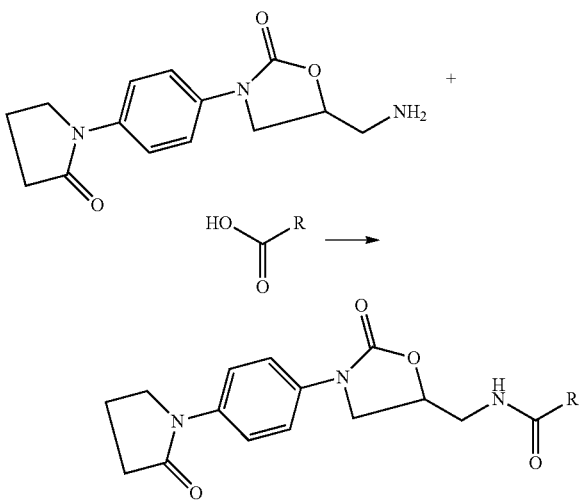

The appropriate carboxylic acid (about 2 eq.) and a mixture of absolute dichloromethane/DMF (about 9:1) are added to 2.9 eq. of resin-bonded carbodiimide (PS-carbodiimide, Argonaut Technologies). The mixture is shaken gently at room temperature for about 15 min, 5-(aminomethyl)-3-[4-(2-oxo-1-pyrrolidinyl)phenyl]-1,3-oxazolidin-2-one (from Example 45) (1.0 eq.) is then added and the mixture is shaken overnight, after which the resin is filtered off (and washed with dichloromethane), and the filtrate is concentrated. If appropriate, the resulting product is purified by preparative RP-HPLC.

The following compounds were prepared in an analogous manner:

Example 42

5-Methyl-N-({2-oxo-3-[4-(2-oxo-1-pyrrolidinyl)phenyl]-1,3-oxazolidin-5-yl}methyl)-2-thiophenecarboxamide LC-MS: m/z (%)=400 (M+H, 100);
LC-MS (method 6): rt (%)=3.23 (100).
  IC$_{50}$: 0.16 μM

Example 43

5-Bromo-N-({2-oxo-3-[4-(2-oxo-1-pyrrolidinyl)phenyl]-1,3-oxazolidin-5-yl}methyl)-2-thiophenecarboxamide LC-MS: m/z (%)=466 (M+H, 100);
LC-MS (method 5): rt (%)=3.48 (78).
  IC$_{50}$: 0.014 μM

Example 44

5-Chloro-N-({(5S)-2-oxo-3-[4-(3-oxo-4-morpholinyl)phenyl]-1,3-oxazolidin-5-yl}methyl)-2-thiophenecarboxamide

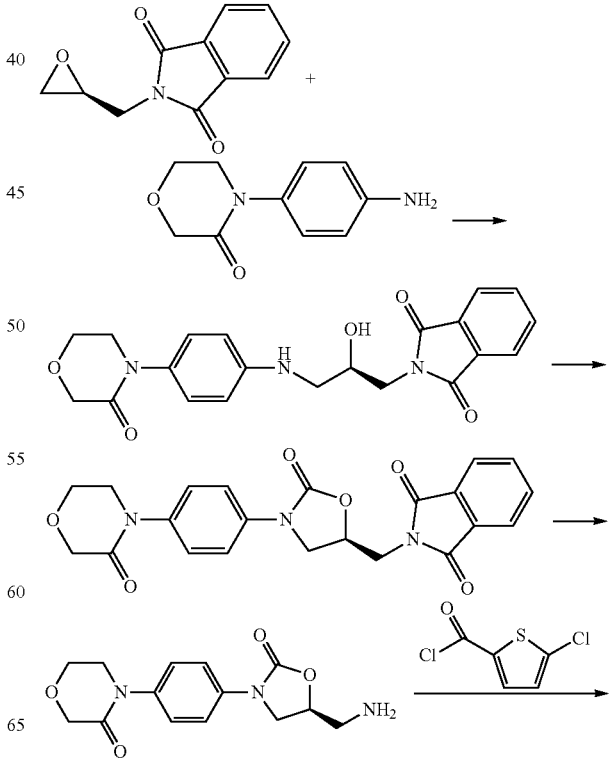

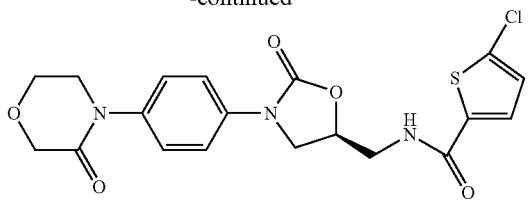

a) 2-((2R)-2-Hydroxy-3-{[4-(3-oxo-4-morpholinyl)phenyl]amino}propyl)-1H-isoindole-1,3(2H)-dione A suspension of 2-[(2S)-2-oxiranylmethyl]-1H-isoindole-1,3(2H)-dione (A. Gutcait et al. *Tetrahedron Asym.* 1996, 7, 1641) (5.68 g, 27.9 mmol) and 4-(4-aminophenyl)-3-morpholinone (5.37 g, 27.9 mmol) in ethanol/water (9:1, 140 ml) is refluxed for 14 h (the precipitate dissolves, after some time again formation of a precipitate). The precipitate (desired product) is filtered off, washed three times with diethyl ether and dried. The combined mother liquors are concentrated under reduced pressure and, after addition of a second portion of 2-[(2S)-2-oxiranylmethyl]-1H-isoindole-1,3(2H)-dione (2.84 g, 14.0 mmol), suspended in ethanol/water (9:1, 70 ml) and refluxed for 13 h (the precipitate dissolves, after some time again formation of a precipitate). The precipitate (desired product) is filtered off, washed three times with diethyl ether and dried. Total yield: 10.14 g, 92% of theory.

MS (ESI): m/z (%)=418 ([M+Na]$^+$, 84), 396 ([M+H]$^+$, 93);
HPLC (method 3): rt (%)=3.34 (100).

b) 2-({(5S)-2-Oxo-3-[4-(3-oxo-4-morpholinyl)phenyl]-1,3-oxazolidin-5-yl}methyl)-1H-isoindole-1,3(2H)-dione Under argon and at room temperature, N,N'-carbonyldiimidazole (2.94 g, 18.1 mmol) and dimethylaminopyridine (a catalytic amount) are added to a suspension of the amino alcohol (3.58 g, 9.05 mmol) in tetrahydrofuran (90 ml). The reaction suspension is stirred at 60° C. for 12 h (the precipitate dissolves, after some time again formation of a precipitate), admixed with a second portion of N,N'-carbonyldiimidazole (2.94 g, 18.1 mmol) and stirred at 60° C. for another 12 h. The precipitate (desired product) is filtered off, washed with tetrahydrofuran and dried. The filtrate is concentrated under reduced pressure and further product is purified by flash chromatography (dichloromethane/methanol mixtures). Total yield: 3.32 g, 87% of theory.

MS (ESI): m/z (%)=422 ([M+H]$^+$, 100);
HPLC (method 4): rt (%)=3.37 (100).

c) 5-Chloro-N-({(5S)-2-oxo-3-[4-(3-oxo-4-morpholinyl)phenyl]-1,3-oxazolidin-5-yl}methyl)-2-thiophenecarboxamide At room temperature, methylamine (40% strength in water, 10.2 ml, 0.142 mol) is added dropwise to a suspension of the oxazolidinone (4.45 g, 10.6 mmol) in ethanol (102 ml). The reaction mixture is refluxed for 1 h and concentrated under reduced pressure. The crude product is used without further purification for the next reaction. Under argon and at 0° C., 5-chlorothiophene-2-carbonyl chloride (2.29 g, 12.7 mmol) is added dropwise to a solution of the amine in pyridine (90 ml). Ice-cooling is removed and the reaction mixture is stirred at room temperature for 1 h and admixed with water. Dichloromethane is added and the phases are separated, and the aqueous phase is then extracted with dichloromethane. The combined organic phases are dried (sodium sulphate), filtered and concentrated under reduced pressure. The desired product is purified by flash chromatography (dichloromethane/methanol mixtures). Total yield: 3.92 g, 86% of theory.

M.p: 232-233° C.;

$^1$H NMR (DMSO-d$^6$, 200 MHz): 9.05-8.90 (t, J=5.8 Hz, 1H), 7.70 (d, J=4.1 Hz, 1H), 7.56 (d, J=9.0 Hz, 2H), 7.41 (d, J=9.0 Hz, 2H), 7.20 (d, J=4.1 Hz, 1H), 4.93-4.75 (m, 1H), 4.27-4.12 (m, 3H), 4.02-3.91 (m, 2H), 3.91-3.79 (dd, J=6.1 Hz, 9.2 Hz, 1H), 3.76-3.66 (m, 2H), 3.66-3.54 (m, 2H);

MS (ESI): m/z (%)=436 ([M+H]$^+$, 100, Cl pattern);
HPLC (method 2): rt (%)=3.60 (100);
$[\alpha]^{21}_D$=−38° (c 0.2985, DMSO); ee: 99%.
IC$_{50}$: 0.7 nM The following compounds were prepared in an analogous manner:

Example 45

5-Methyl-N-({(5S)-2-oxo-3-[4-(3-oxo-4-morpholinyl)phenyl]-1,3-oxazolidin-5-yl}methyl)-2-thiophenecarboxamide MS (ESI): m/z (%)=831 ([2M+H]$^+$, 100), 416 ([M+H]$^+$, 66);
HPLC (method 3): rt (%)=3.65 (100).
IC$_{50}$: 4.2 nM

Example 46

5-Bromo-N-({(5S)-2-oxo-3-[4-(3-oxo-4-morpholinyl)phenyl]-1,3-oxazolidin-5-yl}methyl)-2-thiophenecarboxamide MS (ESI): m/z (%)=480 ([M+H]$^+$, 100, Br pattern);
HPLC (method 3): rt (%)=3.87 (100).
IC$_{50}$: 0.3 nM

Example 47

5-Chloro-N-{[(5S)-3-(3-isopropyl-2-oxo-2,3-dihydro-1,3-benzoxazol-6-yl)-2-oxo-1,3-oxazolidin-5-yl]methyl}-2-thiophenecarboxamide

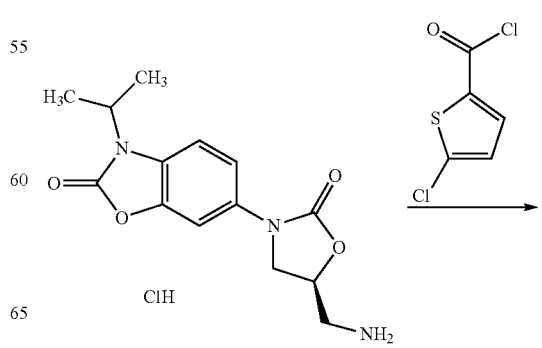

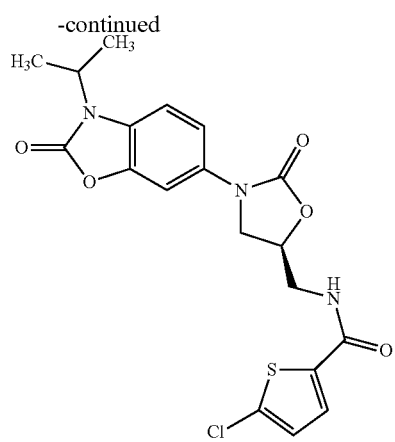

200 mg (0.61 mmol) of 6-[(5S)-5-(aminomethyl)-2-oxo-1,3-oxazolidin-3-yl]-3-isopropyl-1,3-benzoxazol-2(3H)-one hydrochloride (EP 738726) are suspended in 5 ml of tetrahydrofuran and admixed with 0.26 ml (1.83 mmol) of triethylamine and 132 mg (0.73 mmol) of 5-chlorothiophene-2-carbonyl chloride. The reaction mixture is stirred at room temperature overnight and then concentrated. The product is isolated by column chromatography (silica gel, methylene chloride/ethanol=50/1 to 20/1). This gives 115 mg (43% of theory) of the desired compound.

MS (ESI): m/z (%)=436 (M+H, 100);

HPLC (method 4): rt=3.78 min.

The following compounds were prepared in an analogous manner:

| Example No. | Structure | M.p. [° C.] | $IC_{50}$ [µM] |
|---|---|---|---|
| 48 | 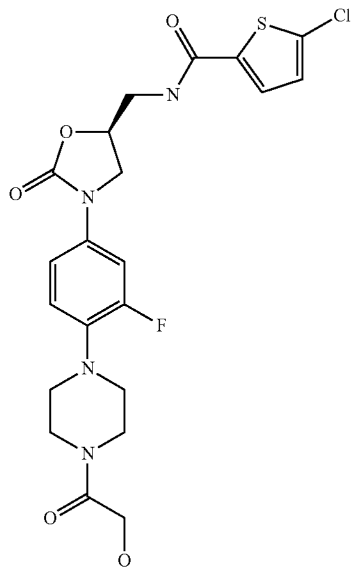 | 210 | 0.12 |
| 49 | 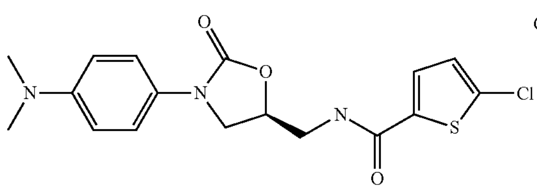 | 234 | 0.074 |
| 50 | 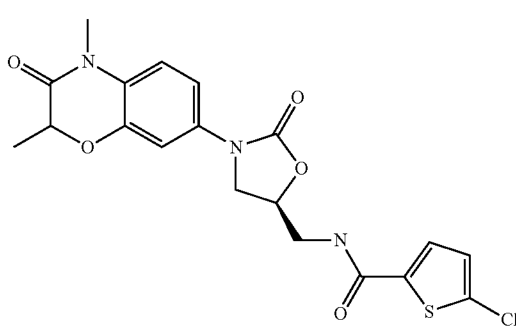 | 195 | 1.15 |

-continued

| Example No. | Structure | M.p. [° C.] | IC$_{50}$ [µM] |
|---|---|---|---|
| 51 | Chiral | 212 | 1.19 |
| 52 | Chiral | 160 | 0.19 |
| 53 | Chiral | MS (ESI): m/z (%) = 431 ([M + H]$^+$, 100), Cl pattern | 0.74 |
| 54 | Chiral<br>from 5-amino-2-pyrrolidino-benzonitrile (Grell, W., Hurnaus, R.; Griss, G., Sauter, R.; Rupprecht, E. et al.; J. Med. Chem. 1998, 41; 5219) | 221 | 0.13 |
| 55 | Chiral<br>from 3-(4-amino-phenyl)-oxazolidin-2-one (Artico, M. et al.; Farmaco Ed. Sci. 1969, 24; 179) | 256 | 0.04 |
| 56 | Chiral | 218 | 0.004 |
| 57 | Chiral | 226 | 0.58 |

Examples 20 to 30 and 58 to 139 below refer to process variant [B], and Examples 20 and 21 describe the preparation of precursors.

Example 20

Preparation of N-allyl-5-chloro-2-thiophenecarboxamide

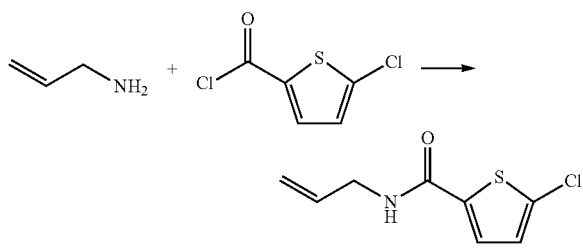

An ice-cooled solution of 2.63 ml (35 mmol) of allylamine in 14.2 ml of absolute pyridine and 14.2 ml of absolute THF is admixed dropwise with 5-chloro-thiophene-2-carbonyl chloride (7.61 g, 42 mmol). Ice-cooling is removed and the mixture is stirred at room temperature for 3 h and then concentrated under reduced pressure. The residue is admixed with water and the solid is filtered off. The crude product is purified by flash chromatography over silica gel (dichloromethane).

Yield: 7.20 g (99% of theory);
MS (DCI, $NH_4$): m/z (%)=219 (M+$NH_4$, 100), 202 (M+H, 32);
HPLC (method 1): rt (%)=3.96 min (98.9).

Example 21

Preparation of 5-chloro-N-(2-oxiranylmethyl)-2-thiophenecarboxamide

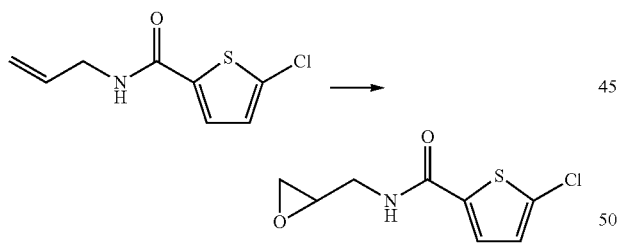

An ice-cooled solution of 2.0 g (9.92 mmol) of N-allyl-5-chloro-2-thiophenecarboxamide in 10 ml of dichloromethane is admixed with metachloroperbenzoic acid (3.83 g, about 60% strength). The mixture is stirred overnight, during which it is allowed to warm to room temperature, and is then washed with 10% sodium hydrogen sulphate solution (three times). The organic phase is washed with saturated sodium bicarbonate solution (twice) and with saturated sodium chloride solution, dried over magnesium sulphate and concentrated. The product is purified by silica gel chromatography (cyclohexane/ethyl acetate 1:1).

Yield: 837 mg (39% of theory);
MS (DCI, $NH_4$): m/z (%)=253 (M+$NH_4$, 100), 218 (M+H, 80);
HPLC (method 1): rt (%)=3.69 min (about 80).

General method for preparing substituted N-(3-amino-2-hydroxypropyl)-5-chloro-2-thiophenecarboxamide derivatives starting from 5-chloro-N-(2-oxiranylmethyl)-2-thiophenecarboxamide At room temperature or at temperatures up to 80° C., 5-chloro-N-(2-oxiranylmethyl)-2-thiophenecarboxamide (1.0 eq.) is added a little at a time to a solution of the primary amine or aniline derivative (1.5 to 2.5 eq.) in 1,4-dioxane, 1,4-dioxane/water mixtures or ethanol, ethanol/water mixtures (about 0.3 to 1.0 mol/l). The mixture is stirred for 2 to 6 hours and then concentrated. From the reaction mixture, the product can be isolated by silica gel chromatography (cyclohexane/ethyl acetate mixtures, dichloromethane/methanol mixtures or dichloromethane/methanol/triethylamine mixtures).

The following compounds were prepared in an analogous manner:

Example 22

N-[3-(Benzylamino)-2-hydroxypropyl]-5-chloro-2-thiophenecarboxamide

MS (ESI): m/z (%)=325 (M+H, 100);
HPLC (method 1): rt (%)=3.87 min (97.9).

Example 23

5-Chloro-N-[3-(3-cyanoanilino)-2-hydroxypropyl]-2-thiophenecarboxamide

MS (ESI): m/z (%)=336 (M+H, 100);
HPLC (method 2): rt (%)=4.04 min (100).

Example 24

5-Chloro-N-[3-(4-cyanoanilino)-2-hydroxypropyl]-2-thiophenecarboxamide

MS (ESI): m/z (%)=336 (M+H, 100);
HPLC (method 1): rt (%)=4.12 min (100).

Example 25

5-Chloro-N-{3-[4-(cyanomethyl)anilino]-2-hydroxypropyl}-2-thiophenecarboxamide

MS (ESI): m/z (%)=350 (M+H, 100);
HPLC (method 4): rt (%)=3.60 min (95.4).

Example 26

5-Chloro-N-{3-[3-(cyanomethyl)anilino]-2-hydroxypropyl}-2-thiophenecarboxamide

MS (ESI): m/z (%)=350 (M+H, 100);
HPLC (method 4): rt (%)=3.76 min (94.2).

Example 58 tert-Butyl 4-[(3-{[(5-chloro-2-thienyl)carbonyl]amino}-2-hydroxypropyl)amino]-benzylcarbamate starting from tert-butyl 4-aminobenzylcarbamate (*Bioorg. Med. Chem. Lett.*; 1997; 1921-1926):
MS (ES-pos): m/z (%)=440 (M+H, 100), (ES-neg): m/z (%)=438 (M−H, 100);
HPLC (method 1): rt (%)=4.08 (100).

Example 59 tert-Butyl 4-[(3-{[(5-chloro-2-thienyl)carbonyl]amino}-2-hydroxypropyl)amino]-phenyl-carbamate starting from N-tert-butyloxycarbonyl-1,4-phenylenediamine:
MS (ESI): m/z (%)=426 (M+H, 45), 370 (100);
HPLC (method 1): rt (%)=4.06 (100).

Example 60 tert-Butyl 2-hydroxy-3-{[4-(2-oxo-1-pyrrolidinyl)phenyl]amino}propyl-carbamate starting from 1-(4-aminophenyl)-2-pyrrolidinone (*Justus Liebigs Ann. Chem.*; 1955; 596; 204):
MS (DCI, $NH_3$): m/z (%)=350 (M+H, 100);
HPLC (method 1): rt (%)=3.57 (97).

Example 61

5-Chloro-N-(3-{[3-fluoro-4-(3-oxo-4-morpholinyl)phenyl]amino}-2-hydroxypropyl)-2-thiophenecarboxamide 800 mg (3.8 mmol) of 4-(4-amino-2-fluorophenyl)-3-morpholinone and 700 mg (3.22 mmol) of 5-chloro-N-(2-oxiranylmethyl)-2-thiophenecarboxamide in 15 ml of ethanol and 1 ml of water are heated under reflux for 6 hours. The mixture is concentrated under reduced pressure and treated with ethyl acetate, precipitated crystals are filtered off with suction and the mother liquor is chromatographed giving 276 mg (17% of theory) of the target compound.
$R_f$(ethyl acetate): 0.25.

Example 62

(N-(3-Anilino-2-hydroxypropyl)-5-chloro-2-thiophenecarboxamide starting from aniline:
MS (DCI, $NH_3$): m/z (%)=311 ([M+H]$^+$, 100), Cl pattern;
HPLC (method 3): rt (%)=3.79 (100).

Example 63

5-Chloro-N-(2-hydroxy-3-{[4-(3-oxo-4-morpholinyl)phenyl]amino}propyl)-2-thiophenecarboxamide starting from 4-(4-aminophenyl)-3-morpholinone:
MS (ESI): m/z (%)=410 ([M+H]$^+$, 50), Cl pattern;
HPLC (method 3): rt (%)=3.58 (100).

Example 64

N-[3-({4-[Acetyl(cyclopropyl)amino]phenyl}amino)-2-hydroxypropyl]-5-chloro-2-thiophenecarboxamide starting from N-(4-aminophenyl)-N-cyclopropylacetamide:
MS (ESI): m/z (%)=408 ([M+H]$^+$, 100), Cl pattern;
HPLC (method 3): rt (%)=3.77 (100).

Example 65

N-[3-({4-[Acetyl(methyl)amino]phenyl}amino)-2-hydroxypropyl]-5-chloro-2-thiophenecarboxamide starting from N-(4-aminophenyl)-N-methylacetamide:
MS (ESI): m/z (%)=382 (M+H, 100);
HPLC (method 4): rt=3.31 min.

Example 66

5-Chloro-N-(2-hydroxy-3-{[4-(1H-1,2,3-triazol-1-yl)phenyl]amino}propyl)-2-thiophenecarboxamide starting from 4-(1H-1,2,3-triazol-1-yl)aniline (Bouchet et al.; *J. Chem. Soc. Perkin Trans. 2*; 1974; 449):
MS (ESI): m/z (%)=378 (M+H, 100);
HPLC (method 4): rt=3.55 min.

Example 67 tert-butyl 1-{4-[(3-{[(5-chloro-2-thienyl)carbonyl]amino}-2-hydroxypropyl)-amino]phenyl}-L-prolinate MS (ESI): m/z (%)=480 (M+H, 100);
HPLC (method 4): rt=3.40 min.

Example 68

1-{4-[(3-{[(5-Chloro-2-thienyl)carbonyl]amino}-2-hydroxypropyl)amino]phenyl}-4-piperidinecarboxamide MS (ESI): m/z (%)=437 (M+H, 100);
HPLC (method 4): rt=2.39 min.

Example 69

1-{4-[(3-{[(5-Chloro-2-thienyl)carbonyl]amino}-2-hydroxypropyl)-amino]phenyl}-3-piperidinecarboxamide MS (ESI): m/z (%)=437 (M+H, 100);
HPLC (method 4): rt=2.43 min.

Example 70

5-Chloro-N-(2-hydroxy-3-{[4-(4-oxo-1-piperidinyl)phenyl]amino}propyl)-2-thiophenecarboxamide MS (ESI): m/z (%)=408 (M+H, 100);
HPLC (method 4): rt=2.43 min.

Example 71

1-{4-[(3-{[(5-Chloro-2-thienyl)carbonyl]amino}-2-hydroxypropyl)amino]phenyl}-L-prolinamide MS (ESI): m/z (%)=423 (M+H, 100);
HPLC (method 4): rt=2.51 min.

Example 72

5-Chloro-N-[2-hydroxy-3-({-4-[3-(hydroxymethyl)-1-piperidinyl]phenyl}-amino)propyl]-2-thiophenecarboxamide MS (ESI): m/z (%)=424 (M+H, 100);
HPLC (method 4): rt=2.43 min.

Example 73

5-Chloro-N-[2-hydroxy-3-({4-[2-(hydroxymethyl)-1-piperidinyl]phenyl}-amino)propyl]-2-thiophenecarboxamide MS (ESI): m/z (%)=424 (M+H, 100);
HPLC (method 4): rt=2.49 min.

Example 74

Ethyl 1-{-4-[(3-{[(5-chloro-2-thienyl)carbonyl]amino}-2-hydroxypropyl)-amino]phenyl}-2-piperidinecarboxylate MS (ESI): m/z (%)=466 (M+H, 100);
HPLC (method 4): rt=3.02 min.

Example 75

5-Chloro-N-[2-hydroxy-3-({4-[2-(hydroxymethyl)-1-pyrrolidinyl]phenyl}amino)-propyl]-2-thiophenecarboxamide MS (ESI): m/z (%)=410 (M+H, 100);
HPLC (method 4): rt=2.48 min.

Example 76

5-Chloro-N-(2-hydroxy-3-{[4-(2-methylhexahydro-5H-pyrrolo[3,4-d]isoxazol-5-yl)phenyl]amino}propyl)-2-thiophenecarboxamide MS (ESI): m/z (%)=437 (M+H, 100).
HPLC (method 5): rt=1.74 min.

Example 77

5-Chloro-N-(2-hydroxy-3-{[4-(1-pyrrolidinyl)-3-(trifluoromethyl)phenyl]-amino}propyl)-2-thiophenecarboxamide MS (ESI): m/z (%)=448 (M+H, 100);
HPLC (method 4): rt=3.30 min.

Example 78

5-Chloro-N-(2-hydroxy-3-{[4-(2-oxo-1-pyrrolidinyl)-3-(trifluoromethyl)phenyl]-amino}propyl)-2-thiophenecarboxamide MS (ESI): m/z (%)=462 (M+H, 100);
HPLC (method 4): rt=3.50 min.

Example 79

5-Chloro-N-(3-{[3-chloro-4-(3-oxo-4-morpholinyl)phenyl]amino}-2-hydroxypropyl)-2-thiophenecarboxamide MS (ESI): m/z (%)=444 (M+H, 100);
HPLC (method 4): rt=3.26 min.

Example 80

5-Chloro-N-(2-hydroxy-3-{[4-(3-oxo-4-morpholinyl)-3-(trifluoromethyl)phenyl]-amino}propyl)-2-thiophenecarboxamide MS (ESI): (%)=478 (M+H, 100);
HPLC (method 4): rt=3.37 min.

Example 81

5-Chloro-N-(2-hydroxy-3-{[3-methyl-4-(3-oxo-4-morpholinyl)phenyl]amino}-propyl)-2-thiophenecarboxamide MS (ESI): m/z (%)=424 (M+H, 100);
HPLC (method 4): rt=2.86 min.

Example 82

5-Chloro-N-(3-{[3-cyano-4-(3-oxo-4-morpholinyl)phenyl]amino}-2-hydroxypropyl)-2-thiophenecarboxamide MS (ESI): m/z (%)=435 (M+H, 100);
HPLC (method 4): rt=3.10 min.

Example 83

5-Chloro-N-(3-{[3-chloro-4-(1-pyrrolidinyl)phenyl]amino}-2-hydroxypropyl)-2-thiophenecarboxamide MS (EST): m/z (%)=414 (M+H, 100);
HPLC (method 4): rt=2.49 min.

Example 84

5-Chloro-N-(3-{[3-chloro-4-(2-oxo-1-pyrrolidinyl)phenyl]amino}-2-hydroxypropyl)-2-thiophenecarboxamide MS (ESI): m/z (%)=428 (M+H, 100);
HPLC (method 4): rt=3.39 min.

Example 85

5-Chloro-N-(3-{[3,5-dimethyl-4-(3-oxo-4-morpholinyl)phenyl]amino}-2-hydroxypropyl)-2-thiophenecarboxamide MS (ESI): m/z (%)=438 (M+H, 100);
HPLC (method 4): rt=2.84 min.

Example 86

N-(3-{[3-(Aminocarbonyl)-4-(4-morpholinyl)phenyl]amino}-2-hydroxypropyl)-5-chloro-2-thiophenecarboxamide MS (ESI): m/z (%)=439 (M+H, 100);
HPLC (method 4): rt=2.32 min.

Example 87

5-Chloro-N-(2-hydroxy-3-{[3-methoxy-4-(4-morpholinyl)phenyl]amino}propyl)-2-thiophenecarboxamide MS (ESI): m/z (%)=426 (M+H, 100);
HPLC (method 4): rt=2.32 min

Example 88

N-(3-{[3-Acetyl-4-(4-morpholinyl)phenyl]amino}-2-hydroxypropyl)-5-chloro-2-thiophenecarboxamide
MS (ESI): m/z (%)=438 (M+H, 100);
HPLC (method 4): rt=2.46 min.

Example 89

N-(3-{[3-Amino-4-(3-oxo-4-morpholinyl)phenyl]amino}-2-hydroxypropyl)-5-chloro-2-thiophenecarboxamide MS (ESI): m/z (%)=425 (M+H, 100);
HPLC (method 4): rt=2.45 min.

Example 90

5-Chloro-N-(3-{[3-chloro-4-(2-methyl-3-oxo-4-morpholinyl)phenyl]amino}-2-hydroxypropyl)-2-thiophenecarboxamide MS (ESI): m/z (%)=458 (M+H, 100);
HPLC (method 4): rt=3.44 min.

Example 91

5-Chloro-N-(3-{[3-chloro-4-(2-methyl-5-oxo-4-morpholinyl)phenyl]amino}-2-hydroxypropyl)-2-thiophenecarboxamide MS (ESI): m/z (%)=458 (M+H, 100);
HPLC (method 4): rt=3.48 min.

Example 91a

5-Chloro-N-[2-hydroxy-3-({4-[(3-oxo-4-morpholinyl)methyl]phenyl}amino)-propyl]-2-thiophenecarboxamide starting from 4-(4-amino-benzyl)-3-morpholinone (Surrey et al.; J. Amer. Chem. Soc.; 77; 1955; 633):

MS (ESI): m/z (%)=424 (M+H, 100);
HPLC (method 4): rt=2.66 min.

General method for preparing 3-substituted 5-chloro-N-[(2-oxo-1,3-oxazolidin-5-yl)methyl]-2-thiophenecarboxamide derivatives starting from substituted N-(3-amino-2-hydroxypropyl)-5-chloro-2-thiophenecarboxamide derivatives

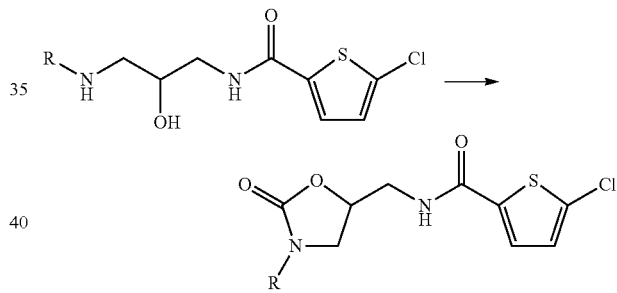

At room temperature, carbodiimidazole (1.2 to 1.8 eq.) or a similar phosgene equivalent are added to a solution of the substituted N-(3-amino-2-hydroxypropyl)-5-chloro-2-thiophenecarboxamide derivative (1.0 eq.) in absolute THF (about 0.1 mol/l). At room temperature or, if appropriate, at elevated temperature (up to 70° C.), the mixture is stirred for 2 to 18 h and then concentrated under reduced pressure. The product can be purified by silica gel chromatography (dichloromethane/methanol mixtures or cyclohexane/ethyl acetate mixtures).

The following compounds were prepared in an analogous manner:

Example 27

N-[3-Benzyl-2-oxo-1,3-oxazolidin-5-yl)methyl]-5-chloro-2-thiophenecarboxamide

MS (DCI, NH$_4$): m/z (%)=372 (M+Na, 100), 351 (M+H, 45);
HPLC (method 1): rt (%)=4.33 min (100).

Example 28

5-Chloro-N-{[3-(3-cyanophenyl)-2-oxo-1,3-oxazolidin-5-yl]methyl}-2-thiophenecarboxamide MS (DCI, NH$_4$): m/z (%)=362 (M+H, 42), 145 (100);
HPLC (method 2): rt (%)=4.13 min (100).

Example 29

5-Chloro-N-({3-[4-(cyanomethyl)phenyl]-2-oxo-1,3-oxazolidin-5-yl}methyl)-2-thiophenecarboxamide MS (ESI): m/z (%)=376 (M+H, 100);
HPLC (method 4): rt=4.12 min

Example 30

5-Chloro-N-({3-[3-(cyanomethyl)phenyl]-2-oxo-1,3-oxazolidin-5-yl}methyl)-2-thiophenecarboxamide MS (ESI): m/z (%)=376 (M+H, 100);
HPLC (method 4): rt=4.17 min

Example 92 tert-Butyl 4-[5-({[(5-chloro-2-thienyl)carbonyl]amino}methyl)-2-oxo-1,3-oxazolidin-3-yl]benzylcarbamate starting from Example 58:
MS (ESI): m/z (%)=488 (M+Na, 23), 349 (100);
HPLC (method 1): rt (%)=4.51 (98.5).

Example 93 tert-Butyl 4-[5-({[(5-chloro-2-thienyl)carbonyl]amino}methyl)-2-oxo-1,3-oxazolidin-3-yl] phenylcarbamate starting from Example 59:
MS (ESI): m/z (%)=493 (M+Na, 70), 452 (M+H, 10), 395 (100);
HPLC (method 1): rt (%)=4.41 (100).

Example 94 tert-Butyl 2-oxo-3-[4-(2-oxo-1-pyrrolidinyl)phenyl]-1,3-oxazolidin-5-yl}methylcarbamate starting from Example 60:
MS (DCI, NH$_3$): m/z (%)=393 (M+NH$_4$, 100);
HPLC (method 3): rt (%)=3.97 (100).

Example 95

5-Chloro-N-({3-[3-fluoro-4-(3-oxo-4-morpholinyl)phenyl]-2-oxo-1,3-oxazolidin-5-yl}methyl)-2-thiophenecarboxamide

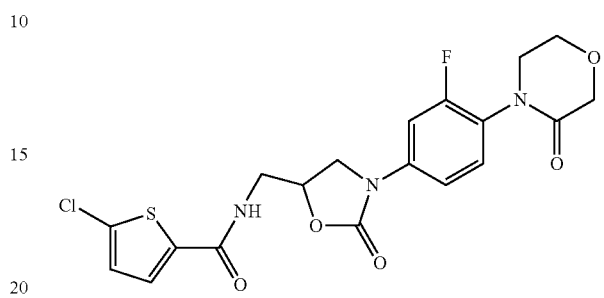

260 mg (0.608 mmol) of 5-chloro-N-(3-{[3-fluoro-4-(3-oxo-4-morpholinyl)phenyl]-amino}-2-hydroxypropyl)-2-thiophenecarboxamide (from Example 61), 197 mg (1.22 mmol) of carbonylimidazole and 7 mg of dimethylaminopyridine in 20 ml of dioxane are boiled under reflux for 5 hours. 20 ml of acetonitrile are then added, and the mixture is stirred in a closed vessel in a microwave oven at 180° C. for 30 minutes. The solution is concentrated using a rotary evaporator and chromatographed on an RP-HPLC column. This gives 53 mg (19% of theory) of the target compound.

NMR (300 MHz, d$_6$-DMSO): δ=3.6-3.7 (m, 4H), 3.85 (dd, 1H), 3.95 (m, 2H), 4.2 (m, 1H), 4.21 (s, 2H), 4.85 (m, 1H), 4.18 (s, 2H), 7.19 (d, 1H, thiophene), 7.35 (dd, 1H), 7.45 (t, 1H), 7.55 (dd, 1H), 7.67 (d, 1H, thiophene), 8.95 (t, 1H, CONH).

Example 96

5-Chloro-N-[(2-oxo-3-phenyl-1,3-oxazolidin-5-yl)methyl]-2-thiophenecarboxamide starting from Example 62:
MS (ESI): m/z (%)=359 ([M+Na]$^+$, 71), 337 ([M+H]$^+$, 100), Cl pattern;
HPLC (method 3): rt (%)=4.39 (100).
IC$_{50}$: 2 μM

Example 97

5-Chloro-N-({2-oxo-3-[4-(3-oxo-4-morpholinyl)phenyl]-1,3-oxazolidin-5-yl}-methyl)-2-thiophenecarboxamide starting from Example 63:
MS (ESI): m/z (%)=458 ([M+Na]$^+$, 66), 436 ([M+H]$^+$, 100), Cl pattern;
HPLC (method 3): rt (%)=3.89 (100).
IC$_{50}$: 1.4 nM

Example 98

N-[(3-{4-[Acetyl(cyclopropyl)amino]phenyl}-2-oxo-1,3-oxazolidin-5-yl)methyl]-5-chloro-2-thiophenecarboxamide starting from Example 64:
MS (ESI): m/z (%)=456 ([M+Na]$^+$, 55), 434 ([M+H]$^+$, 100), Cl pattern;
HPLC (method 3): rt (%)=4.05 (100).
IC$_{50}$: 50 nM

Example 99

N-[(3-{4-[Acetyl(methyl)amino]phenyl}-2-oxo-1,3-oxazolidin-5-yl)methyl]-5-chloro-2-thiophenecarboxamide MS (ESI): m/z (%)=408 (M+H, 30), 449 (M+H+MeCN, 100);
HPLC (method 4): rt=3.66 min.

Example 100

5-Chloro-N-({2-oxo-3-[4-(1H-1,2,3-triazol-1-yl)phenyl]-1,3-oxazolidin-5-yl}-methyl)-2-thiophenecarboxamide MS (ESI): m/z (%)=404 (M+H, 45), 445 (M+H+MeCN, 100);
HPLC (method 4): rt=3.77 min.

Example 101

Tert-butyl 1-{4-[5-({[(5-chloro-2-thienyl)carbonyl]amino}methyl)-2-oxo-1,3-oxazolidin-3-yl]phenyl}-L-prolinate MS (ESI): m/z (%)=450 (M+H-56, 25), 506 (M+H, 100);
HPLC (method 4): rt=5.13 min

Example 102

1-{4-[5-({[(5-Chloro-2-thienyl)carbonyl]amino}methyl)-2-oxo-1,3-oxazolidin-3-yl]phenyl}-4-piperidinecarboxamide MS (ESI): m/z (%)=463 (M+H, 100);
HPLC (method 4): rt=2.51 min.

Example 103

1-{4-[5-({[(5-Chloro-2-thienyl)carbonyl]amino}methyl)-2-oxo-1,3-oxazolidin-3-yl]phenyl}-3-piperidinecarboxamide MS (ESI): m/z (%)=463 (M+H, 100);
HPLC (method 4): rt=2.67 min.

Example 104

5-Chloro-N-({2-oxo-3-[4-(4-oxo-1-piperidinyl)phenyl]-1,3-oxazolidin-5-yl}methyl)-2-thiophenecarboxamide MS (ESI): m/z (%)=434 (M+H, 40), 452 (M+H+H$_2$O, 100), 475 (M+H+MeCN, 60);
HPLC (method 4): rt=3.44 min.

Example 105

1-{4-[5-({[(5-Chloro-2-thienyl)carbonyl]amino}methyl)-2-oxo-1,3-oxazolidin-3-yl]phenyl}-L-prolinamide MS (ESI): m/z (%)=449 (M+H, 100);
HPLC (method 4): rt=3.54 min.

Example 106

5-Chloro-N-[(3-{4-[3-(hydroxymethyl)-1-piperidinyl]phenyl}-2-oxo-1,3-oxazolidin-5-yl)methyl]-2-thiophenecarboxamide MS (ESI): m/z (%)=450 (M+H, 100);
HPLC (method 5): rt=2.53 min.

Example 107

5-Chloro-N-[(3-{4-[2-(hydroxymethyl)-1-piperidinyl]phenyl}-2-oxo-1,3-oxazolidin-5-yl)methyl]-2-thiophenecarboxamide MS (ESI): m/z (%)=450 (M+H, 100);
HPLC (method 5): rt=2.32 min.

Example 108

Ethyl 1-{4-[5-({[(5-chloro-2-thienyl)carbonyl]amino}methyl)-2-oxo-1,3-oxazolin-3-yl]phenyl}-2-piperidinecarboxylate MS (ESI): m/z (%)=492 (M+H, 100);
HPLC (method 5): rt=4.35 min.

Example 109

5-Chloro-N-[(3-{4-[2-(hydroxymethyl)-1-pyrrolidinyl]phenyl}-2-oxo-1,3-oxazolidin-5-yl)methyl]-2-thiophenecarboxamide MS (ESI): m/z (%)=436 (M+H, 100);
HPLC (method 4): rt=2.98 min.

Example 110

5-Chloro-N-({2-oxo-3-[4-(1-pyrrolidinyl)-3-(trifluoromethyl)phenyl]-1,3-oxazolidin-5-yl}methyl)-2-thiophenecarboxamide MS (ESI): m/z (%)=474 (M+H, 100);
HPLC (method 4): rt=4.63 min.

Example 111

5-Chloro-N-({3-[4-(2-methylhexahydro-5H-pyrrolo[3,4-d]isoxazol-5-yl)phenyl]-2-oxo-1,3-oxazolidin-5-yl}methyl)-2-thiophenecarboxamide MS (ESI): m/z (%)=463 (M+H, 100);
HPLC (method 4): rt=2.56 min.

Example 112

5-Chloro-N-({2-oxo-3-[4-(2-oxo-1-pyrrolidinyl)-3-(trifluoromethyl)phenyl]-1,3-oxazolidin-5-yl}methyl)-2-thiophenecarboxamide MS (ESI): m/z (%)=488 (M+H, 100);
HPLC (method 4): rt=3.64 min.

Example 113

5-Chloro-N-({3-[3-chloro-4-(3-oxo-4-morpholinyl)phenyl]-2-oxo-1,3-oxazolidin-5-yl}methyl)-2-thiophenecarboxamide MS (ESI): m/z (%)=470 (M+H, 100);
HPLC (method 4): rt=3.41 min.

Example 114

5-Chloro-N-({2-oxo-3-[4-(3-oxo-4-morpholinyl)-3-(trifluoromethyl)phenyl]-1,3-oxazolidin-5-yl}methyl)-2-thiophenecarboxamide MS (ESI): m/z (%)=504 (M+H, 100);
HPLC (method 4): rt=3.55 min.

Example 115

5-Chloro-N-({3-[3-methyl-4-(3-oxo-4-morpholinyl)phenyl]-2-oxo-1,3-oxazolidin-5-yl}methyl)-2-thiophenecarboxamide MS (ESI): m/z (%)=450 (M+H, 100);
HPLC (method 4): rt=3.23 min.

Example 116

5-Chloro-N-({3-[3-cyano-4-(3-oxo-4-morpholinyl)phenyl]-2-oxo-1,3-oxazolidin-5-yl}methyl)-2-thiophenecarboxamide MS (ESI): m/z (%)=461 (M+H, 100);
HPLC (method 4): rt=3.27 min.

Example 117

5-Chloro-N-({3-[3-chloro-4-(1-pyrrolidinyl)phenyl]-2-oxo-1,3-oxazolidin-5-yl}methyl)-2-thiophenecarboxamide MS (ESI): m/z (%)=440 (M+H, 100);
HPLC (method 4): rt=3.72 min.

Example 118

5-Chloro-N-({3-[3-chloro-4-(2-oxo-1-pyrrolidinyl)phenyl]-2-oxo-1,3-oxazolidin-5-yl}methyl)-2-thiophenecarboxamide MS (ESI): m/z (%)=454 (M+H, 100);
HPLC (method 4): rt=3.49 min.

Example 119

5-Chloro-N-({3-[3,5-dimethyl-4-(3-oxo-4-morpholinyl)phenyl]-2-oxo-1,3-oxazolidin-5-yl}methyl)-2-thiophenecarboxamide MS (ESI): m/z (%)=464 (M+H, 100);
HPLC (method 4): rt=3.39 min.

Example 120

N-({3-[3-(Aminocarbonyl)-4-(4-morpholinyl)phenyl]-2-oxo-1,3-oxazolidin-5-yl}methyl)-5-chloro-2-thiophenecarboxamide MS (ESI): m/z (%)=465 (M+H, 100);
HPLC (method 4): rt=3.07 min.

Example 121

5-Chloro-N-({3-[3-methoxy-4-(4-morpholinyl)phenyl]-2-oxo-1,3-oxazolidin-5-yl}methyl)-2-thiophenecarboxamide MS (ESI): m/z (%)=452 (M+H, 100);
HPLC (method 4): rt=2.86 min.

Example 122

N-({3-[3-Acetyl-4-(4-morpholinyl)phenyl]-2-oxo-1,3-oxazolidin-5-yl}methyl)-5-chloro-2-thiophenecarboxamide MS (ESI): m/z (%)=464 (M+H, 100);
HPLC (method 4): rt=3.52 min.

Example 123

N-({3-[3-Amino-4-(3-oxo-4-morpholinyl)phenyl]-2-oxo-1,3-oxazolidin-5-yl}-methyl)-5-chloro-2-thiophenecarboxamide MS (ESI): m/z (%)=451 (M+H, 100);
HPLC (method 6): rt=3.16 min.

Example 124

5-Chloro-N-({3-[3-chloro-4-(2-methyl-3-oxo-4-morpholinyl)phenyl]-2-oxo-1,3-oxazolidin-5-yl}methyl)-2-thiophenecarboxamide MS (ESI): m/z (%)=484 (M+H, 100);
HPLC (method 4): rt=3.59 min.

Example 125

5-Chloro-N-({3-[3-chloro-4-(2-methyl-5-oxo-4-morpholinyl)phenyl]-2-oxo-1,3-oxazolidin-5-yl}methyl)-2-thiophenecarboxamide MS (ESI): m/z (%)=484 (M+H, 100);
HPLC (method 4): rt=3.63 min.

Example 125a

5-Chloro-N-[(2-oxo-3-{4-[(3-oxo-4-morpholinyl)methyl]phenyl}-1,3-oxazolidin-5-yl)methyl]-2-thiophenecarboxamide MS (ESI): m/z (%)=450 (M+H, 100);
HPLC (method 4): rt=3.25 min.

Via epoxide opening with an amine and subsequent cyclization to give the corresponding oxazolidinone, it was also possible to prepare the following compounds:

| Example No. | Structure | M.p. [° C.] | IC$_{50}$ [μM] |
|---|---|---|---|
| 126 | 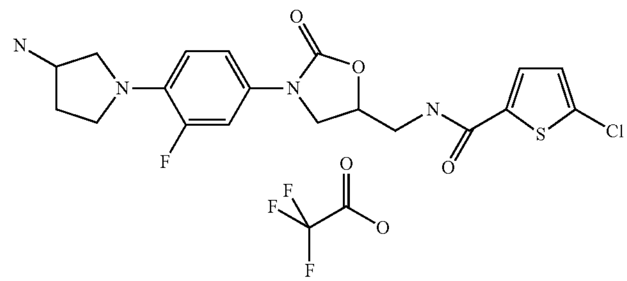 | 229Z | 0.013 |
| 127 | 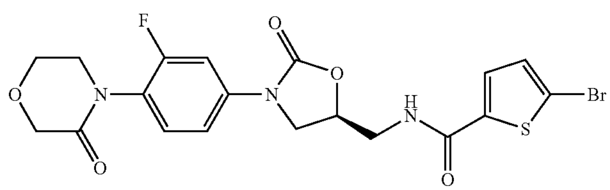 [SMILES: O=C(NC[C@H]1CN(c2ccc(N3CCOCC3=O)c(F)c2)C(=O)O1)c1ccc(Br)s1] | 159 | 0.0007 |
| 128 | 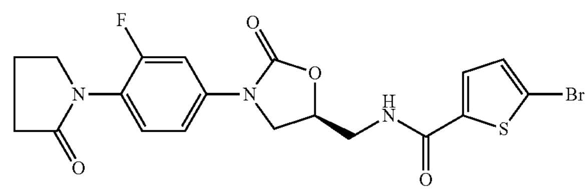 [SMILES: O=C(NC[C@H]1CN(c2ccc(N3CCCC3=O)c(F)c2)C(=O)O1)c1ccc(Br)s1] | 198 | 0.002 |
| 129 | 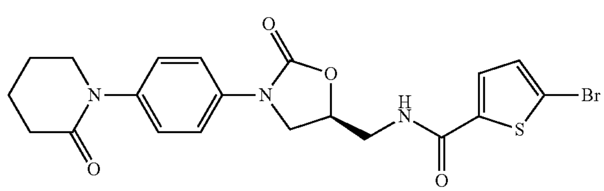 [SMILES: O=C(NC[C@H]1CN(c2ccc(N3CCCCC3=O)cc2)C(=O)O1)c1ccc(Br)s1] | 196 | 0.001 |
| 130 | 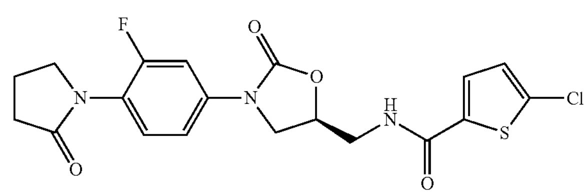 [SMILES: O=C(NC[C@H]1CN(c2ccc(N3CCCC3=O)c(F)c2)C(=O)O1)c1ccc(Cl)s1] | 206 | 0.0033 |
| 130a | 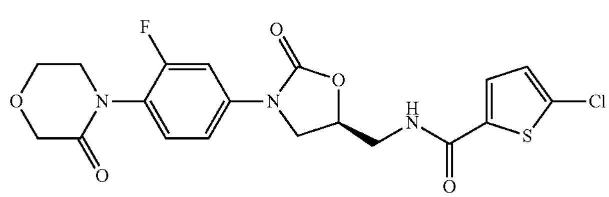 [SMILES: O=C(NC[C@H]1CN(c2ccc(N3CCOCC3=O)c(F)c2)C(=O)O1)c1ccc(Cl)s1] | 194 | |

-continued

| Example No. | Structure | M.p. [° C.] | IC$_{50}$ [μM] |
|---|---|---|---|
| 131 | 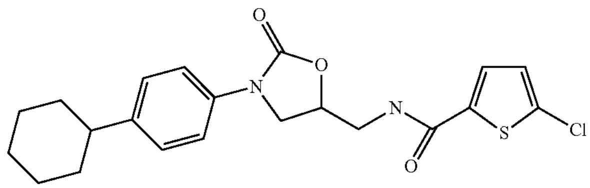 [SMILES: O=C(NCC1CN(c2ccc(C3CCCCC3)cc2)C(=O)O1)c1ccc(Cl)s1] | 195 | 0.85 |
| 132 | 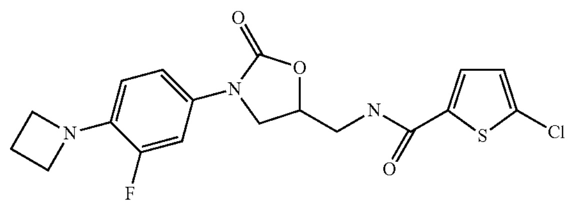 [SMILES: O=C(NCC1CN(c2ccc(N3CCC3)c(F)c2)C(=O)O1)c1ccc(Cl)s1] | 206 | 0.12 |
| 133 | 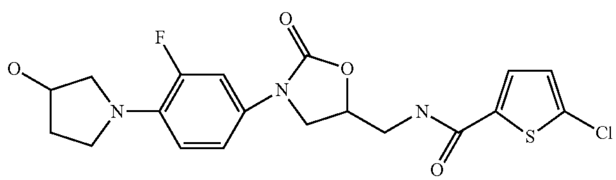 [SMILES: O=C(NCC1CN(c2ccc(N3CCC(O)C3)c(F)c2)C(=O)O1)c1ccc(Cl)s1] | 217 | 0.062 |
| 134 | from 1-(4-amino-phenyl)-piperidin-3-ol (Tong, L. K. J. et al.; J. Amer. Chem. Soc 1960; 82, 1988). | 207 | 0.48 |
| 135 | 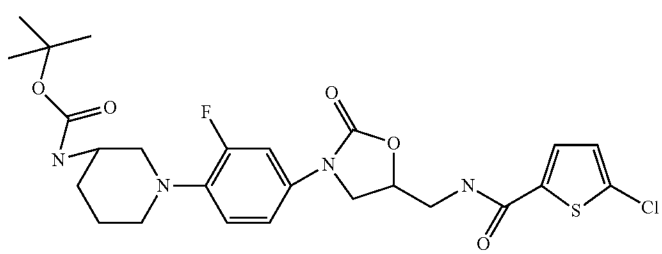 [SMILES: CC(C)(C)OC(=O)NC1CCCN(c2ccc(N3CC(CNC(=O)c4ccc(Cl)s4)OC3=O)cc2F)C1] | 202 | 1.1 |
| 136 | | 239 | 1.2 |

| Example No. | Structure | M.p. [° C.] | IC$_{50}$ [μM] |
|---|---|---|---|
| 137 | 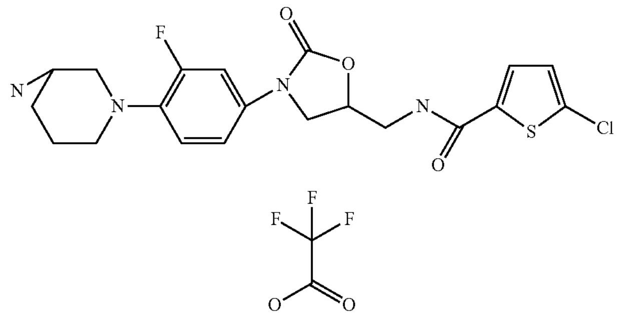 [SMILES: NC1CCCN(c2ccc(N3CC(CNC(=O)c4ccc(Cl)s4)OC3=O)cc2F)C1 ; O=C(O)C(F)(F)F] | 219 | 0.044 |
| 138 | 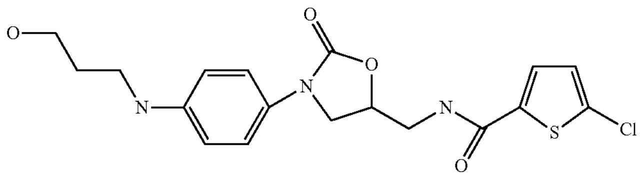 [SMILES: O=C(NCC1CN(c2ccc(NCCCO)cc2)C(=O)O1)c1ccc(Cl)s1] | 95 | 0.42 |
| 139 | 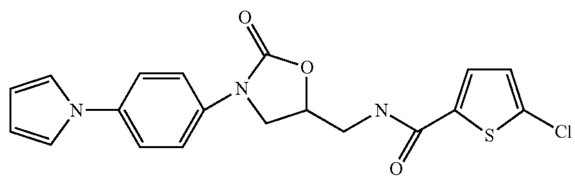 [SMILES: O=C(NCC1CN(c2ccc(-n3cccc3)cc2)C(=O)O1)c1ccc(Cl)s1] | 217 | 1.7 |

Examples 14 to 16 below are working examples for the optional oxidation step.

Example 14

5-Chloro-N-({(5S)-3-[3-fluoro-4-(1-oxo-1[lambda]$^4$, 4-thiazinan-4-yl)phenyl]-2-oxo-1,3-oxazolidin-5-yl}methyl)-2-thiophenecarboxamide

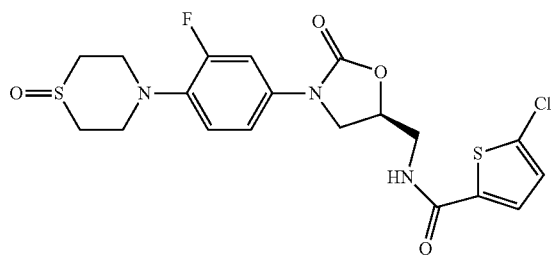 [SMILES: O=C(NC[C@H]1CN(c2ccc(N3CCS(=O)CC3)c(F)c2)C(=O)O1)c1ccc(Cl)s1]

At 0° C., 5-chloro-N-({(5S)-3-[3-fluoro-4-(1,4-thiazinan-4-yl)phenyl]-2-oxo-1,3-oxazolidin-5-yl}methyl)-2-thiophenecarboxamide (0.1 g, 0.22 mmol) from Example 3 in methanol (0.77 ml) is added to a solution of sodium periodate (0.05 g, 0.23 mmol) in water (0.54 ml), and the mixture is stirred at 0° C. for 3 h. 1 ml of DMF is then added, and the mixture is stirred at RT for 8 h. After addition of a further 50 mg of sodium periodate, the mixture is once more stirred at RT overnight. The mixture is then admixed with 50 ml of water, and the insoluble product is filtered off with suction. Washing with water and drying gives 60 mg (58% of theory) of crystals.

M.p.: 257° C.;

R$_f$ (silica gel, toluene/ethyl acetate 1:1)=0.54 (starting material=0.46);

IC$_{50}$ value=1.1 μM;

MS (DCI) 489 (M+NH$_4$), Cl pattern.

Example 15

Preparation of 5-chloro-N-({(5S)-3-[4-(1,1-dioxo-1[lambda]$^6$,4-thiazinan-4-yl)-3-fluorophenyl]-2-oxo-1,3-oxazolidin-5-yl}methyl)-2-thiophenecarboxamide

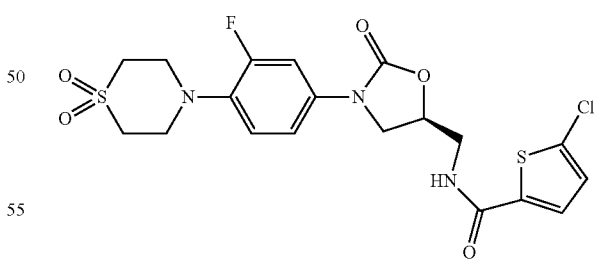

5-Chloro-N-({(5S)-3-[3-fluoro-4-(1,4-thiazinan-4-yl)phenyl]-2-oxo-1,3-oxazolidin-5-yl}methyl)-2-thiophenecarboxamide from Example 3 (0.1 g, 0.22 mmol) in 3.32 ml of a mixture of 1 part of water and 3 parts of acetone is admixed with 80 mg (0.66 mmol) of N-methylmorpholine N-oxide (NMO) and 0.1 ml of a 2.5% strength solution of osmium tetroxide in 2-methyl-2-propanol. The mixture is stirred at room temperature overnight, and another 40 mg of NMO are added. The mixture is stirred for a further night and

Example 16

5-Chloro-N-{[(5S)-3-(3-fluoro-4-morpholinophenyl)-2-oxo-1,3-oxazolidin-5-yl]methyl}-2-thiophenecarboxamide N-oxide is obtained by treating 5-chloro-N-{[(5S)-3-(3-fluoro-4-morpholinophenyl)-2-oxo-1,3-oxazolidin-5-yl]methyl}-2-thiophenecarboxamide from Example 1 with the magnesium salt of monoperoxyphthalic acid.

MS (ESI): 456 (M+H, 21%, Cl pattern), 439 (100%).

The Examples 31 to 35 and 140 to 147 below refer to the optional amidination step.

General method for preparing amidines and amidine derivatives starting from cyanomethylphenyl-substituted 5-chloro-N-[(2-oxo-1,3-oxazolidin-5-yl)methyl]-2-thiophenecarboxamide derivatives The cyanomethylphenyl-substituted 5-chloro-N-[(2-oxo-1,3-oxazolidin-5-yl)methyl]-2-thiophenecarboxamide derivative in question (1.0 eq.) is, together with triethylamine (8.0 eq.), stirred at RT in a saturated solution of hydrogen sulphide in pyridine (about 0.05-0.1 mol/l) for one to two days. The reaction mixture is diluted with ethyl acetate (EtOAc) and washed with 2 N hydrochloric acid. The organic phase is dried with $MgSO_4$, filtered and concentrated under reduced pressure.

The crude product is dissolved in acetone (0.01-0.1 mol/l) and admixed with methyl iodide (40 eq.). The reaction mixture is stirred at room temperature (RT) for 2 to 5 h and then concentrated under reduced pressure.

The residue is dissolved in methanol (0.01-0.1 mol/l) and, to prepare the unsubstituted amidines, admixed with ammonium acetate (3 eq.) and ammonium chloride (2 eq.). To prepare the substituted amidine derivatives, primary or secondary amines (1.5 eq.) and acetic acid (2 eq.) are added to the methanolic solution. After 5-30 h, the solvent is removed under reduced pressure and the residue is purified by chromatography over an RP8 silica gel column (water/acetonitrile 9/1-1/1+0.1% trifluoroacetic acid).

The following compounds were prepared in an analogous manner:

Example 31

N-({3-[4-(2-Amino-2-iminoethyl)phenyl]-2-oxo-1,3-oxazolidin-5-yl}methyl)-5-chloro-2-thiophenecarboxamide MS (ESI): m/z (%)=393 (M+H, 100);
HPLC (method 4): rt=2.63 min

Example 32

5-Chloro-N-({3-[3-(4,5-dihydro-1H-imidazol-2-ylmethyl)phenyl]-2-oxo-1,3-oxazolidin-5-yl}methyl)-2-thiophenecarboxamide MS (ESI): m/z (%)=419 (M+H, 100);
HPLC (method 4): rt=2.61 min

Example 33

5-Chloro-N-[3-{3-[2-imino-2-(4-morpholinyl)ethyl]phenyl}-2-oxo-1,3-oxazolidin-5-yl)methyl]-2-thiophenecarboxamide MS (ESI): m/z (%)=463 (M+H, 100);
HPLC (method 4): rt=2.70 min

Example 34

5-Chloro-N-[(3-{3-[2-imino-2-(1-pyrrolidinyl)ethyl]phenyl}-2-oxo-1,3-oxazolidin-5-yl)methyl]-2-thiophenecarboxamide MS (ESI): m/z (%)=447 (M+H, 100);
HPLC (method 4): rt=2.82 min

Example 35

N-({3-[3-(2-Amino-2-iminoethyl)phenyl]-2-oxo-1,3-oxazolidin-5-yl}methyl)-5-chloro-2-thiophenecarboxamide MS (ESI): m/z (%)=393 (M+H, 100);
HPLC (method 4): rt=2.60 min

Example 140

5-Chloro-N-({3-[4-(4,5-dihydro-1H-imidazol-2-ylmethyl)phenyl]-2-oxo-1,3-oxazolidin-5-yl}methyl)-2-thiophenecarboxamide MS (ESI): m/z (%)=419 (M+H, 100);
HPLC (method 4): rt=2.65 min

Example 141

5-Chloro-N-[(3-{4-[2-imino-2-(4-morpholinyl)ethyl]phenyl}-2-oxo-1,3-oxazolidin-5-yl)methyl]-2-thiophenecarboxamide MS (ESI): m/z (%)=463 (M+H, 100);
HPLC (method 4): rt=2.65 min

Example 142

5-Chloro-N-[(3-{4-[2-imino-2-(1-piperidinyl)ethyl]phenyl}-2-oxo-1,3-oxazolidin-5-yl)methyl]-2-thiophenecarboxamide MS (ESI): m/z (%)=461 (M+H, 100);
HPLC (method 4): rt=2.83 min

--- then poured into 50 ml of water and extracted three times with ethyl acetate. The organic phase gives, after drying and concentrating, 23 mg and the aqueous phase, after removal of the insoluble solid by filtration with suction, 19 mg (in total 39% of theory) of the target compound.

M.p.: 238° C.;
$R_f$ (toluene/ethyl acetate 1:1)=0.14 (starting material=0.46);
$IC_{50}$ value=210 nM;
MS (DCI): 505 (M+$NH_4$), Cl pattern.

Example 143

5-Chloro-N-[(3-{4-[2-imino-2-(1-pyrrolidinyl)ethyl]phenyl}-2-oxo-1,3-oxazolidin-5-yl)methyl]-2-thiophenecarboxamide MS (ESI): m/z (%)=447 (M+H, 100);
HPLC (method 4): rt=2.76 min

Example 144

5-Chloro-N-[(3-{4-[2-(cyclopentylamino)-2-iminoethyl]phenyl}-2-oxo-1,3-oxazolidin-5-yl)methyl]-2-thiophenecarboxamide MS (ESI): m/z (%)=461 (M+H, 100);
HPLC (method 4): rt=2.89 min

Example 145

5-Chloro-N-{[3-(4-{2-imino-2-[(2,2,2-trifluoroethyl)amino]ethyl}phenyl)-2-oxo-1,3-oxazolidin-5-yl]methyl}-2-thiophenecarboxamide MS (ESI): m/z (%)=475 (M+H, 100);
HPLC (method 4): rt=2.79 min

Example 146

N-({3-[4-(2-Anilino-2-iminoethyl)phenyl]-2-oxo-1,3-oxazolidin-5-yl}methyl)-5-chloro-2-thiophenecarboxamide
MS (ESI): m/z (%)=469 (M+H, 100);
HPLC (method 4): rt=2.83 min

Example 147

5-Chloro-N-[(3-{4-[2-imino-2-(2-pyridinylamino)ethyl]phenyl}-2-oxo-1,3-oxazolidin-5-yl)methyl]-2-thiophenecarboxamide MS (ESI): m/z (%)=470 (M+H, 100);
HPLC (method 4): rt=2.84 min Examples 148 to 151 below refer to the removal of BOC amino protective groups
General Method for Removing Boc Protective Groups (tert-butyloxycarbonyl):

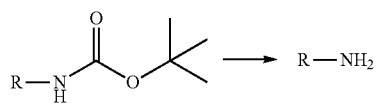

Aqueous trifluoroacetic acid (TFA, about 90%) is added dropwise to an ice-cooled solution of a tert-butyloxycarbonyl-(Boc) protected compound in chloroform or dichloromethane (about 0.1 to 0.3 mol/l). After about 15 min, ice-cooling is removed and the mixture is stirred at room temperature for approximately 2-3 h, and the solution is then concentrated and dried under high vacuum. The residue is taken up in dichloromethane or dichloromethane/methanol and washed with saturated sodium bicarbonate or 1N sodium hydroxide solution. The organic phase is washed with saturated sodium chloride solution, dried over a little magnesium sulphate and concentrated. If appropriate, purification is carried out by crystallization from ether or ether/dichloromethane mixtures.

The following compounds were prepared in an analogous manner from the corresponding Boc-protected precursors:

Example 148

N-({3-[4-(Aminomethyl)phenyl]-2-oxo-1,3-oxazolidin-5-yl}methyl)-5-chloro-2-thiophene-carboxamide starting from Example 92:
MS (ESI): m/z (%)=349 (M-NH$_2$, 25), 305 (100);
HPLC (method 1): rt (%)=3.68 (98).
IC$_{50}$: 2.2 µM

Example 149

N-{[3-(4-Aminophenyl)-2-oxo-1,3-oxazolidin-5-yl]methyl}-5-chloro-2-thiophenecarboxamide starting from Example 93:
MS (ESI): m/z (%)=352 (M+H, 25);
HPLC (method 1): rt (%)=3.50 (100).
IC$_{50}$: 2 µM An alternative enantiomerically pure synthesis of this compound is shown in the scheme below (cf. also Delalande S. A., DE 2836305, 1979; Chem. Abstr. 90, 186926):

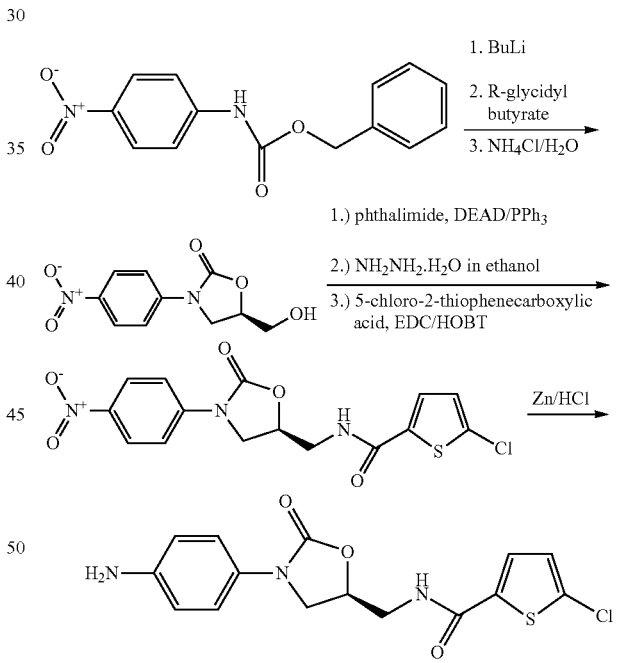

Example 150

5-Chloro-N-({3-[4-(glycylamino)phenyl]-2-oxo-1,3-oxazolidin-5-yl}methyl)-2-thiophenecarboxamide starting from Example 152:
MS (ES-pos): m/z (%)=408 (100);
HPLC (method 3): rt (%)=3.56 (97).
IC$_{50}$: 2 µM

Example 151

5-(Aminomethyl)-3-[4-(2-oxo-1-pyrrolidinyl)phenyl]-1,3-oxazolidin-2-one starting from Example 60:
MS (ESI): m/z (%)=276 (M+H, 100);
HPLC (method 3): rt (%)=2.99 (100).
IC$_{50}$: 2 μM The Examples 152 to 166 below refer to the amino group derivatization of aniline- or benzylamine-substituted oxazolidinones using various reagents:

Example 152

5-Chloro-N-({3-[4-(N-tert-butyloxycarbonyl-glycylamino)phenyl]-2-oxo-1,3-oxazolidin-5-yl}methyl)-2-thiophenecarboxamide

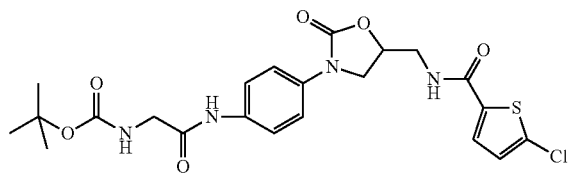 [SMILES: CC(C)(C)OC(=O)NCC(=O)Nc1ccc(N2CC(CNC(=O)c3ccc(Cl)s3)OC2=O)cc1]

At 0° C., 754 mg (2.1 mmol) of N-{[3-(4-aminophenyl)-2-oxo-1,3-oxazolidin-5-yl]methyl}-5-chloro-2-thiophenecarboxamide (from Example 149) are added to a solution of 751 mg (4.3 mmol) of Boc-glycine, 870 mg (6.4 mmol) of HOBT (1-hydroxy-1H-benzotriazole×H$_2$O), 1790 mg (4.7 mmol) of HBTU [O-(benzotriazol-1-yl)-N,N,N',N'-tetramethyluronium hexafluorophosphate] and 1.41 ml (12.9 mmol) of N-methylmorpholine in 15 ml of DMF/CH$_2$Cl$_2$ (1:1). The mixture is stirred at room temperature overnight and then diluted with water. The precipitated solid is filtered off and dried. Yield: 894 mg (79.7% of theory);
MS (DCI, NH$_3$): m/z (%)=526 (M+NH$_4$, 100);
HPLC (method 3): rt (%)=4.17 (97).

Example 153

N-[(3-{-4-[(Acetylamino)methyl]phenyl}-2-oxo-1,3-oxazolidin-5-yl)methyl]-5-chloro-2-thiophenecarboxamide

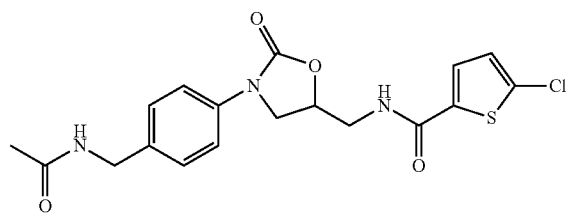 [SMILES: CC(=O)NCc1ccc(N2CC(CNC(=O)c3ccc(Cl)s3)OC2=O)cc1]

At 0° C., a mixture of 30 mg (0.082 mmol) of N-({3-[4-(aminomethyl)phenyl]-2-oxo-1,3-oxazolidin-5-yl}methyl)-5-chloro-2-thiophene-carboxamide (from Example 148) in 1.5 ml of absolute THF and 1.0 ml of absolute dichloromethane, and 0.02 ml of absolute pyridine is mixed with acetic anhydride (0.015 ml, 0.164 mmol). The mixture is stirred at room temperature overnight. Addition of ether and crystallization affords the product. Yield: 30 mg (87% of theory),
MS (ESI): m/z (%)=408 (M+H, 18), 305 (85);
HPLC (method 1): rt (%)=3.78 (97).
IC$_{50}$: 0.6 μM

Example 154

N-{[3-(4-{[(Aminocarbonyl)amino]methyl}phenyl)-2-oxo-1,3-oxazolidin-5-yl]-methyl}-5-chloro-2-thiophenecarboxamide

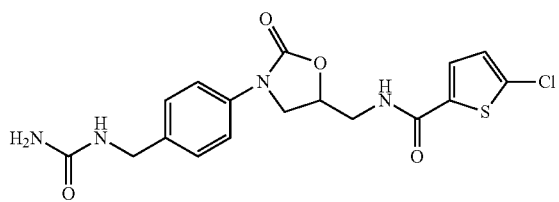 [SMILES: NC(=O)NCc1ccc(N2CC(CNC(=O)c3ccc(Cl)s3)OC2=O)cc1]

At room temperature, 0.19 ml (0.82 mmol) of trimethylsilylisocyanate are added dropwise to a mixture of 30 mg (0.082 mmol) of N-({3-[4-(aminomethyl)phenyl]-2-oxo-1,3-oxazolidin-5-yl}methyl)-5-chloro-2-thiophene-carboxamide (from Example 148) in 1.0 ml of dichloromethane. The mixture is stirred overnight and, after addition of ether, the product is then obtained by filtration. Yield: 21.1 mg (52% of theory),
MS (ESI): m/z (%)=409 (M+H, 5), 305 (72);
HPLC (method 1): rt (%)=3.67 (83).
IC$_{50}$: 1.3 μM General method for acylating N-{[3-(4-aminophenyl)-2-oxo-1,3-oxazolidin-5-yl]methyl}-5-chloro-2-thiophenecarboxamide with carbonyl chlorides

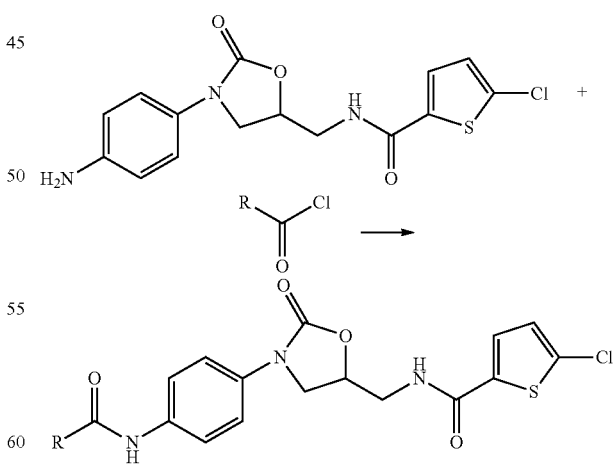

Under argon, an approximately 0.1 molar solution of N-{[3-(4-aminophenyl)-2-oxo-1,3-oxazolidin-5-yl]methyl}-5-chloro-2-thiophenecarboxamide (from Example 149) (1.0 eq.) in absolute dichloromethane/pyridine (19:1) is added dropwise to the appropriate acid chloride (2.5 eq.). The mixture is stirred overnight and then admixed with about 5 eq. of PS trisamine (Argonaut Technologies) and 2 ml of absolute dichloromethane. The mixture is stirred gently for 1 h and then filtered off, and the filtrate is concentrated. If appropriate, the products are purified by preparative RP-HPLC.

The following compounds were prepared in an analogous manner:

Example 155

N-({3-[4-(Acetylamino)phenyl]-2-oxo-1,3-oxazolidin-5-yl}methyl)-5-chloro-2-thiophene-carboxamide LC-MS: m/z (%)=394 (M+H, 100);
LC-MS (method 6): rt (%)=3.25 (100).
$IC_{50}$: 1.2 µM

Example 156

5-Chloro-N-[(2-oxo-3-{4-[(2-thienylcarbonyl)amino]phenyl}-1,3-oxazolidin-5-yl)methyl]-2-thiophenecarboxamide LC-MS: m/z (%)=462 (M+H, 100);
LC-MS (method 6): rt (%)=3.87 (100).
$IC_{50}$: 1.3 µM

Example 157

5-Chloro-N-[(3-{4-[(methoxyacetyl)amino]phenyl}-2-oxo-1,3-oxazolidin-5-yl)-methyl]-2-thiophenecarboxamide LC-MS: m/z (%)=424 (M+H, 100);
LC-MS (method 6): rt (%)=3.39 (100).
$IC_{50}$: 0.73 µM

Example 158

N-{4-[5-({[(5-Chloro-2-thienyl)carbonyl]amino}methyl)-2-oxo-1,3-oxazolidin-3-yl]phenyl}-3,5-dimethyl-4-isoxazolecarboxamide LC-MS: m/z (%)=475 (M+H, 100).
$IC_{50}$: 0.46 µM

Example 159

5-Chloro-N-{[3-(4-{[(3-chloropropyl)sulphonyl]amino}phenyl)-2-oxo-1,3-oxazolidin-5-yl]methyl}-2-thiophenecarboxamide

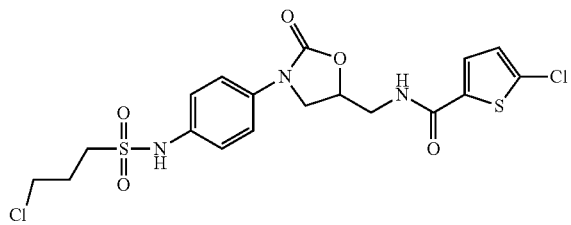 [SMILES: O=C(NCC1CN(c2ccc(NS(=O)(=O)CCCCl)cc2)C(=O)O1)c1ccc(Cl)s1]

An ice-cooled solution of 26.4 mg (0.15 mmol) of 3-chloro-1-propanesulphonyl chloride and 0.03 ml (0.2 mmol) of triethylamine in 3.5 ml of absolute dichloromethane is admixed with 35 mg (0.1 mmol) of N-{[3-(4-aminophenyl)-2-oxo-1,3-oxazolidin-5-yl]-methyl}-5-chloro-2-thiophene-carboxamide (from Example 149). After 30 min, ice-cooling is removed and the mixture is stirred at room temperature overnight, and 150 mg (about 5.5 eq.) of PS-trisamine (Argonaut Technologies) and 0.5 ml of dichloromethane are then added. The suspension is stirred gently for 2 h and filtered (the resin is washed with dichloromethane/methanol), and the filtrate is concentrated. The product is purified by preparative RP-HPLC. Yield: 19.6 mg (40% of theory), LC-MS: m/z (%)=492 (M+H, 100);
LC-MS (method 5): rt (%)=3.82 (91).
$IC_{50}$: 1.7 µM

Example 160

5-Chloro-N-({3-[4-(1,1-dioxido-2-isothiazolidinyl)phenyl]-2-oxo-1,3-oxazolidin-5-yl}methyl)-2-thiophenecarboxamide

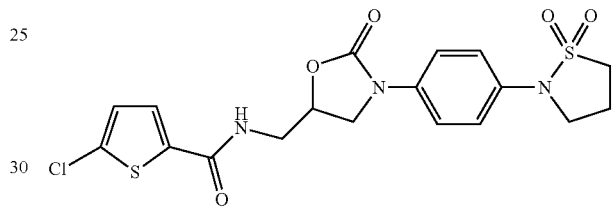

A mixture of 13.5 mg (0.027 mmol) of 5-chloro-N-{[3-(4-{[(3-chloropropyl)sulphonyl]amino}phenyl)-2-oxo-1,3-oxazolidin-5-yl]methyl}-2-thiophene-carboxamide (from Example 159) and 7.6 mg (0.055 mmol) of potassium carbonate in 0.2 ml of DMF is heated at 100° C. for 2 h. After cooling, the mixture is diluted with dichloromethane and washed with water. The organic phase is dried and concentrated. The residue is purified by preparative thin-layer chromatography (silica gel, dichloromethane/methanol, 95:5). Yield: 1.8 mg (14.4% of theory), MS (ESI): m/z (%)=456 (M+H, 15), 412 (100);
LC-MS (method 4): rt (%)=3.81 (90).
$IC_{50}$: 0.14 µM

Example 161

5-Chloro-N-[((5S)-3-{4-[(5-chloropentanoyl)amino]phenyl}-2-oxo-1,3-oxazolidin-5-yl)methyl]-2-thiophenecarboxamide

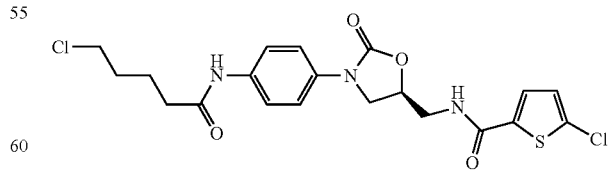

0.5 g (1.29 mmol) of N-{[(5S)-3-(4-aminophenyl)-2-oxo-1,3-oxazolidin-5-yl]methyl}-5-chloro-2-thiophenecarboxamide (from Example 149) is dissolved in 27 ml of tetrahydrofuran and admixed with 0.2 g (1.29 mmol) of 5-chlorovaleryl chloride and 0.395 ml (2.83 mmol) of triethylamine. The mixture is concentrated under reduced pressure and chromatographed over silica gel using a toluene/ethyl acetate=1:1→ethyl acetate gradient. This gives 315 mg (52% of theory) of a solid.

M.p.: 211° C.

Example 162

5-Chloro-N-({(5S)-2-oxo-3-[4-(2-oxo-1-piperidinyl)phenyl]-1,3-oxazolidin-5-yl}-methyl)-2-thiophenecarboxamide

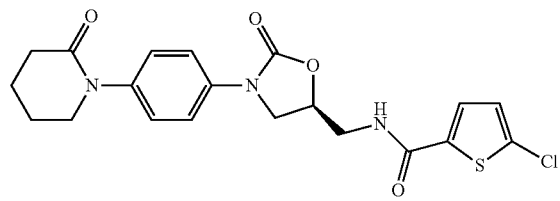 [SMILES: O=C(NC[C@H]1CN(c2ccc(N3CCCCC3=O)cc2)C(=O)O1)c1ccc(Cl)s1]

Under inert conditions, 5 ml of DMSO are admixed with 30 mg of NaH (60% in paraffin oil), and the mixture is heated at 75° C. for 30 min, until the evolution of gas has ceased. A solution of 290 mg (0.617 mmol) of 5-chloro-N-[((5S)-3-{4-[(5-chloropentanoyl)amino]phenyl}-2-oxo-1,3-oxazolidin-5-yl)methyl]-2-thiophenecarboxamide (from Example 161) in 5 ml of methylene chloride is then added dropwise, and the mixture is stirred at room temperature overnight. The reaction is terminated and the mixture is poured into 100 ml of water and extracted with ethyl acetate. The evaporated organic phase is chromatographed on an RP-8 column and the product is eluted with acetonitrile/water. This gives 20 mg (7.5% of theory) of the target compound.

M.p.: 205° C.;

NMR (300 MHz, $d_6$-DMSO): δ=1.85 (m, 4H), 2.35 (m, 2H), 3.58 (m, 4H), 3.85 (m, 1H), 4.2 (t, 1H), 4.82 (m, 1H), 7.18 (d, 1H, thiophene), 7.26 (d, 2H), 7.5 (d, 2H), 2.68 (d, 1H, thiophene), 9.0 (t, 1H, CONH).

$IC_{50}$: 2.8 nM

Example 163

5-Chloro-N-[((5S)-3-{4-[(3-bromopropionyl)amino]phenyl}-2-oxo-1,3-oxazolidin-5-yl)methyl]-2-thiophenecarboxamide

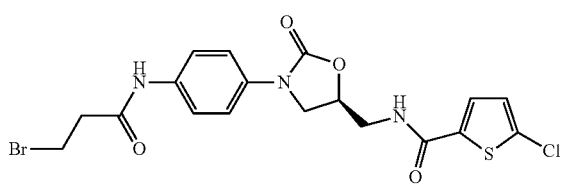 [SMILES: O=C(CCBr)Nc1ccc(N2C[C@H](CNC(=O)c3ccc(Cl)s3)OC2=O)cc1]

is obtained in an analogous manner from Example 149.

Example 164

5-Chloro-N-({(5S)-2-oxo-3-[4-(2-oxo-1-azetidinyl)phenyl]-1,3-oxazolidin-5-yl}-methyl)-2-thiophenecarboxamide

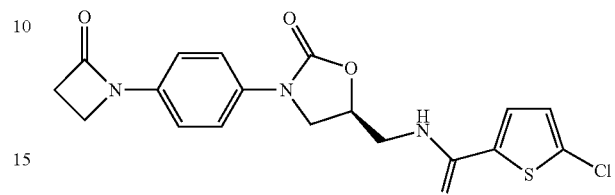

is obtained in an analogous manner by cyclization of the open-chain bromopropionyl compound from Example 163 using NaH/DMSO.

MS (ESI): m/z (%)=406 ([M+H]$^+$, 100), Cl pattern.

$IC_{50}$: 380 nM

Example 165 tert-Butyl 4-{4-[5-({[(5-chloro-2-thienyl)carbonyl]amino}methyl)-2-oxo-1,3-oxazolidin-3-yl]phenyl}-3,5-dioxo-1-piperazinecarboxylate

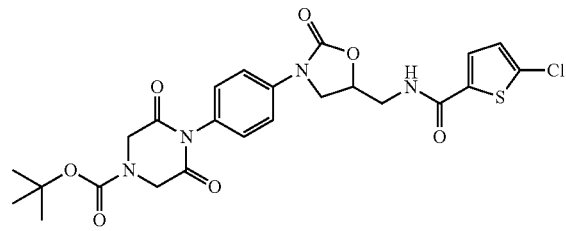 [SMILES: CC(C)(C)OC(=O)N1CC(=O)N(c2ccc(N3CC(CNC(=O)c4ccc(Cl)s4)OC3=O)cc2)C(=O)C1]

A solution of 199 mg (0.85 mmol) of Boc-iminodiacetic acid, 300 mg (2.2 mmol) of HOBT, 0.66 ml (6 mmol) of N-methylmorpholine and 647 mg (1.7 mmol) of HBTU is admixed with 300 mg (0.85 mmol) of N-{[3-(4-aminophenyl)-2-oxo-1,3-oxazolidin-5-yl]-methyl}-5-chloro-2-thiophene-carboxamide in 6 ml of a mixture of DMF and dichloromethane (1:1). The mixture is stirred overnight, diluted with dichloromethane and then washed with water, saturated ammonium chloride solution, saturated sodium bicarbonate solution, water and saturated sodium chloride solution. The organic phase is dried over magnesium sulphate and concentrated. The crude product is purified by silica gel chromatography (dichloromethane/methanol 98:2). Yield: 134 mg (29% of theory);

MS (ESI): m/z (%)=571 (M+Na, 82), 493 (100);

HPLC (method 3): rt (%)=4.39 (90).

$IC_{50}$: 2 μM

Example 166

N-[((5S)-3-{4-[(3R)-3-Amino-2-oxo-1-pyrrolidinyl]phenyl}-2-oxo-1,3-oxazolidin-5-yl)methyl]-5-chloro-2-thiophenecarboxamide trifluoroacetate

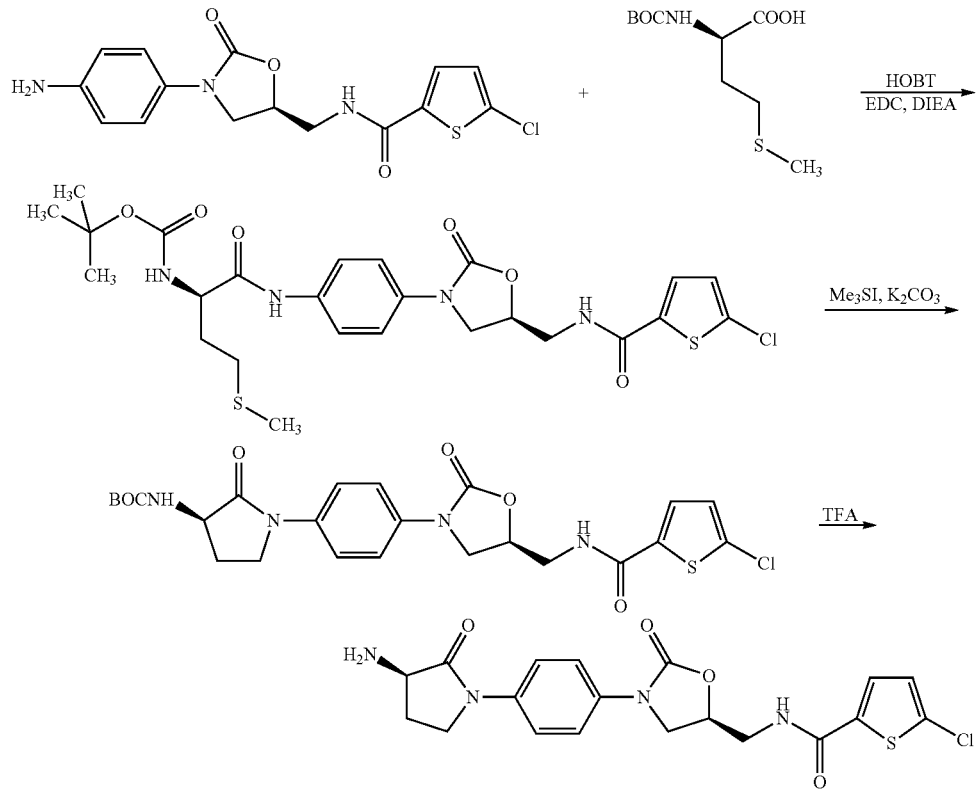

N2-(tert-Butoxycarbonyl)-N1-{4-[(5S)-5-({[(5-chloro-2-thienyl)carbonyl]amino}methyl)-2-oxo-1,3-oxazolidin-3-yl]phenyl}-D-methionineamide 429 mg (1.72 mmol) of N—BOC-D-methionine, 605 mg (1.72 mmol) of N-{[(5S)-3-(4-aminophenyl)-2-oxo-1,3-oxazolidin-5-yl]methyl}-5-chloro-2-thiophenecarboxamide, and 527 mg (3.44 mmol) of HOBT hydrate are dissolved in 35 ml of DMF and admixed with 660 mg (3.441 mmol) of EDCI hydrochloride and then dropwise with 689 mg (5.334 mmol) of N-ethyl-diisopropylamine. The mixture is stirred at room temperature for two days. The resulting suspension is filtered off with suction and the residue is washed with DMF. The combined filtrates are admixed with a little silica gel, concentrated under reduced pressure and chromatographed over silica gel using a toluene→T10EA7 gradient. This gives 170 mg (17% of theory) of the target compound of melting point 183° C.

$R_f$(SiO$_2$, toluene/ethyl acetate=1:1):0.2.

$^1$H-NMR (300 MHz, d$_6$-DMSO): δ=1.4 (s, 1H, BOC), 1.88-1.95 (m, 2H), 2.08 (s, 3H, SMe), 2.4-2.5 (m, 2H, partially obscurbed by DMSO), 3.6 (m, 2H), 3.8 (m, 1H), 4.15 (m, 2H), 4.8 (m, 1H), 7.2 (1H, thiophene), 7.42 (d, part of an AB system, 2H), 7.6 (d, part of an AB system, 2H), 7.7 (d, 1H, thiophene), 8.95 (t, 1H, CH$_2$NHCO), 9.93 (bs, 1H, NH).

tert-Butyl (3R)-1-{4-[(5S)-5-({[(5-chloro-2-thienyl)carbonyl]amino}methyl)-2-oxo-1,3-oxazolidin-3-yl]phenyl}-2-oxo-3-pyrrolidinylcarbamate 170 mg (0.292 mmol) of N2-(tert-butoxycarbonyl)-N1-{4-[(5S)-5-({[(5-chloro-2-thienyl)carbonyl]amino}methyl)-2-oxo-1,3-oxazolidin-3-yl]phenyl}-D-methionineamide are dissolved in 2 ml of DMSO and admixed with 178.5 mg (0.875 mmol) of trimethylsulphonium iodide and 60.4 mg (0.437 mmol) of potassium carbonate, and the mixture is stirred at 80° C. for 3.5 hours. The mixture is then concentrated under high vacuum and the residue is washed with ethanol. 99 mg of the target compound remain.

$^1$H-NMR (300 MHz, d$_6$-DMSO): δ=1.4 (s, 1H, BOC), 1.88-2.05 (m, 1H), 2.3-2.4 (m, 1H), 3.7-3.8 (m, 3H), 3.8-3.9 (m, 1H), 4.1-4.25 (m, 1H), 4.25-4.45 (m, 1H), 4.75-4.95 (m, 1H), 7.15 (1H, thiophene), 7.25 (d, 1H), 7.52 (d, part of an AB system, 2H), 7.65 (d, part of an AB system, 2H), 7.65 (d, 1H, thiophene), 9.0 (broad s, 1H).

N-[((5S)-3-{4-[(3R)-3-Amino-2-oxo-1-pyrrolidinyl]phenyl}-2-oxo-1,3-oxazolidin-5-yl)methyl]-5-chloro-2-thiophenecarboxamide trifluoroacetate 97 mg (0.181 mmol) of tert-butyl (3R)-1-{4-[(5S)-5-({[(5-chloro-2-thienyl)carbonyl]amino}methyl)-2-oxo-1,3-oxazolidin-3-yl]phenyl}-2-oxo-3-pyrrolidinylcarbamate are suspended in 4 ml of methylene chloride, 1.5 ml of trifluoroacetic acid are added and the mixture is stirred at room temperature for 1 hour. The mixture is then concentrated under reduced pressure and the residue is purified on an RP-HPLC (acetonitrile/water/0.1% TFA gradient). Evaporation of the appropriate fraction gives 29 mg (37% of theory) of the target compound of melting point 241° C. (decomp.).

$R_f$(SiO$_2$,EtOH/TEA=17:1) 0.19.

$^1$H-NMR (300 MHz, d$_6$-DMSO): δ=1.92-2.2 (m, 1H), 2.4-2.55 (m, 1H, partially obscured by DMSO peak), 3.55-3.65 (m, 2H), 3.75-3.95 (m, 3H), 4.1-4.3 (m, 2H), 4.75-4.9 (m, 1H), 7.2 (1H, thiophene), 7.58 (d, part of an AB system, 2H), 7.7 (d, part of an AB system, 2H), 7.68 (d, 1H, thiophene), 8.4 (broad s, 3H, NH3), 8.9 (t, 1H, NHCO).

The Examples 167 to 170 below refer to the introduction of sulphonamide groups in phenyl-substituted oxazolidinones:

General method for preparing substituted sulphonamides starting from 5-chloro-N-[(2-oxo-3-phenyl-1,3-oxazolidin-5-yl)methyl]-2-thiophenecarboxamide

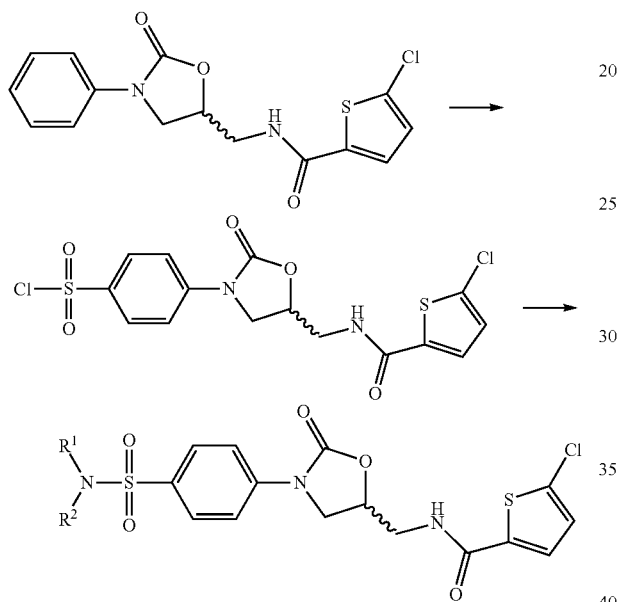

Under argon and at 5° C., 5-chloro-N-[(2-oxo-3-phenyl-1,3-oxazolidin-5-yl)methyl]-2-thiophenecarboxamide (from Example 96) is added to chlorosulphonic acid (12 eq.). The reaction mixture is stirred at room temperature for 2 h and then poured into ice-water. The resulting precipitate is filtered off, washed with water and dried.

Under argon and at room temperature, the precipitate is then dissolved in tetrahydrofuran (0.1 mol/l) and admixed with the appropriate amine (3 eq.), triethylamine (1.1 eq.) and dimethylaminopyridine (0.1 eq.). The reaction mixture is stirred for 1-2 h and then concentrated under reduced pressure. The desired product is purified by flash chromatography (dichloromethane/methanol mixtures).

The following compounds were prepared in an analogous manner:

Example 167

5-Chloro-N-({2-oxo-3-[4-(1-pyrrolidinylsulphonyl)phenyl]-1,3-oxazolidin-5-yl}-methyl)-2-thiophenecarboxamide MS (ESI): m/z (%)=492 ([M+Na]$^+$, 100), 470 ([M+H]$^+$, 68), Cl pattern;

HPLC (method 3): rt (%)=4.34 (100).

IC$_{50}$: 0.5 μM

Example 168

5-Chloro-N-[(3-{4-[(4-methyl-1-piperazinyl)sulphonyl]phenyl}-2-oxo-1,3-oxazolidin-5-yl)methyl]-2-thiophenecarboxamide MS (ESI): m/z (%)=499 ([M+H]$^+$, 100), Cl pattern;
HPLC (method 2): rt (%)=3.3 (100).

Example 169

5-Chloro-N-({2-oxo-3-[4-(1-piperidinylsulphonyl)phenyl]-1,3-oxazolidin-5-yl}-methyl)-2-thiophenecarboxamide MS (ESI): m/z (%)=484 ([M+H]$^+$, 100), Cl pattern;
HPLC (method 2): rt (%)=4.4 (100).

Example 170

5-Chloro-N-[(3-{4-[(4-hydroxy-1-piperidinyl)sulphonyl]phenyl}-2-oxo-1,3-oxazolidin-5-yl)methyl]-2-thiophenecarboxamide MS (ESI): m/z (%)=500 ([M+H]$^+$, 100), Cl pattern;
HPLC (method 3): rt (%)=3.9 (100).

Example 171

5-Chloro-N-({2-oxo-3-[4-(1-pyrrolidinyl)phenyl]-1,3-oxazolidin-5-yl}methyl)-2-thiophenecarboxamide

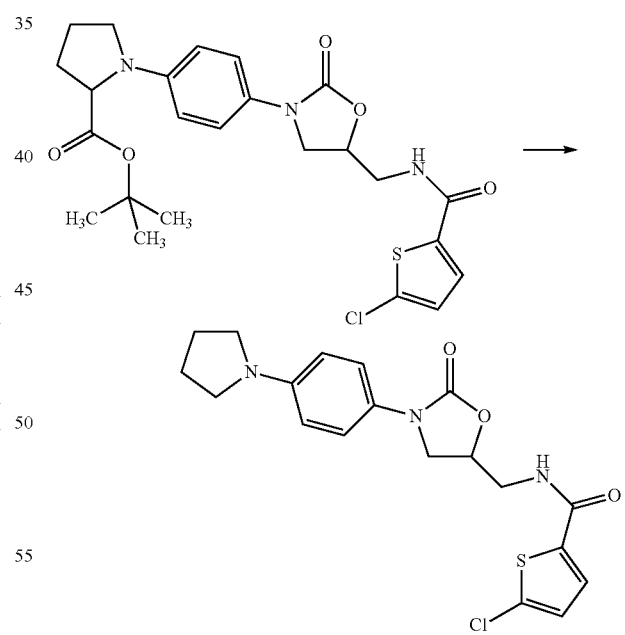

780 mg (1.54 mmol) of tert-butyl 1-{4-[5-({[(5-chloro-2-thienyl)carbonyl]amino}-methyl)-2-oxo-1,3-oxazolidin-3-yl]phenyl}prolinate are dissolved in 6 ml of dichloromethane and 9 ml of trifluoroacetic acid, and the mixture is stirred at 40° C. for two days. The reaction mixture is then concentrated and stirred with ether and 2N aqueous sodium hydroxide solution. The aqueous phase is concentrated and stirred with ether and 2N hydrochloric acid. The organic phase of this extraction is dried over MgSO$_4$, filtered and concentrated. The crude product is chromatographed over silica gel (CH$_2$Cl$_2$/EtOH/conc. aqu. NH$_3$ sol.=100/1/0.1 to 20/1/0.1).

This gives 280 mg (40% of theory) of the product.

MS (ESI): m/z (%)=406 (M+H, 100);

HPLC (method 4): rt=3.81 min.

HPLC Parameter and LC-MS Parameter for the HPLC and LC-MS Data Given in the Examples Above (the Unit of the Retention Time (rt) is Minutes):

[1] Column: Kromasil C18, L-R temperature: 30° C., flow rate=0.75 ml min$^1$, eluent: A=0.01 M HClO$_4$, B=CH$_3$CN, gradient: →0.5 min 98% A→4.5 min 10% A→6.5 min 10% A

[2] Column: Kromasil C18 60*2, L-R temperature: 30° C., flow rate=0.75 ml min$^1$, eluent: A=0.01 M H$_3$PO$_4$, B=CH$_3$CN, gradient: →0.5 min 90% A→4.5 min 10% A→6.5 min 10% A

[3] Column: Kromasil C18 60*2, L-R temperature: 30° C., flow rate=0.75 ml min$^{-1}$, eluent: A=0.005 M HClO$_4$, B=CH$_3$CN, gradient: →0.5 min 98% A→4.5 min 10% A→6.5 min 10% A

[4] Column: Symmetry C18 2.1×150 mm, column oven: 50° C., flow rate=0.6 ml min$^{-1}$, eluent: A=0.6 g 30% strength HCl/l of water, B=CH$_3$CN, gradient: 0.0 min 90% A→4.0 min 10% A→9 min 10% A

[5] MHZ-2Q, Instrument Micromass Quattro LCZ

Column Symmetry C18, 50 mm×2.1 mm, 3.5 μm, temperature: 40° C., flow rate=0.5 ml min$^{-1}$, eluent A=CH$_3$CN+0.1% formic acid, eluent B=water+0.1% formic acid, gradient: 0.0 min 10% A→4 min 90% A→6 min 90% A

[6] MHZ-2P, Instrument Micromass Platform LCZ

Column Symmetry C18, 50 mm×2.1 mm, 3.5 μm, temperature: 40° C., flow rate=0.5 ml min$^{-1}$, eluent A=CH$_3$CN+0.1% formic acid, eluent B=water+0.1% formic acid, gradient: 0.0 min 10% A→4 min 90% A→6 min 90% A

[7] MHZ-7Q, Instrument Micromass Quattro LCZ

Column Symmetry C18, 50 mm×2.1 mm, 3.5 μm, temperature: 40° C., flow rate=0.5 ml min$^{-1}$, eluent A=CH$_3$CN+0.1% formic acid, eluent B=water+0.1% formic acid, gradient: 0.0 min 5% A→1 min 5% A→5 min 90% A→6 min 90% A General Method for Preparing Oxazolidinones of the General Formula B by Solid-Phase-Supported Synthesis Reactions with different resin-bonded products were carried out in a set of separated reaction vessels.

5-(Bromomethyl)-3-(4-fluoro-3-nitrophenyl)-1,3-oxazolidin-2-one A (prepared from epibromohydrin and 4-fluoro-3-nitrophenyl isocyanate using LiBr/Bu$_3$PO in xylene analogously to U.S. Pat. No. 4,128,654, Ex. 2) (1.20 g, 3.75 mmol) and ethyldiisopropylamine (DIEA, 1.91 ml, 4.13 mmol) were dissolved in DMSO (70 ml), admixed with a secondary amine (1.1 eq., amine component 1) and reacted at 55° C. for 5 h. TentaGel SAM resin (5.00 g, 0.25 mmol/g) was added to this solution, and the mixture was reacted at 75° C. for 48 h. The resin was filtered, washed repeatedly with methanol (MeOH), dimethylformamide (DMF), MeOH, dichloromethane (DCM) and diethyl ether and dried. The resin (5.00 g) was suspended in dichloromethane (80 ml), admixed with DMA (10 eq.) and 5-chlorothiophene-2-carbonyl chloride [prepared by reacting 5-chlorothiophene-2-carboxylic acid (5 eq.) and 1-chloro-1-dimethylamino-2-methylpropene (5 eq.) in DCM (20 ml) at room temperature for 15 minutes] and the mixture was reacted at room temperature for 5 h. The resulting resin was filtered, washed repeatedly with MeOH, DCM and diethyl ether and dried. The resin was then suspended in DMF/water (v/v 9:2, 80 ml), admixed with SnCl$_2$*2H$_2$O (5 eq.) and reacted at room temperature for 18 h. The resin was washed repeatedly with MeOH, DMF, water, MeOH, DCM and diethyl ether and dried. This resin was suspended in DCM, admixed with DMA (10 eq.) and, at 0° C., with an acid chloride (5 eq. of acid derivative 1), and the mixture was reacted at room temperature overnight. Prior to the reaction, carboxylic acids were converted into the corresponding acid chlorides by reaction with 1-dimethylamino-1-chloro-2-methylpropene (1 eq., based on the carboxylic acid) in DCM at room temperature for 15 min. The resin was washed repeatedly with DMF, water, DMF, MeOH, DCM and diethyl ether and dried. If the acid derivative 1 used was an Fmoc-protected amino acid, the Fmoc protective group was removed in the last reaction step by reaction with piperidine/DMF (v/v, 1/4) at room temperature for 15 minutes, and the resin was washed with DMF, MeOH, DCM and diethyl ether and dried. The products were then removed from the solid phase using trifluoroacetic acid (TFA)/DCM (v/v, 1/1), the resin was filtered off and the reaction solutions were concentrated. The crude products were filtered over silica gel (DCM/MeOH, 9:1) and evaporated, giving a set of products B.

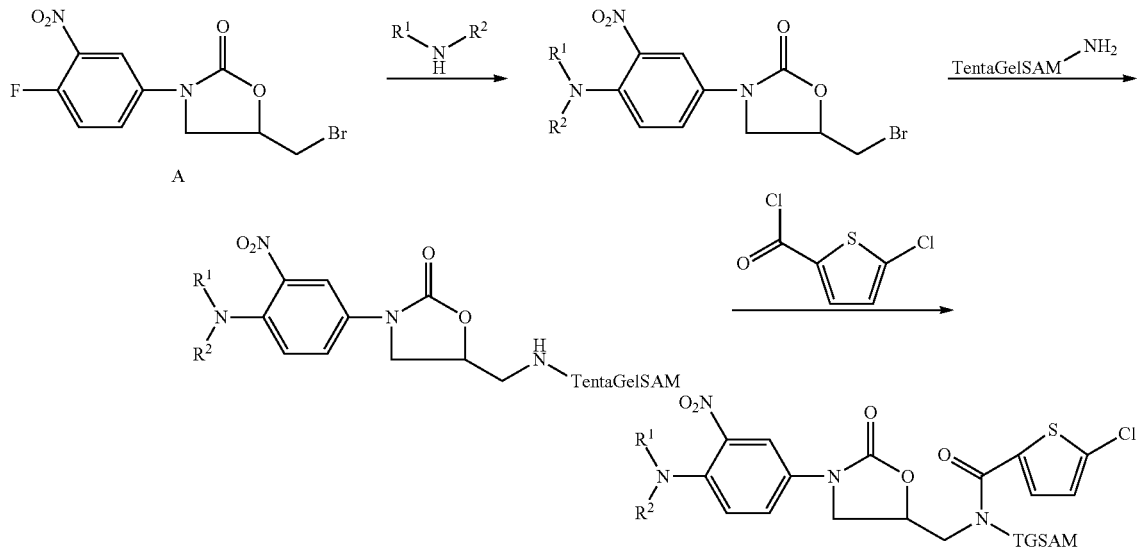

Compounds which were prepared by solid-phase-supported synthesis:

Example 172

N-({3-[3-Amino-4-(1-pyrrolidinyl)phenyl]-2-oxo-1,3-oxazolidin-5-yl}methyl)-5-chloro-2-thiophenecarboxamide

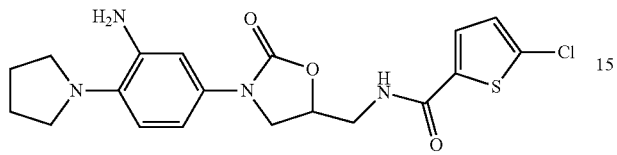

Analogously to the general procedure for preparing the derivatives B, 5 g (1.25 mmol) of TentaGel SAM resin were reacted with pyrrolidine as amine derivative 1. The aniline obtained after reduction with $SnCl_2 \cdot 2H_2O$ was, without any further acylation step, removed from the solid phase and concentrated. The crude product was partitioned between ethyl acetate and $NaHCO_3$ solution and the organic phase was salted out using NaCl, decanted and evaporated to dryness. This crude product was purified by vacuum flash chromatography over silica gel (dichloromethane/ethyl acetate, 3:1-1:2).

$^1$H-NMR (300 MHz, $CDCl_3$): 1.95-2.08, br, 4H, 3.15-3.30, br, 4H, 3.65-3.81, m, 2H, 3.89, ddd, 1H, 4.05, dd, 1H, 4.81, dddd, 1H, 6.46, dd, 1H, 6.72, dd, 1H, 6.90, dd, 1H, 6.99, dd, 1H, 7.03, dd, 1H, 7.29, d, 1H.

Example 173

N-[(3-{3-(B-Alanylamino)-4-[(3-hydroxypropyl)amino]phenyl}-2-oxo-1,3-oxazolidin-5-yl)methyl]-5-chloro-2-thiophenecarboxamide

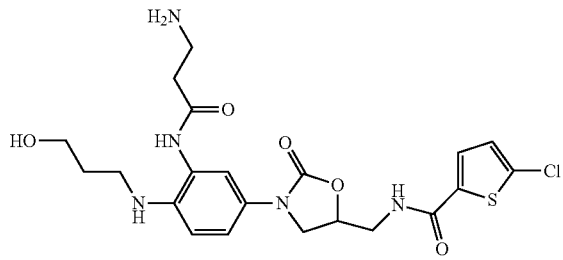 [SMILES: NCCC(=O)Nc1cc(N2CC(CNC(=O)c3ccc(Cl)s3)OC2=O)ccc1NCCCO]

Analogously to the general procedure for preparing the derivatives B, 5 g (1.25 mmol) of TentaGel SAM resin were reacted with azetidine as amine derivative 1 and Fmoc-β-alanine as acid derivative 1. The crude product obtained after the removal was stirred in methanol at room temperature for 48 h and evaporated to dryness. This crude product was purified by reversed phase HPLC using a water/TFA/acetonitrile gradient.

$^1$H-NMR (400 MHz, $CD_3OD$): 2.31, tt, 2H, 3.36, t, 2H, 3.54, t, 2H, 3.62, t, 2H; 3.72, dd, 1H, 3.79, dd, 1H, 4.01, dd, 1H, 4.29, dd, 2H, 4.43, t, 2H, 4.85-4.95, m, 1H, 7.01, d, 1H, 4.48-7.55, m, 2H, 7.61, d, 1H, 7.84, d, 1H.

Example 174

N-({3-[4-(3-Amino-1-pyrrolidinyl)-3-nitrophenyl]-2-oxo-1,3-oxazolidin-5-yl}-methyl)-5-chloro-2-thiophenecarboxamide

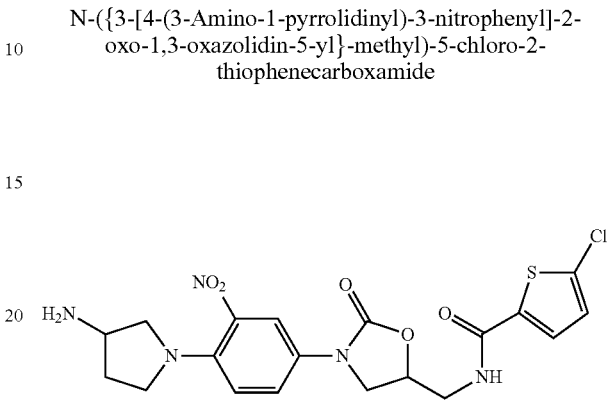

Analogously to the general procedure for preparing the derivatives B, 130 mg (32.5 mop of TentaGel SAM resin were reacted with tert-butyl 3-pyrrolidinylcarbamate as amine derivative 1. The nitrobenzene derivative obtained after the acylation with 5-chlorothiophenecarboxylic acid was removed from the solid phase and concentrated. This crude product was purified by reversed phase HPLC using a water/TFA/acetonitrile gradient.

$^1$H-NMR (400 MHz, $CD_3OH$): 2.07-2.17, m, 1H, 2.39-2.49, m, 1H, 3.21-3.40, m, 2 H, 3.45, dd, 1H, 3.50-3.60, m, 1H, 3.67, dd, 1H, 3.76, dd, 1H, 3.88-4.00, m, 2H; 4.14-4.21, t, 1H, 4.85-4.95, m, 1H, 7.01, d, 1H, 7.11, d, 1H, 7.52, d, 1H, 7.66, dd, 1H, 7.93, d, 1H.

Example 175

N-({3-[3-Amino-4-(1-piperidinyl)phenyl]-2-oxo-1,3-oxazolidin-5-yl}methyl)-5-chloro-2-thiophenecarboxamide

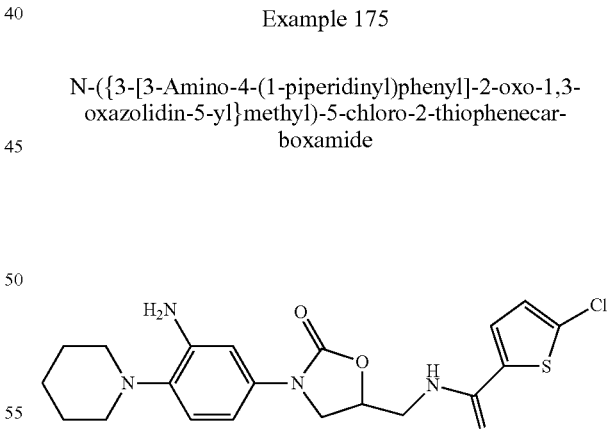

Analogously to the general procedure for preparing the derivatives B, 130 mg (32.5 mop of TentaGel SAM resin were reacted with piperidine as amine derivative 1. The aniline obtained after the reduction was, without any further acylation step, removed from the solid phase and concentrated. This crude product was purified by reversed phase HPLC using a water/TFA/acetonitrile gradient.

$^1$H-NMR (400 MHz, $CD_3OH$): 1.65-1.75, m, 2H, 1.84-1.95, m, 4H, 3.20-3.28, m, 4H, 3.68, dd, 1H, 3.73, dd, 1H, 3.90, dd, 1H, 4.17, dd, 1H, 4.80-4.90, m, 1H, 7.00, d, 1H, 7.05, dd, 1H, 7.30-7.38, m, 2H, 7.50, d, 1H.

Example 176

N-({3-[3-(Acetylamino)-4-(1-pyrrolidinyl)phenyl]-2-oxo-1,3-oxazolidin-5-yl}-methyl)-5-chloro-2-thiophenecarboxamide

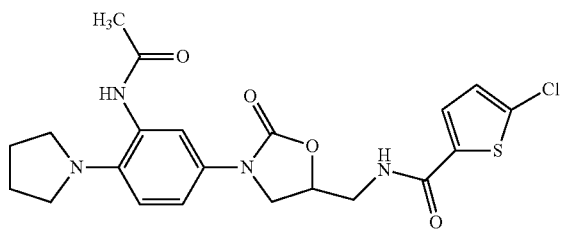 [SMILES: CC(=O)Nc1cc(N2CC(CNC(=O)c3ccc(Cl)s3)OC2=O)ccc1N1CCCC1]

Analogously to the general procedure for preparing the derivatives B, 130 mg (32.5 mop of TentaGel SAM resin were reacted pyrrolidine as amine derivative 1 and acetyl chloride as acid derivative 1. The crude product was partitioned between ethyl acetate NaHCO$_3$ solution and the organic phase was salted out using NaCl, decanted and evaporated to dryness. This crude product was purified by vacuum flash chromatography over silica gel (dichloromethane/ethyl acetate, 1:1-0:1).

$^1$H-NMR (400 MHz, CD$_3$OH): 1.93-2.03, br, 4H, 2.16, s, 3H, 3.20-3.30, br, 4H, 3.70, d, 2H, 3.86, dd, 1H, 4.10, dd, 1H, 4.14, dd, 1H, 4.80-4.90, in, 1H, 7.00, d, 1H, 7.07, d, 1H, 7.31, dd, 1H, 7.51, d, 1H, 7.60, d, 1H.

The following compounds were prepared analogously to the general procedure.

| Example | Structure | Ret. time | HPLC [%] |
|---|---|---|---|
| 177 | 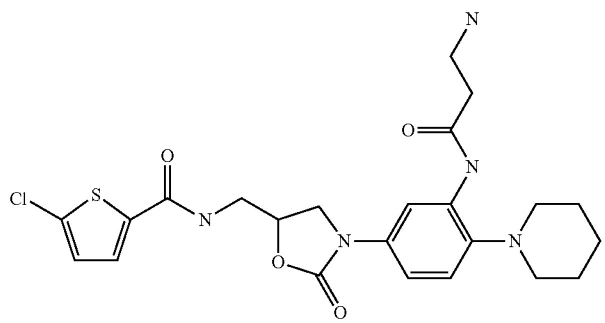 [SMILES: NCCC(=O)Nc1cc(N2CC(CNC(=O)c3ccc(Cl)s3)OC2=O)ccc1N1CCCCC1] | 2.62 | 79.7 |
| 178 | 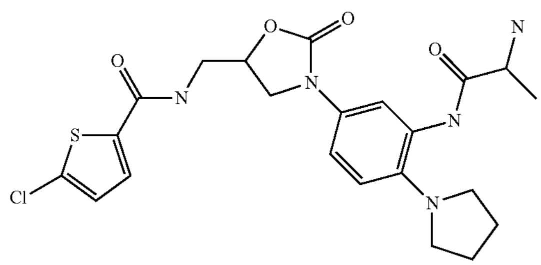 [SMILES: CC(N)C(=O)Nc1cc(N2CC(CNC(=O)c3ccc(Cl)s3)OC2=O)ccc1N1CCCC1] | 2.49 | 33.7 |
| 179 | 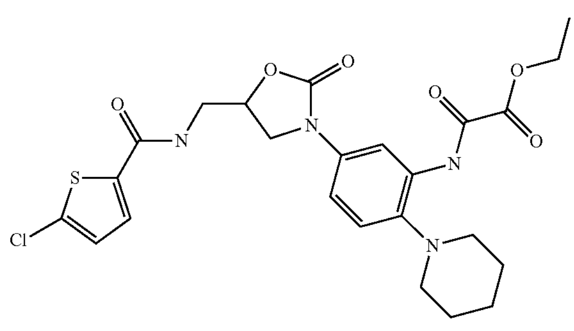 [SMILES: CCOC(=O)C(=O)Nc1cc(N2CC(CNC(=O)c3ccc(Cl)s3)OC2=O)ccc1N1CCCCC1] | 4.63 | 46.7 |

-continued
| Example | Structure | Ret. time | HPLC [%] |
|---|---|---|---|
| 180 | 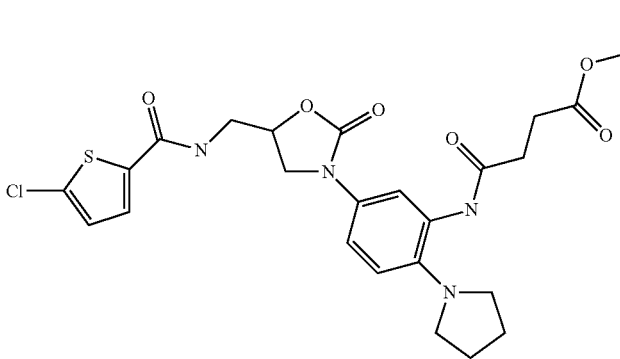 | 3.37 | 44.8 |
| 181 | 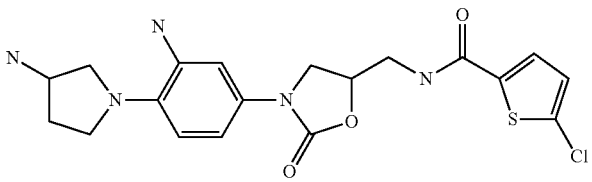 [SMILES: Nc1cc(N2CC(CNC(=O)c3ccc(Cl)s3)OC2=O)ccc1N1CCC(N)C1] | 2.16 | 83 |
| 182 | 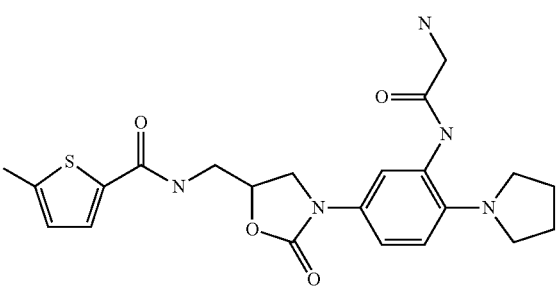 | 2.31 | 93.3 |
| 183 | 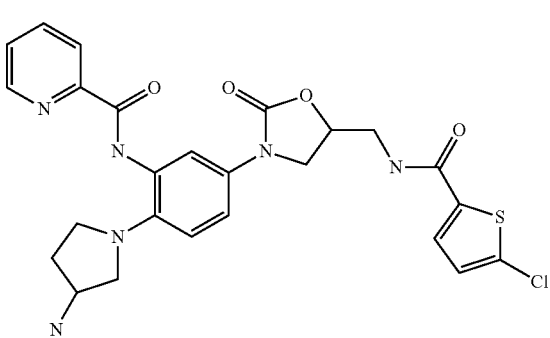 [SMILES: NC1CCN(c2ccc(N3CC(CNC(=O)c4ccc(Cl)s4)OC3=O)cc2NC(=O)c2ccccn2)C1] | 2.7 | 100 |
| 184 | 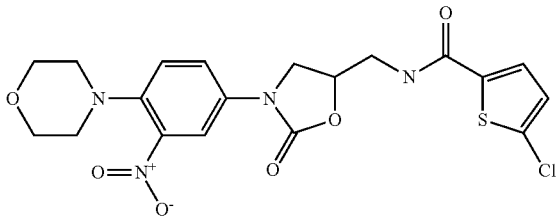 [SMILES: O=C(NCC1CN(c2ccc(N3CCOCC3)c([N+](=O)[O-])c2)C(=O)O1)c1ccc(Cl)s1] | 3.91 | 51 |

| Example | Structure | Ret. time | HPLC [%] |
|---|---|---|---|
| 185 | 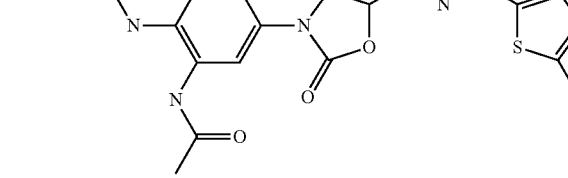 | 2.72 | 75.2 |
| 186 | 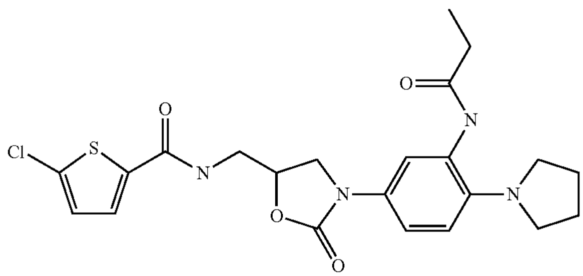 [SMILES: CCC(=O)Nc1cc(N2CC(CNC(=O)c3ccc(Cl)s3)OC2=O)ccc1N1CCCC1] | 3.17 | 46 |
| 187 | 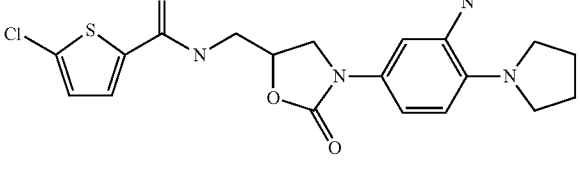 | 4.61 | 50.2 |
| 188 | 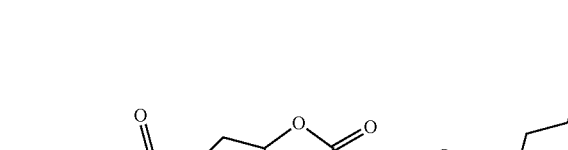 | 3.89 | 56.6 |
| 189 | 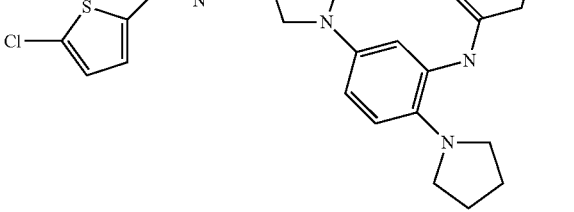 | 3.37 | 52.9 |

-continued

| Example | Structure | Ret. time | HPLC [%] |
|---|---|---|---|
| 190 | 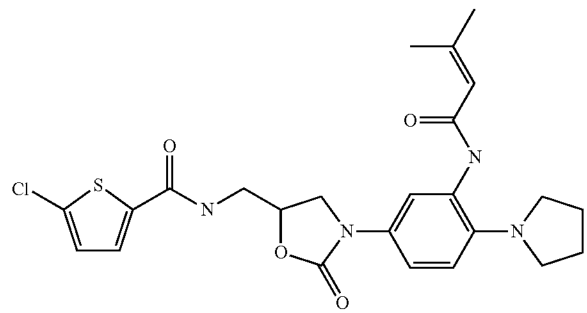 [SMILES: CC(C)=CC(=O)Nc1cc(N2CC(CNC(=O)c3ccc(Cl)s3)OC2=O)ccc1N1CCCC1] | 3.6 | 63.9 |
| 191 | 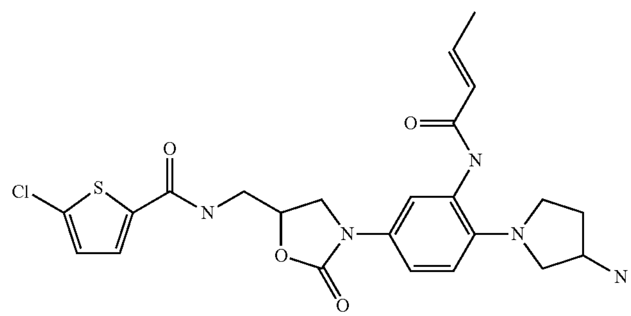 [SMILES: C/C=C/C(=O)Nc1cc(N2CC(CNC(=O)c3ccc(Cl)s3)OC2=O)ccc1N1CCC(N)C1] | 2.52 | 70.1 |
| 192 | 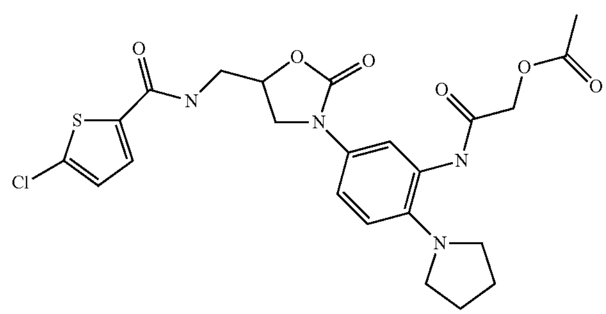 [SMILES: CC(=O)OCC(=O)Nc1cc(N2CC(CNC(=O)c3ccc(Cl)s3)OC2=O)ccc1N1CCCC1] | 3.52 | 46.6 |
| 193 | 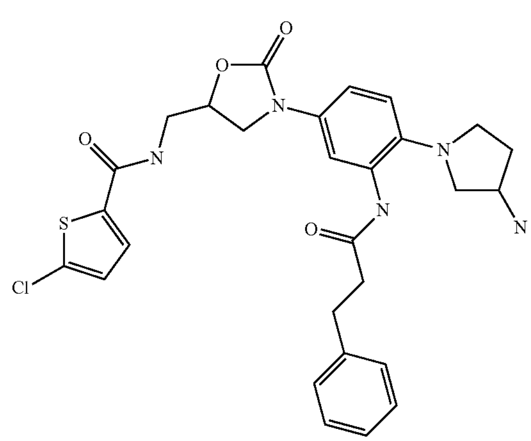 [SMILES: NC1CCN(c2ccc(N3CC(CNC(=O)c4ccc(Cl)s4)OC3=O)cc2NC(=O)CCc2ccccc2)C1] | 2.87 | 50.1 |

-continued

| Example | Structure | Ret. time | HPLC [%] |
|---------|-----------|-----------|----------|
| 194 | 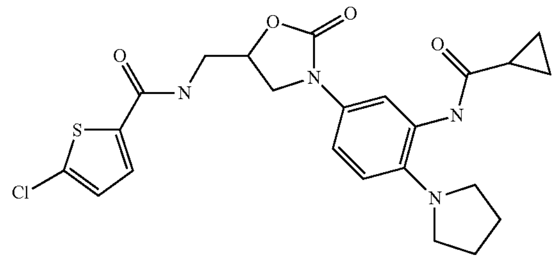 [SMILES: O=C(NCC1CN(c2ccc(N3CCCC3)c(NC(=O)C3CC3)c2)C(=O)O1)c1ccc(Cl)s1] | 3.25 | 71.1 |
| 195 | 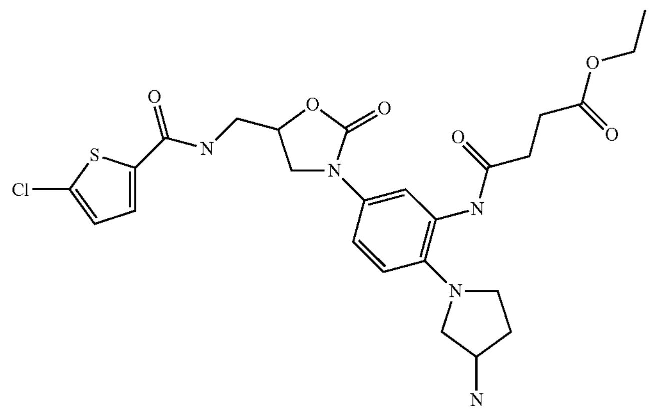 [SMILES: CCOC(=O)CCC(=O)Nc1cc(N2CC(CNC(=O)c3ccc(Cl)s3)OC2=O)ccc1N1CCC(N)C1] | 2.66 | 67 |
| 196 | 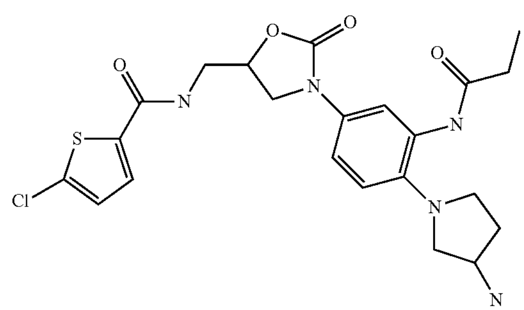 [SMILES: CCC(=O)Nc1cc(N2CC(CNC(=O)c3ccc(Cl)s3)OC2=O)ccc1N1CCC(N)C1] | 2.4 | 52.1 |
| 197 | 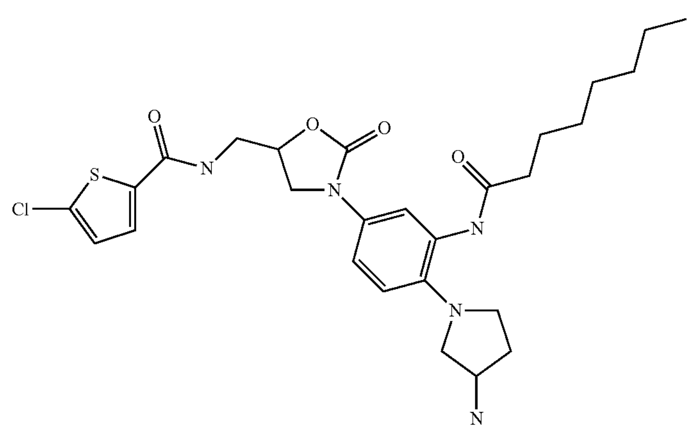 [SMILES: CCCCCCCC(=O)Nc1cc(N2CC(CNC(=O)c3ccc(Cl)s3)OC2=O)ccc1N1CCC(N)C1] | 3.13 | 48.9 |

-continued

| Example | Structure | Ret. time | HPLC [%] |
|---|---|---|---|
| 198 | 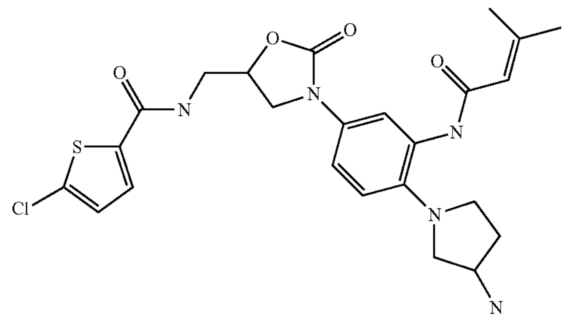 [SMILES: CC(C)=CC(=O)Nc1cc(N2CC(CNC(=O)c3ccc(Cl)s3)OC2=O)ccc1N1CCC(N)C1] | 2.67 | 75.5 |
| 199 | 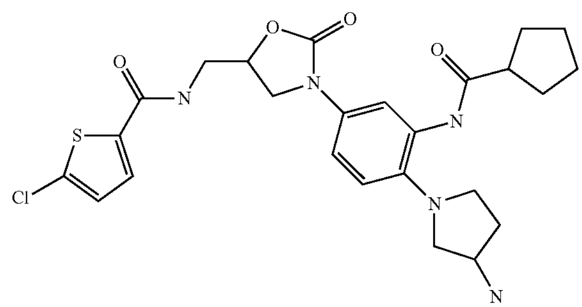 [SMILES: NC1CCN(c2ccc(N3CC(CNC(=O)c4ccc(Cl)s4)OC3=O)cc2NC(=O)C2CCCC2)C1] | 2.72 | 65.7 |
| 200 | 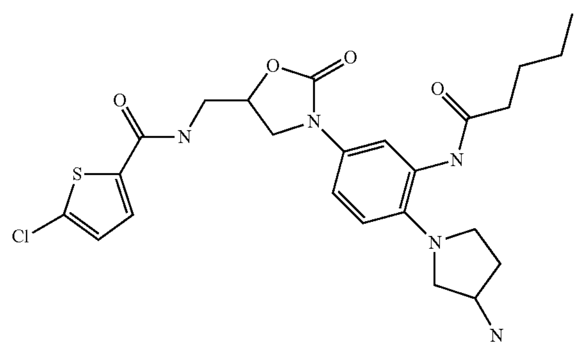 [SMILES: CCCCC(=O)Nc1cc(N2CC(CNC(=O)c3ccc(Cl)s3)OC2=O)ccc1N1CCC(N)C1] | 2.71 | 57.3 |
| 201 | 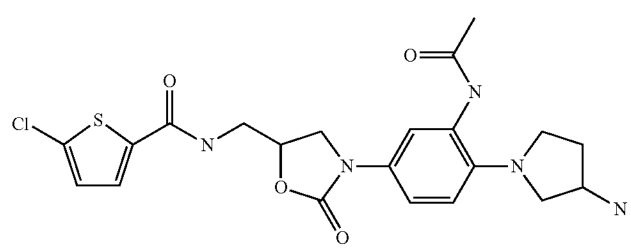 [SMILES: CC(=O)Nc1cc(N2CC(CNC(=O)c3ccc(Cl)s3)OC2=O)ccc1N1CCC(N)C1] | 2.22 | 100 |
| 202 | 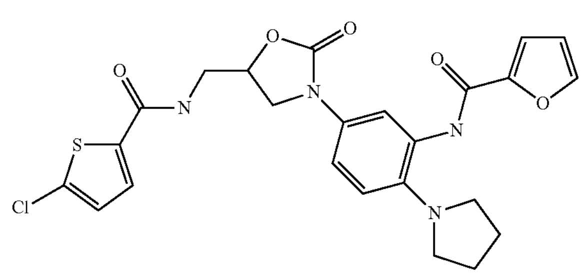 [SMILES: O=C(Nc1cc(N2CC(CNC(=O)c3ccc(Cl)s3)OC2=O)ccc1N1CCCC1)c1ccco1] | 3.89 | 75.7 |

-continued

| Example | Structure | Ret. time | HPLC [%] |
|---|---|---|---|
| 203 | 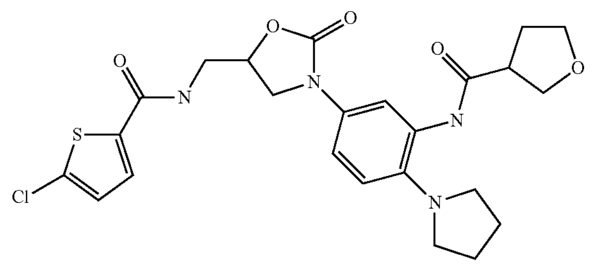 [SMILES: O=C(NCC1CN(c2ccc(N3CCCC3)c(NC(=O)C3CCOC3)c2)C(=O)O1)c1ccc(Cl)s1] | 3.19 | 49.6 |
| 204 | 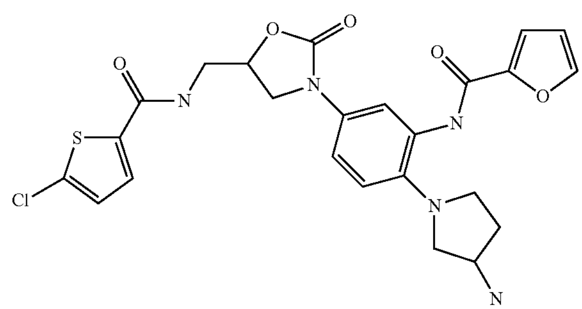 [SMILES: NC1CCN(c2ccc(N3CC(CNC(=O)c4ccc(Cl)s4)OC3=O)cc2NC(=O)c2ccco2)C1] | 2.55 | 88.2 |
| 205 | 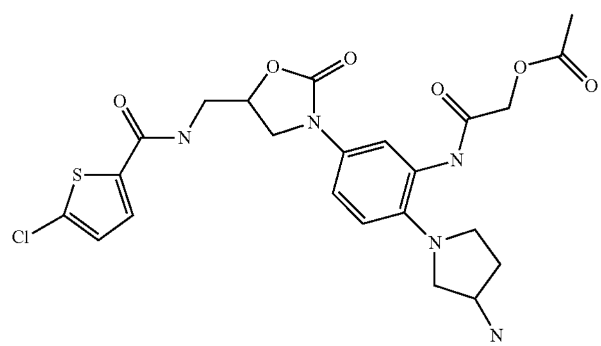 [SMILES: CC(=O)OCC(=O)Nc1cc(N2CC(CNC(=O)c3ccc(Cl)s3)OC2=O)ccc1N1CCC(N)C1] | 2.44 | 68.6 |
| 206 | 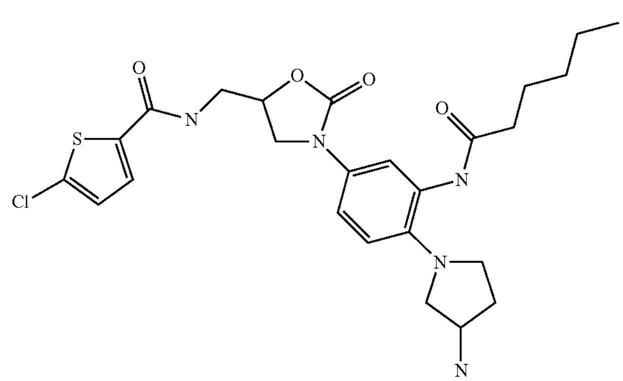 [SMILES: CCCCCC(=O)Nc1cc(N2CC(CNC(=O)c3ccc(Cl)s3)OC2=O)ccc1N1CCC(N)C1] | 2.86 | 71.8 |

-continued

| Example | Structure | Ret. time | HPLC [%] |
|---|---|---|---|
| 207 | 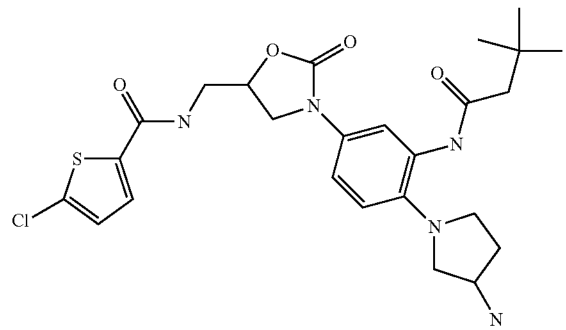 [SMILES: CC(C)(C)CC(=O)Nc1cc(N2CC(CNC(=O)c3ccc(Cl)s3)OC2=O)ccc1N1CCC(N)C1] | 2.8 | 63.6 |
| 208 | 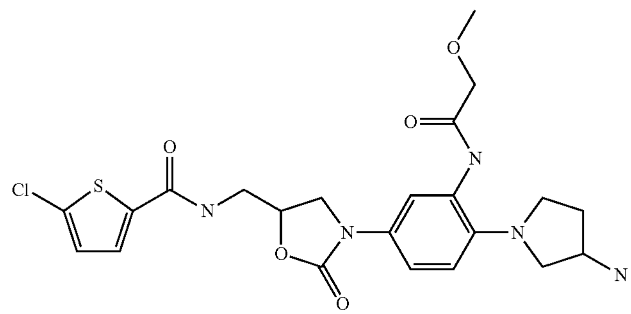 [SMILES: COCC(=O)Nc1cc(N2CC(CNC(=O)c3ccc(Cl)s3)OC2=O)ccc1N1CCC(N)C1] | 2.41 | 77 |
| 209 | 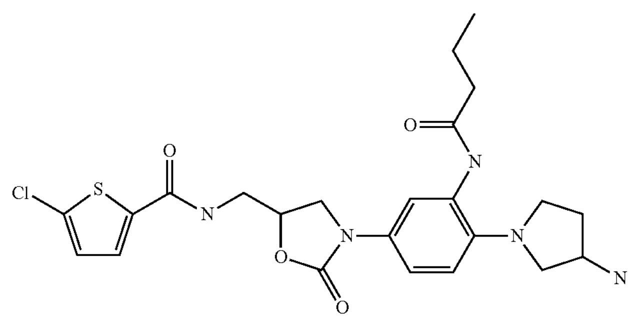 | 2.56 | 67.9 |
| 210 | 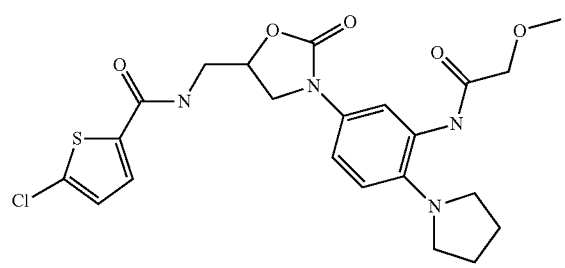 [SMILES: COCC(=O)Nc1cc(N2CC(CNC(=O)c3ccc(Cl)s3)OC2=O)ccc1N1CCCC1] | 3.67 | 78.4 |
| 211 | 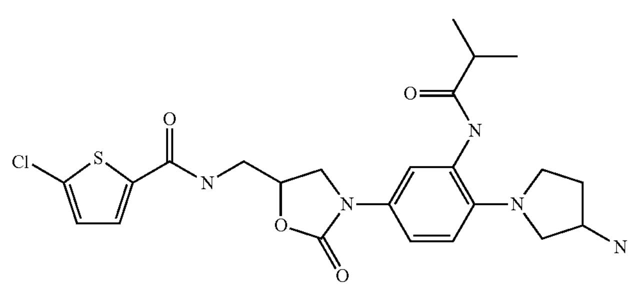 [SMILES: CC(C)C(=O)Nc1cc(N2CC(CNC(=O)c3ccc(Cl)s3)OC2=O)ccc1N1CCC(N)C1] | 2.54 | 69.8 |

-continued
| Example | Structure | Ret. time | HPLC [%] |
|---|---|---|---|
| 212 | 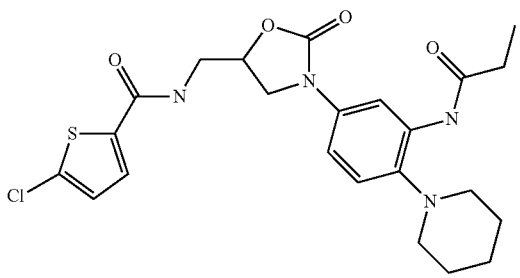 [SMILES: CCC(=O)Nc1cc(N2CC(CNC(=O)c3ccc(Cl)s3)OC2=O)ccc1N1CCCCC1] | 3.84 | 59.2 |
| 213 | 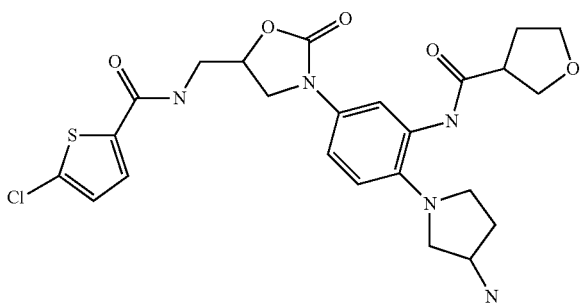 [SMILES: NC1CCN(c2ccc(N3CC(CNC(=O)c4ccc(Cl)s4)OC3=O)cc2NC(=O)C2CCOC2)C1] | 2.41 | 67.8 |
| 214 | 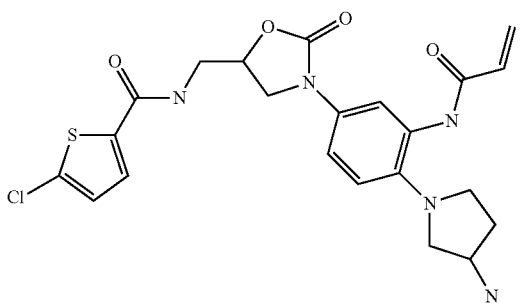 [SMILES: C=CC(=O)Nc1cc(N2CC(CNC(=O)c3ccc(Cl)s3)OC2=O)ccc1N1CCC(N)C1] | 2.41 | 75.4 |
| 215 | 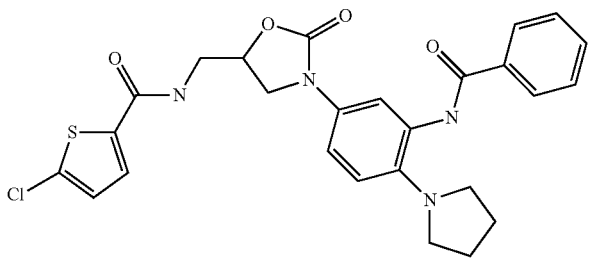 [SMILES: O=C(Nc1cc(N2CC(CNC(=O)c3ccc(Cl)s3)OC2=O)ccc1N1CCCC1)c1ccccc1] | 4.01 | 81.3 |
| 216 | 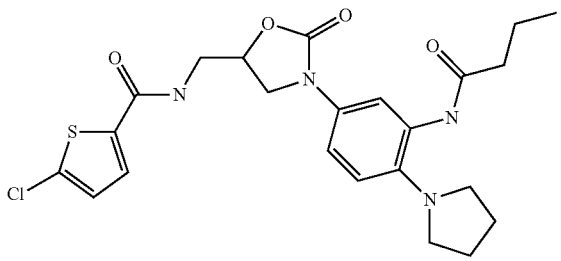 | 3.46 | 49.5 |

| Example | Structure | Ret. time | HPLC [%] |
|---|---|---|---|
| 217 | 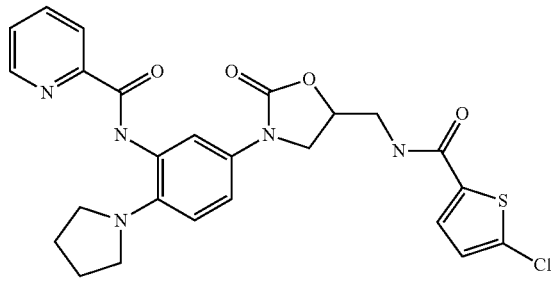 [SMILES: O=C(Nc1cc(N2CC(CNC(=O)c3ccc(Cl)s3)OC2=O)ccc1N1CCCC1)c1ccccn1] | 4.4 | 60.2 |
| 218 | 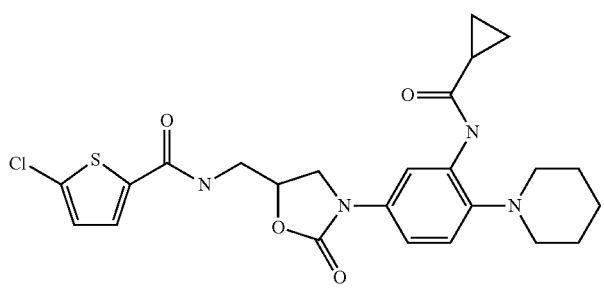 [SMILES: O=C(NCC1CN(c2ccc(N3CCCCC3)c(NC(=O)C3CC3)c2)C(=O)O1)c1ccc(Cl)s1] | 3.79 | 70.9 |
| 219 | 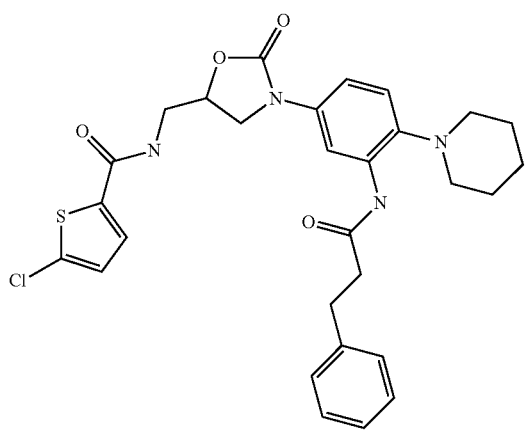 [SMILES: O=C(CCc1ccccc1)Nc1cc(N2CC(CNC(=O)c3ccc(Cl)s3)OC2=O)ccc1N1CCCCC1] | 4.57 | 51.5 |
| 220 | 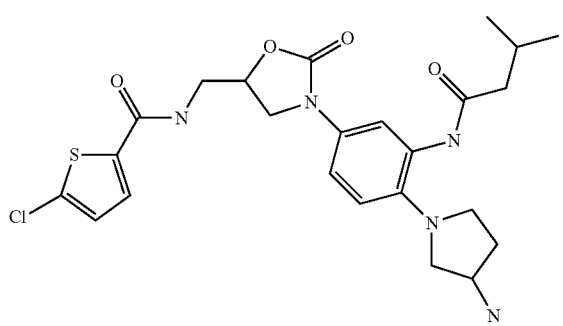 [SMILES: CC(C)CC(=O)Nc1cc(N2CC(CNC(=O)c3ccc(Cl)s3)OC2=O)ccc1N1CCC(N)C1] | 2.68 | 100 |

-continued

| Example | Structure | Ret. time | HPLC [%] |
|---|---|---|---|
| 221 | 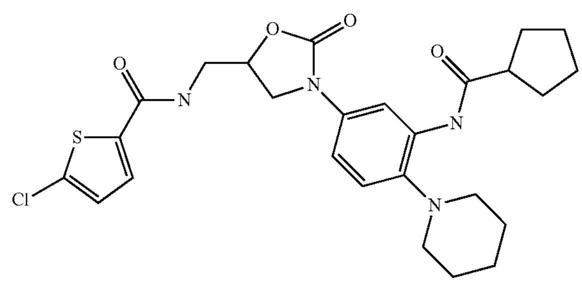 [SMILES: O=C(NCC1CN(c2ccc(N3CCCCC3)c(NC(=O)C3CCCC3)c2)C(=O)O1)c1ccc(Cl)s1] | 4.53 | 63.5 |
| 222 | 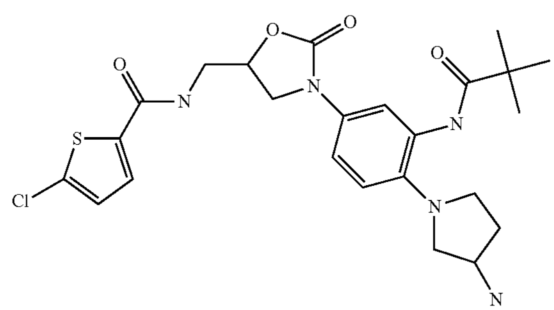 [SMILES: CC(C)(C)C(=O)Nc1cc(N2CC(CNC(=O)c3ccc(Cl)s3)OC2=O)ccc1N1CCC(N)C1] | 2.66 | 89.2 |
| 223 | 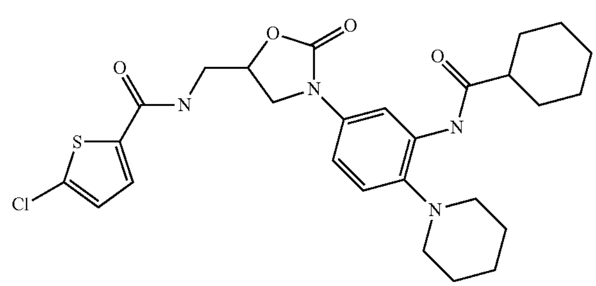 [SMILES: O=C(NCC1CN(c2ccc(N3CCCCC3)c(NC(=O)C3CCCCC3)c2)C(=O)O1)c1ccc(Cl)s1] | 4.76 | 69.3 |
| 224 | 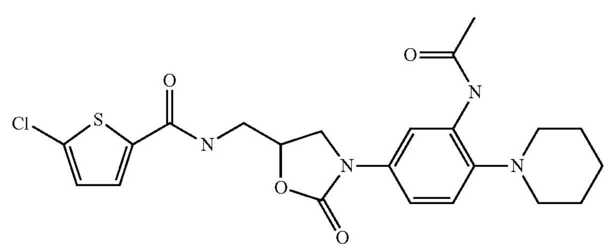 [SMILES: CC(=O)Nc1cc(N2CC(CNC(=O)c3ccc(Cl)s3)OC2=O)ccc1N1CCCCC1] | 3.45 | 77.4 |
| 225 | 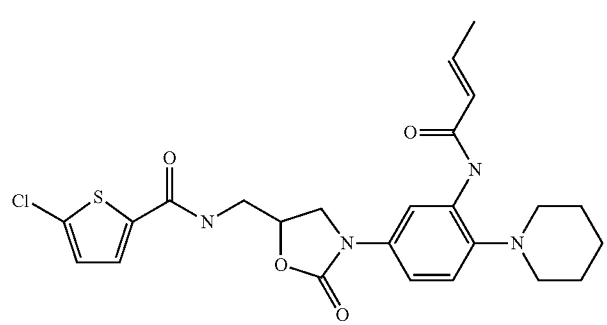 [SMILES: C/C=C/C(=O)Nc1cc(N2CC(CNC(=O)c3ccc(Cl)s3)OC2=O)ccc1N1CCCCC1] | 3.97 | 63.2 |

| Example | Structure | Ret. time | HPLC [%] |
|---|---|---|---|
| 226 | 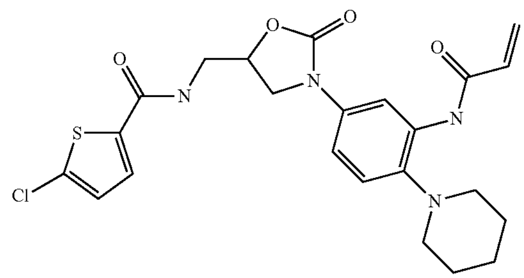 [SMILES: C=CC(=O)Nc1cc(N2CC(CNC(=O)c3ccc(Cl)s3)OC2=O)ccc1N1CCCCC1] | 3.94 | 61.4 |
| 227 | 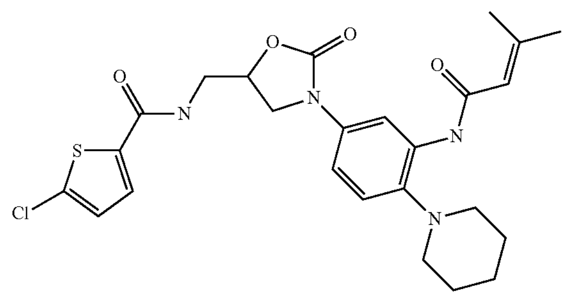 [SMILES: CC(C)=CC(=O)Nc1cc(N2CC(CNC(=O)c3ccc(Cl)s3)OC2=O)ccc1N1CCCCC1] | 4.15 | 66.3 |
| 228 | 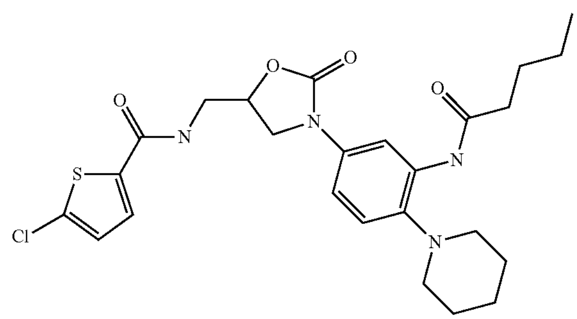 [SMILES: CCCCC(=O)Nc1cc(N2CC(CNC(=O)c3ccc(Cl)s3)OC2=O)ccc1N1CCCCC1] | 4.41 | 55.1 |
| 229 | 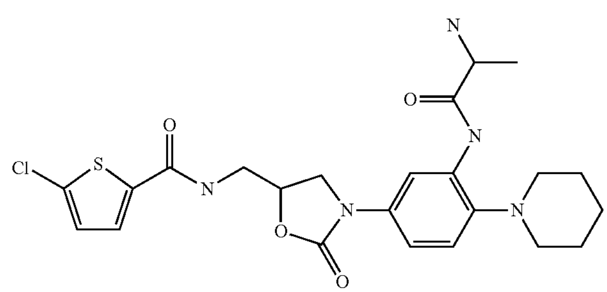 [SMILES: CC(N)C(=O)Nc1cc(N2CC(CNC(=O)c3ccc(Cl)s3)OC2=O)ccc1N1CCCCC1] | 2.83 | 41.1 |
| 230 | 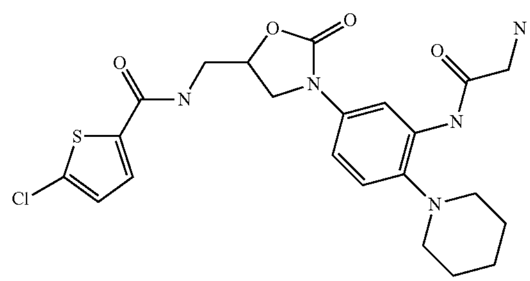 [SMILES: NCC(=O)Nc1cc(N2CC(CNC(=O)c3ccc(Cl)s3)OC2=O)ccc1N1CCCCC1] | 2.7 | 83 |

-continued

| Example | Structure | Ret. time | HPLC [%] |
|---|---|---|---|
| 231 | 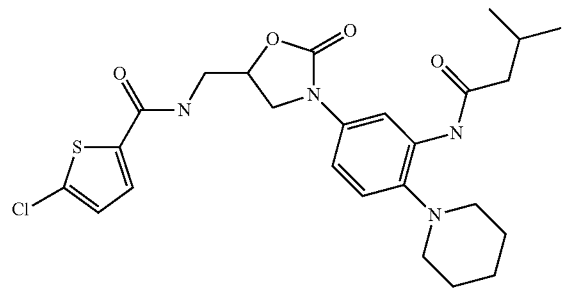 [SMILES: CC(C)CC(=O)Nc1cc(N2CC(CNC(=O)c3ccc(Cl)s3)OC2=O)ccc1N1CCCCC1] | 4.39 | 64.2 |
| 232 | 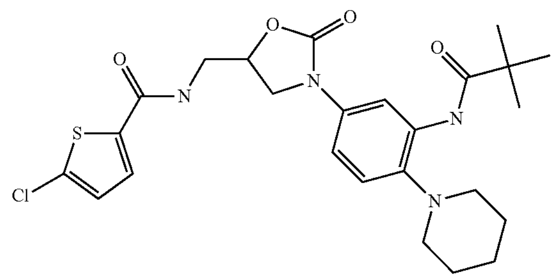 [SMILES: CC(C)(C)C(=O)Nc1cc(N2CC(CNC(=O)c3ccc(Cl)s3)OC2=O)ccc1N1CCCCC1] | 4.85 | 74.9 |
| 233 | 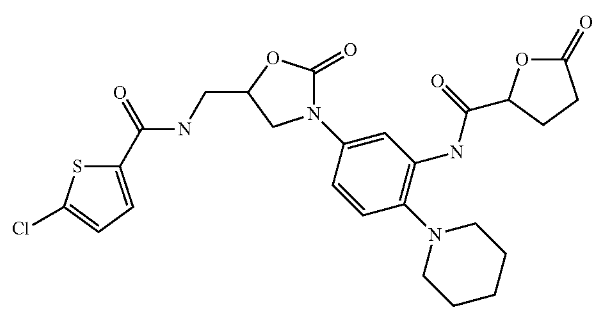 [SMILES: O=C1CCC(C(=O)Nc2cc(N3CC(CNC(=O)c4ccc(Cl)s4)OC3=O)ccc2N2CCCCC2)O1] | 4.17 | 41 |
| 234 | 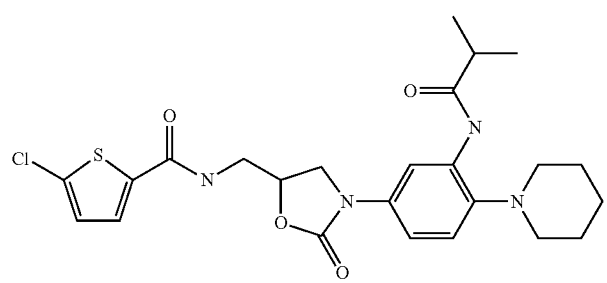 [SMILES: CC(C)C(=O)Nc1cc(N2CC(CNC(=O)c3ccc(Cl)s3)OC2=O)ccc1N1CCCCC1] | 4.21 | 61.8 |
| 235 | 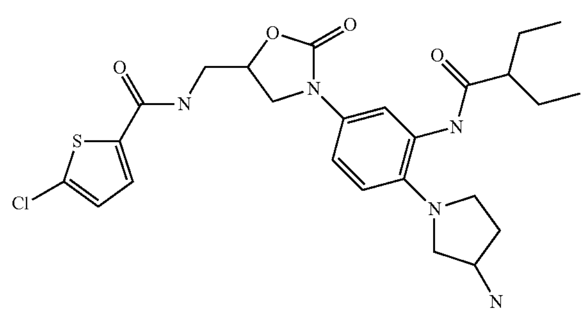 [SMILES: CCC(CC)C(=O)Nc1cc(N2CC(CNC(=O)c3ccc(Cl)s3)OC2=O)ccc1N1CCC(N)C1] | 2.75 | 100 |

-continued

| Example | Structure | Ret. time | HPLC [%] |
|---|---|---|---|
| 236 | 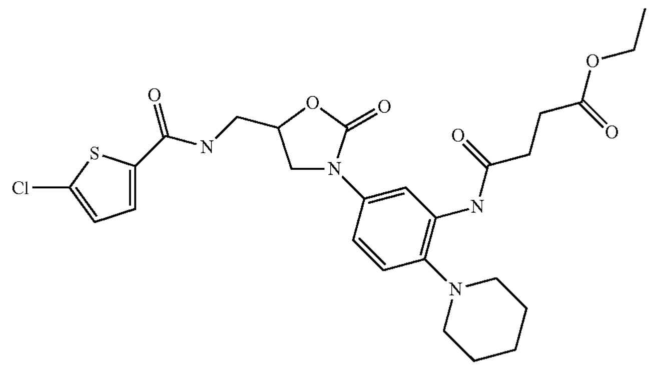 [SMILES: CCOC(=O)CCC(=O)Nc1cc(N2CC(CNC(=O)c3ccc(Cl)s3)OC2=O)ccc1N1CCCCC1] | 3.94 | 50 |
| 237 | 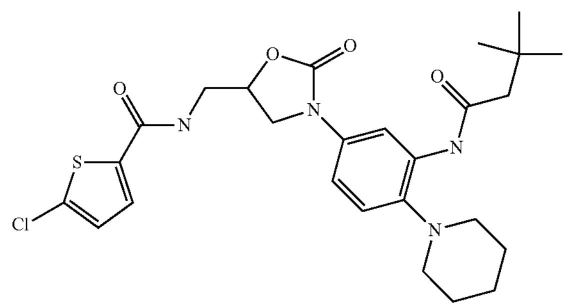 [SMILES: CC(C)(C)CC(=O)Nc1cc(N2CC(CNC(=O)c3ccc(Cl)s3)OC2=O)ccc1N1CCCCC1] | 4.65 | 75.8 |
| 238 | 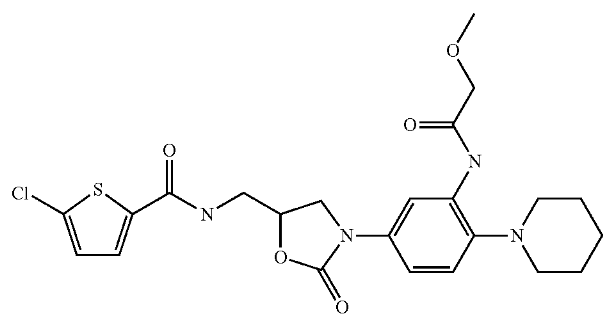 [SMILES: COCC(=O)Nc1cc(N2CC(CNC(=O)c3ccc(Cl)s3)OC2=O)ccc1N1CCCCC1] | 4.4 | 75.3 |
| 239 | 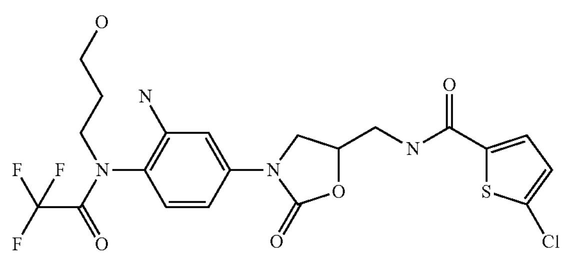 [SMILES: Nc1cc(N2CC(CNC(=O)c3ccc(Cl)s3)OC2=O)ccc1N(CCCO)C(=O)C(F)(F)F] | 4.24 | 62.2 |
| 240 | 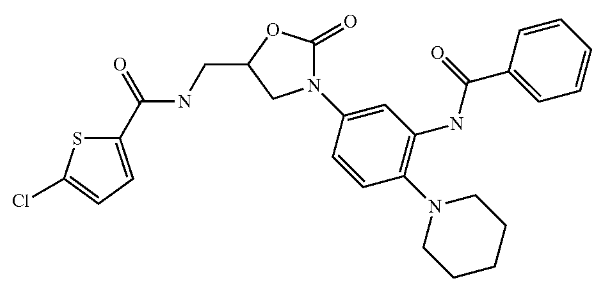 [SMILES: O=C(Nc1cc(N2CC(CNC(=O)c3ccc(Cl)s3)OC2=O)ccc1N1CCCCC1)c1ccccc1] | 4.76 | 75.1 |

| Example | Structure | Ret. time | HPLC [%] |
|---|---|---|---|
| 241 | 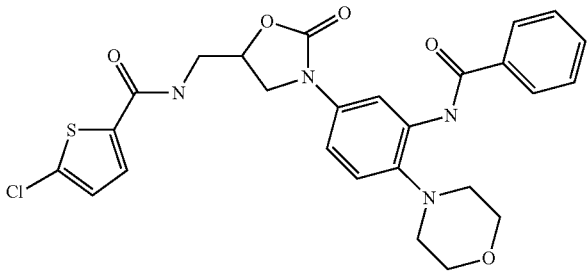 | 4.17 | 72.5 |
| 242 | 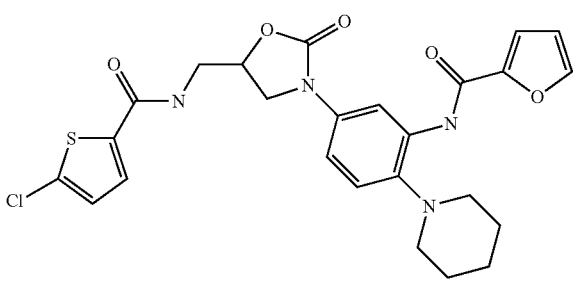 [SMILES: O=C(Nc1cc(N2CC(CNC(=O)c3ccc(Cl)s3)OC2=O)ccc1N1CCCCC1)c1ccco1] | 4.6 | 74.8 |
| 243 | 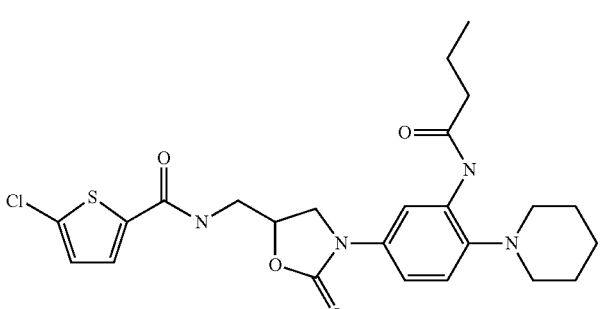 | 4.12 | 51.6 |
| 244 | 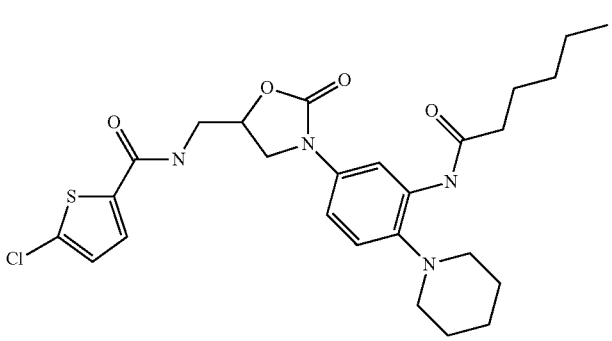 [SMILES: CCCCCC(=O)Nc1cc(N2CC(CNC(=O)c3ccc(Cl)s3)OC2=O)ccc1N1CCCCC1] | 4.71 | 66.2 |
| 245 | 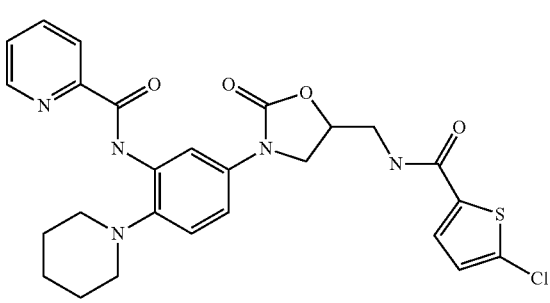 [SMILES: O=C(Nc1cc(N2CC(CNC(=O)c3ccc(Cl)s3)OC2=O)ccc1N1CCCCC1)c1ccccn1] | 4.86 | 62 |

-continued

| Example | Structure | Ret. time | HPLC [%] |
|---|---|---|---|
| 246 | 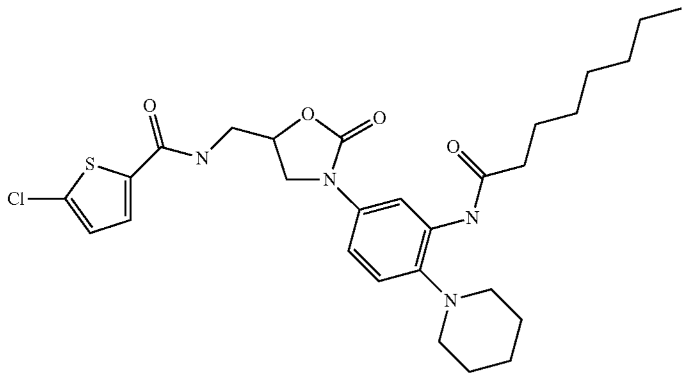 [SMILES: CCCCCCCC(=O)Nc1cc(N2CC(CNC(=O)c3ccc(Cl)s3)OC2=O)ccc1N1CCCCC1] | 5.23 | 58.3 |
| 247 | 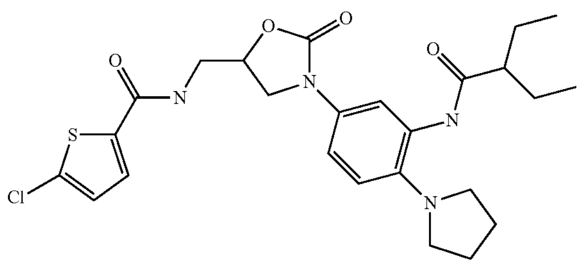 [SMILES: CCC(CC)C(=O)Nc1cc(N2CC(CNC(=O)c3ccc(Cl)s3)OC2=O)ccc1N1CCCC1] | 4.17 | 72.4 |
| 248 | 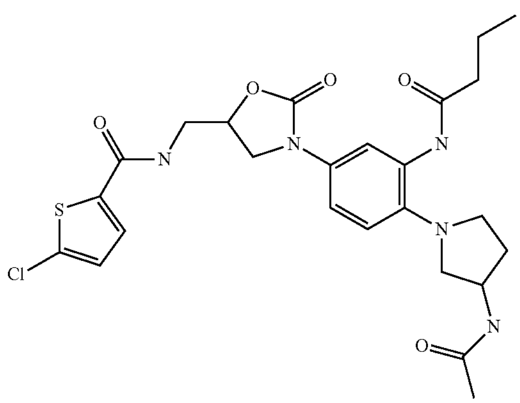 [SMILES: CCCC(=O)Nc1cc(N2CC(CNC(=O)c3ccc(Cl)s3)OC2=O)ccc1N1CCC(NC(C)=O)C1] | 3.35 | 59.6 |
| 249 | 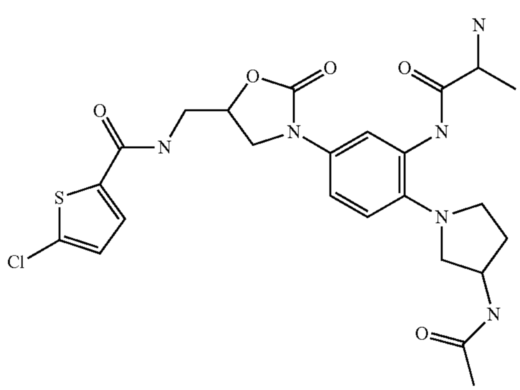 [SMILES: CC(=O)NC1CCN(c2ccc(N3CC(CNC(=O)c4ccc(Cl)s4)OC3=O)cc2NC(=O)C(C)N)C1] | 2.41 | 60.3 |

-continued
| Example | Structure | Ret. time | HPLC [%] |
|---|---|---|---|
| 250 | 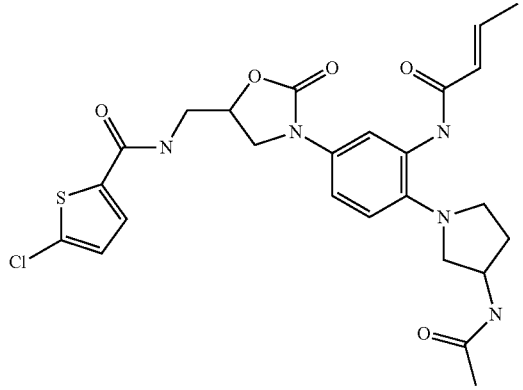 [SMILES: C/C=C/C(=O)Nc1cc(N2CC(CNC(=O)c3ccc(Cl)s3)OC2=O)ccc1N1CCC(NC(C)=O)C1] | 3.31 | 65.2 |
| 251 | 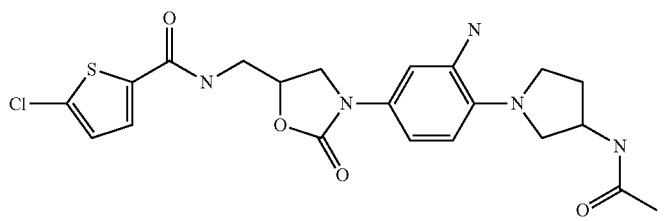 [SMILES: CC(=O)NC1CCN(c2ccc(N3CC(CNC(=O)c4ccc(Cl)s4)OC3=O)cc2N)C1] | 2.86 | 36.5 |
| 252 | 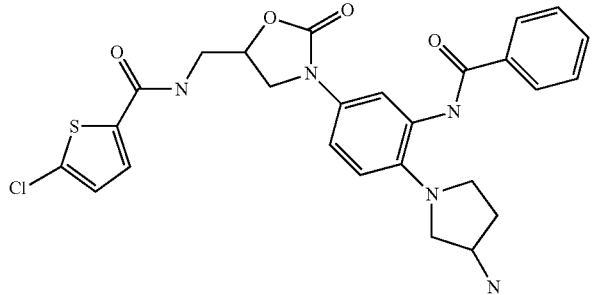 [SMILES: NC1CCN(c2ccc(N3CC(CNC(=O)c4ccc(Cl)s4)OC3=O)cc2NC(=O)c2ccccc2)C1] | 2.69 | 89.8 |
| 253 | 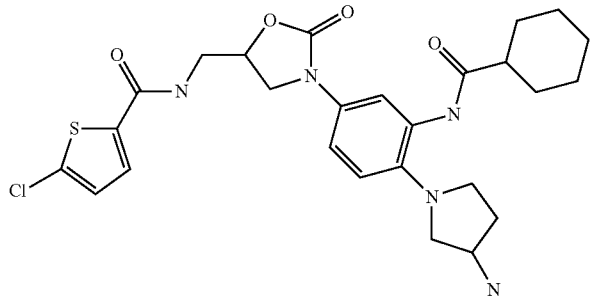 [SMILES: NC1CCN(c2ccc(N3CC(CNC(=O)c4ccc(Cl)s4)OC3=O)cc2NC(=O)C2CCCCC2)C1] | 2.81 | 67.4 |
| 254 | 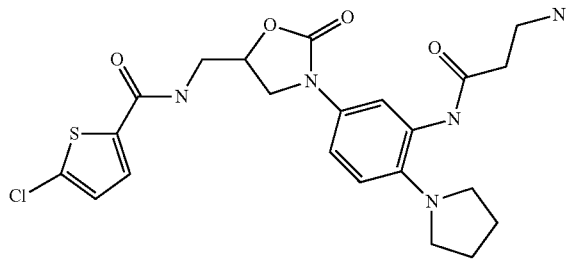 [SMILES: NCCC(=O)Nc1cc(N2CC(CNC(=O)c3ccc(Cl)s3)OC2=O)ccc1N1CCCC1] | 2.19 | 75.4 |

All products of the solid-phase-supported synthesis were characterized by LC-MS. As standard, the following separation system was used: HP 1100 with UV detector (208-400 nm), oven temperature 40° C., Waters-Symmetry C18 column (50 mm×2.1 mm, 3.5 µm), mobile phase A: 99.9% acetonitrile/0.1% formic acid, mobile phase B: 99.9% water/0.1% formic acid; gradient:

| Time | A:% | B:% | flow rate |
|------|------|------|-----------|
| 0.00 | 10.0 | 90.0 | 0.50 |
| 4.00 | 90.0 | 10.0 | 0.50 |
| 6.00 | 90.0 | 10.0 | 0.50 |
| 6.10 | 10.0 | 90.0 | 1.00 |
| 7.50 | 10.0 | 90.0 | 0.50 |

The substances were detected using a Micromass Quattro LCZ MS, ionization: ESI positive/negative.

In the structures listed above which comprise the radical(s)

or —O, what is meant is in each case a

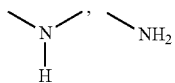

or —OH function.

We claim:

1. A compound of the formula (I)

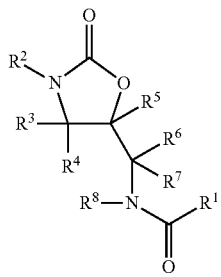

wherein $R^1$ represents an optionally benzo-fused thiophene group which may optionally be mono- or polysubstituted by a radical selected from the group consisting of halogen; cyano; nitro; amino; aminomethyl; $(C_1-C_8)$-alkyl which for its part may optionally be mono- or polysubstituted by halogen; $(C_3-C_7)$-cycloalkyl; $(C_1-C_8)$-alkoxy; imidazolinyl; —C(=NH)NH$_2$; carbamoyl; and mono- and di-$(C_1-C_4)$-alkyl-aminocarbonyl, $R^2$ represents

D-M-A-, where the radical "A" represents optionally substituted

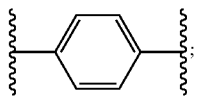

the radical "D" represents optionally substituted

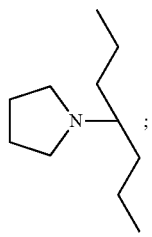

and the radical "M" represents a covalent bond;

where when the groups "A" and "D" defined above are substituted they are mono- or polysubstituted by a radical selected from the group consisting of halogen; trifluoromethyl; cyano; nitro; carbamoyl; $(C_1-C_6)$-alkanoyl; —OR$^{30}$; —NR$^{30}$R$^{31}$, and $(C_1-C_6)$-alkyl, where $R^{30}$ and $R^{31}$ are identical or different and independently of one another each represents hydrogen, $(C_1-C_4)$-alkyl, or C(O)R$^{33}$, where $R^{33}$ represents $(C_1-C_4)$-aminoalkyl, or $(C_1-C_8)$-alkyl, $R^3$, $R^4$, $R^5$, $R^6$, $R^7$ and $R^8$ are identical or different and each represents hydrogen or represents $(C_1-C_6)$-alkyl or a pharmaceutically acceptable salt or hydrate thereof except for compounds of the formula (I) in which the radical $R^1$ is an unsubstituted 2-thiophene radical and the radical $R^2$ is simultaneously a mono- or polysubstituted phenyl radical and the radicals $R^3$, $R^4$, $R^5$, $R^6$, $R^7$ and $R^8$ are each simultaneously hydrogen.

2. The compound of the formula (I) according to claim 1, wherein $R^1$ represents thiophene which may optionally be mono- or polysubstituted by halogen, amino, aminomethyl or $(C_1-C_8)$-alkyl, where the $(C_1-C_8)$-alkyl radical for its part may optionally be mono- or polysubstituted by halogen, $R^2$ represents

D-M-A-, where the radical "A" represents optionally substituted

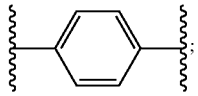 [SMILES: *c1ccc(*)cc1]

the radical "D" represents optionally substituted

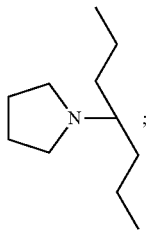

and
the radical "M" represents a covalent bond;
where
when the groups "A" and "D" defined above are substituted they are mono- or polysubstituted by a radical selected from the group consisting of halogen; trifluoromethyl; cyano; nitro; carbamoyl; ($C_1$-$C_6$)-alkanoyl; —OR$^{30}$; —NR$^{30}$R$^{31}$, and ($C_1$-$C_6$)-alkyl,
where
R$^{30}$ and R$^{31}$ are identical or different and independently of one another each represents hydrogen, ($C_1$-$C_4$)-alkyl, ($C_1$-$C_4$)-alkanoyl, or ($C_1$-$C_4$)-alkylaminocarbonyl,
R$^3$, R$^4$, R$^5$, R$^6$, R$^7$ and R$^8$ are identical or different and each represents hydrogen or represents ($C_1$-$C_6$)-alkyl
or a pharmaceutically acceptable salt or hydrate thereof
except for compounds of the formula (I) in which the radical R$^1$ is an unsubstituted 2-thiophene radical and the radical R$^2$ is simultaneously a mono- or polysubstituted phenyl radical and the radicals R$^3$, R$^4$, R$^5$, R$^6$, R$^7$ and R$^8$ are each simultaneously hydrogen.

3. The compound of the formula (I) according to claim 1, wherein
R$^1$ represents thiophene which may optionally be mono- or polysubstituted by halogen or by ($C_1$-$C_8$)-alkyl, where the ($C_1$-$C_8$)-alkyl radical for its part may optionally be mono- or polysubstituted by halogen,
R$^2$ represents

D-M-A-, where:
the radical "A" represents optionally substituted

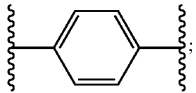

the radical "D" represents optionally substituted

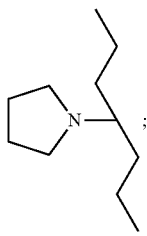

and
the radical "M" represents a covalent bond;
where
when the groups "A" and "D" defined above are substituted they are mono- or polysubstituted by a radical selected from the group consisting of halogen; trifluoromethyl; cyano; ($C_1$-$C_3$)-alkanoyl; —OH; —NR$^{30}$R$^{31}$; and ($C_1$-$C_4$)-alkyl;
where
R$^{30}$ and R$^{31}$ are identical or different and independently of one another each represents hydrogen, ($C_1$-$C_4$)-alkyl or ($C_1$-$C_3$)-alkanoyl,
R$^3$, R$^4$, R$^5$, R$^6$, R$^7$ and R$^8$ are identical or different and each represents hydrogen or represents ($C_1$-$C_6$)-alkyl
or a pharmaceutically acceptable salt or hydrate thereof
except for compounds of the formula (I) in which the radical R$^1$ is an unsubstituted 2-thiophene radical and the radical R$^2$ is simultaneously a mono- or polysubstituted phenyl radical and the radicals R$^3$, R$^4$, R$^5$, R$^6$, R$^7$ and R$^8$ are each simultaneously hydrogen.

4. The compound of the formula (I) according to claim 1, wherein
R$^1$ represents 2-thiophene which may optionally be substituted in the 5-position by a radical selected from the group consisting of chlorine, bromine, methyl and trifluoromethyl,
R$^2$ represents

D-M-A-, where:
the radical "A" represents optionally substituted

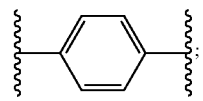

the radical "D" represents optionally substituted

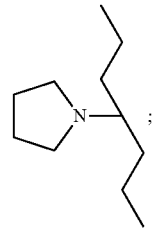

and
the radical "M" represents a covalent bond;
where
when the groups "A" and "D" defined above are substituted they are mono- or polysubstituted by a radical selected from the group consisting of halogen; trifluoromethyl; cyano; ($C_1$-$C_3$)-alkanoyl; —OH; —NR$^{30}$R$^{31}$; and ($C_1$-$C_4$)-alkyl;
where
R$^{30}$ and R$^{31}$ are identical or different and independently of one another each represents hydrogen, ($C_1$-$C_4$)-alkyl or ($C_1$-$C_3$)-alkanoyl,
R$^3$, R$^4$, R$^5$, R$^6$, R$^7$ and R$^8$ are identical or different and each represents hydrogen or represents ($C_1$-$C_4$)-alkyl
or a pharmaceutically acceptable salt or hydrate thereof except for compounds of the formula (I) in which the radical $R^1$ is an unsubstituted 2-thiophene radical and the radical $R^2$ is simultaneously a mono- or polysubstituted phenyl radical and the radicals $R^3$, $R^4$, $R^5$, $R^6$, $R^7$ and $R^8$ are each simultaneously hydrogen.

5. Process for preparing the compound of claim 1, where either according to a process alternative (A) a compound of the formula (II)

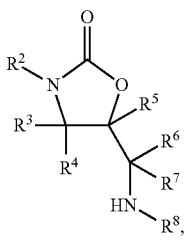

(II)

in which
the radicals $R^2$, $R^3$, $R^4$, $R^5$, $R^6$, $R^7$ and $R^8$ are each as defined in claim 1 is reacted with carboxylic acid of the formula (III)

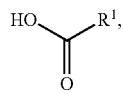

(III)

in which
the radical $R^1$ is as defined in claim 1,
or else with a corresponding carbonyl halide, or else with a corresponding symmetric or mixed carboxylic anhydride of the carboxylic acid of the formula (III) defined above in an inert solvent, if appropriate in the presence of an activating or coupling agent and/or a base, to give a compound of the formula (I)

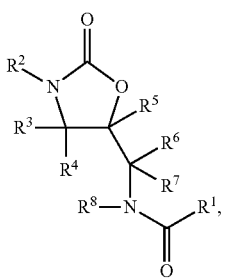

(I)

in which
the radicals $R^1$, $R^2$, $R^3$, $R^4$, $R^5$, $R^6$, $R^7$ and $R^8$ are each as defined in claim 1, or else according to a process alternative (B) a compound of the formula (IV)

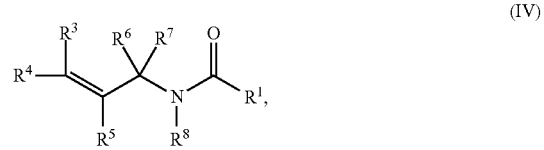

(IV)

in which
the radicals $R^1$, $R^3$, $R^4$, $R^5$, $R^6$, $R^7$ and $R^8$ are each as defined in claim 1, is converted, using a suitable selective oxidizing agent in an inert solvent, into the corresponding epoxide of the formula (V)

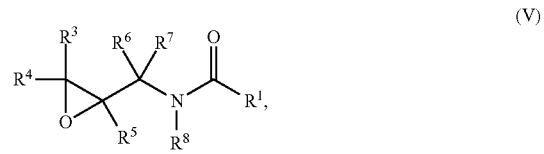

(V)

in which
the radicals $R^1$, $R^3$, $R^4$, $R^5$, $R^6$, $R^7$ and $R^8$ are each as defined in claim 1,
and, by reaction in an inert solvent, if appropriate in the presence of a catalyst, with an amine of the formula (VI)

$R^2$—$NH_2$         (VI), in which
the radical $R^2$ is as defined in claim 1,
a compound of the formula (VII)

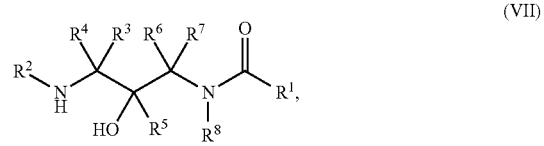

(VII)

in which
the radicals $R^1$, $R^2$, $R^3$, $R^4$, $R^5$, $R^6$, $R^7$ and $R^8$ are each as defined in claim 1, is initially prepared and,
subsequently, in an inert solvent in the presence of phosgene or a phosgene equivalent, cyclized to give a compound of the formula (I)

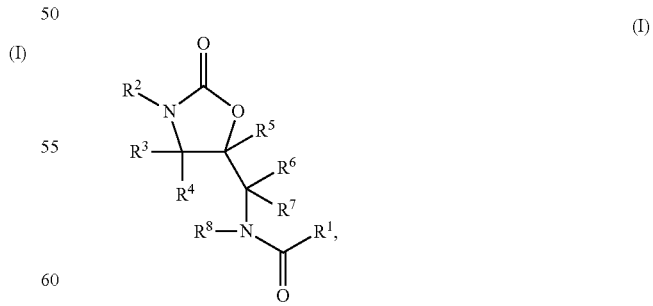

(I)

in which
the radicals $R^1$, $R^2$, $R^3$, $R^4$, $R^5$, $R^6$, $R^7$ and $R^8$ are each as defined in claim 1,
where—both for process alternative (A) and for process alternative (B)—in the case where $R^2$ contains a 3- to 7-membered saturated or partially unsaturated cyclic hydrocarbon radical having one or more identical or different heteroatoms from the group consisting of N and S, an oxidation with a selective oxidizing agent to afford the corresponding sulphone, sulphoxide or N-oxide may follow and/or where—both for process alternative (A) and for process alternative (B)—in the case where the compound prepared in this manner has a cyano group in the molecule, an amidination of this cyano group by customary methods may follow and/or where—both for process alternative (A) and for process alternative (B)—in the case where the compound prepared in this manner has a BOC amino protective group in the molecule, removal of this BOC amino protective group by customary methods may follow and/or where—both for process alternative (A) and for process alternative (B)—in the case where the compound prepared in this manner has an aniline or benzylamine radical in the molecule, a reaction of this amino group with a carboxylic acid, carboxylic anhydride, carbonyl chloride, isocyanate, sulphonyl chloride or alkyl halide to give the corresponding derivative may follow and/or where—both for process alternative (A) and for process alternative (B)—in the case where the compound prepared in this manner has a phenyl ring in the molecule, a reaction with chlorosulphonic acid and subsequent reaction with an amine to give the corresponding sulphonamide may follow.

6. A pharmaceutical composition comprising at least one compound of the formula (I) according to claim 1 and one or more pharmacologically acceptable auxiliaries or excipients.

7. A method for treatment of atherosclerosis comprising administering an effective amount of a compound of claim 1 to a patient in need thereof.

8. The compound of claim 1 wherein $R^1$ represents an optionally substituted 2-thiophene group, and wherein said halogen substituent is chlorine or bromine, and said $(C_1-C_8)$-alkyl substituent is methyl, where the methyl radical for its part optionally may be mono- or polysubstituted by fluorine.

9. The process of claim 5 wherein in process alternative "A", the corresponding carbonyl halide of carboxylic acid (III) is a carbonyl chloride.

10. The process of claim 5 wherein in process alternative "B", the phosgene equivalent employed in the cyclization of compound (VII) is carbonyldimidazole (CDI).

11. A method for treatment of a thromboembolic disorder comprising administering to a patient in need thereof an effective amount of a compound of claim 1, wherein the thromboembolic disorder is myocardial infarct, pulmonary embolism or deep venous thrombosis.

12. The compound of claim 1 that is purified and isolated.

13. A pharmaceutical composition comprising at least one compound of the formula (I) according to claim 2 and one or more pharmacologically acceptable auxiliaries or excipients.

14. A pharmaceutical composition comprising at least one compound of the formula (I) according to claim 3 and one or more pharmacologically acceptable auxiliaries or excipients.

15. A pharmaceutical composition comprising at least one compound of the formula (I) according to claim 4 and one or more pharmacologically acceptable auxiliaries or excipients.

16. A method for the treatment of atherosclerosis comprising administering an effective amount of the composition of claim 13 to a patient in need thereof.

17. A method for the treatment of myocardial infarct, pulmonary embolism or deep venous thrombosis comprising administering an effective amount of the composition of claim 13 to a patient in need thereof.

18. A method for the treatment of atherosclerosis comprising administering an effective amount of the composition of claim 14 to a patient in need thereof.

19. A method for the treatment of myocardial infarct, pulmonary embolism or deep venous thrombosis comprising administering an effective amount of the composition of claim 14 to a patient in need thereof.

20. A method for the treatment of atherosclerosis comprising administering an effective amount of the composition of claim 15 to a patient in need thereof.

21. A method for the treatment of myocardial infarct, pulmonary embolism or deep venous thrombosis comprising administering an effective amount of the composition of claim 15 to a patient in need thereof.

* * * * *